United States Patent
Wilson et al.

(10) Patent No.: US 8,460,316 B2
(45) Date of Patent: Jun. 11, 2013

(54) SYSTEMS AND METHODS FOR ENDOLUMINAL VALVE CREATION

(75) Inventors: Fletcher T. Wilson, San Francisco, CA (US); Rhunjay J. Yu, Mountain View, CA (US)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 88 days.

(21) Appl. No.: 13/035,818

(22) Filed: Feb. 25, 2011

(65) Prior Publication Data

US 2011/0264125 A1 Oct. 27, 2011

Related U.S. Application Data

(60) Provisional application No. 61/308,503, filed on Feb. 26, 2010, provisional application No. 61/349,349, filed on May 28, 2010, provisional application No. 61/393,996, filed on Oct. 18, 2010, provisional application No. 61/420,307, filed on Dec. 6, 2010.

(51) Int. Cl.
*A61B 17/32* (2006.01)

(52) U.S. Cl.
USPC ............ 606/139; 606/151; 606/159; 606/170

(58) Field of Classification Search
USPC ................. 606/110–113, 139–144, 148, 151, 606/159, 167, 180, 190–192, 213, 170
See application file for complete search history.

(56) References Cited

U.S. PATENT DOCUMENTS

| | | | |
|---|---|---|---|
| 5,464,395 A | 11/1995 | Faxon et al. | |
| 5,810,847 A | 9/1998 | Laufer et al. | |
| 6,506,178 B1 | 1/2003 | Schubart et al. | |
| 6,902,576 B2 | 6/2005 | Drasler et al. | |
| 7,179,249 B2 | 2/2007 | Steward et al. | |
| 7,517,352 B2 | 4/2009 | Evans | |
| 7,918,870 B2 | 4/2011 | Kugler et al. | |
| 7,927,305 B2 | 4/2011 | Yribarren et al. | |
| 7,938,819 B2 | 5/2011 | Kugler et al. | |
| 7,955,346 B2 * | 6/2011 | Mauch et al. | 606/159 |
| 8,025,655 B2 | 9/2011 | Kugler et al. | |
| 8,083,727 B2 | 12/2011 | Kugler et al. | |
| 8,100,860 B2 | 1/2012 | Von Oepen et al. | |

(Continued)

FOREIGN PATENT DOCUMENTS

WO 2010074853 A1 7/2010

OTHER PUBLICATIONS

International Search Report dated Jul. 7, 2011 for PCT Application No. PCT/US2011/026370.

(Continued)

*Primary Examiner* — Kathleen Holwerda
(74) *Attorney, Agent, or Firm* — Vista IP Law Group, LLP

(57) ABSTRACT

A method of manipulating tissue at a vessel includes advancing a device distally relative to an opening at an interior surface of the vessel, and into a first wall portion of a vessel until an entirety of the device is within the wall of the vessel, the device having a distal end, a proximal end, and a cutting element coupled to the proximal end, and using the cutting element to increase a size of the opening by retracting the device proximally.

12 Claims, 59 Drawing Sheets

U.S. PATENT DOCUMENTS

| | | | |
|---|---|---|---|
| 8,114,123 B2* | 2/2012 | Brenzel et al. | 606/213 |
| 2002/0103459 A1 | 8/2002 | Sparks et al. | |
| 2004/0167558 A1 | 8/2004 | Igo et al. | |
| 2005/0075665 A1* | 4/2005 | Brenzel et al. | 606/213 |
| 2005/0165466 A1 | 7/2005 | Morris et al. | |
| 2009/0254051 A1 | 10/2009 | Von Oepen et al. | |
| 2010/0152682 A1 | 6/2010 | Mauch et al. | |
| 2010/0152843 A1* | 6/2010 | Mauch et al. | 623/2.11 |
| 2010/0256599 A1 | 10/2010 | Kassab et al. | |

OTHER PUBLICATIONS

Lugli, M., et al., Neovalve construction in the deep venous incompetence, Twentieth Annual Meeting of the American Venous Forum, Charleston, SC, Feb. 20-23, 2008.

Final Office Action dated Apr. 4, 2013 for U.S. Appl. No. 13/035,752.

\* cited by examiner

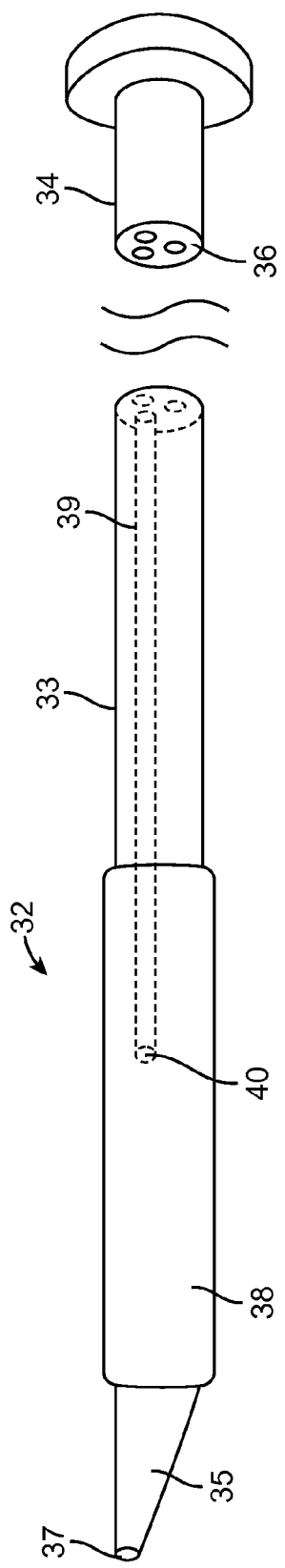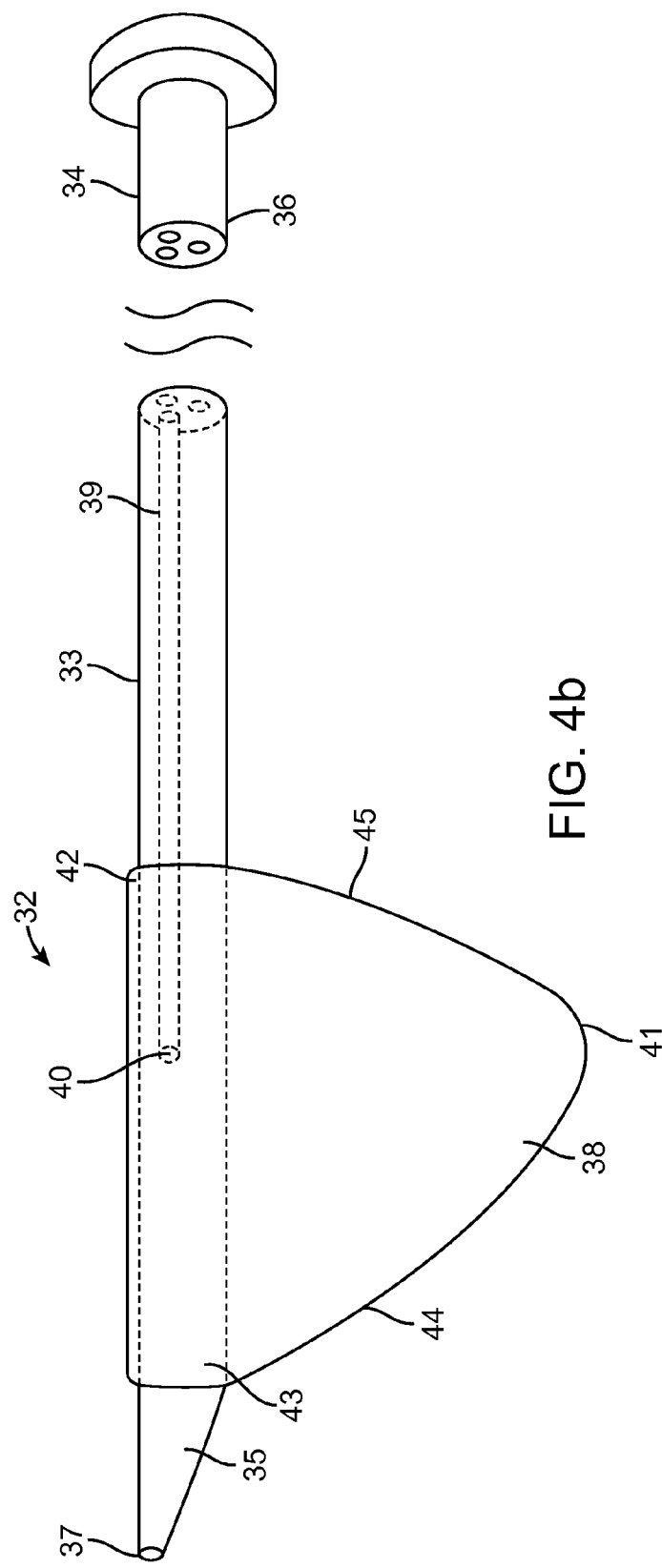

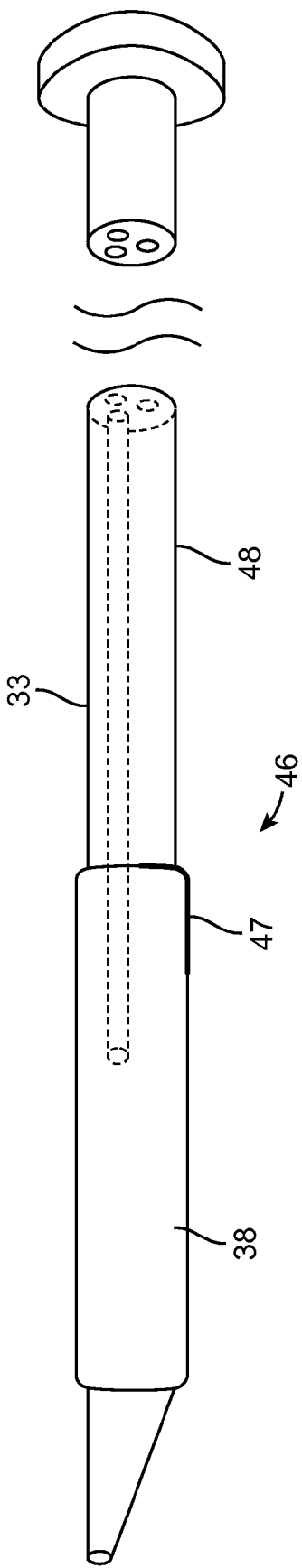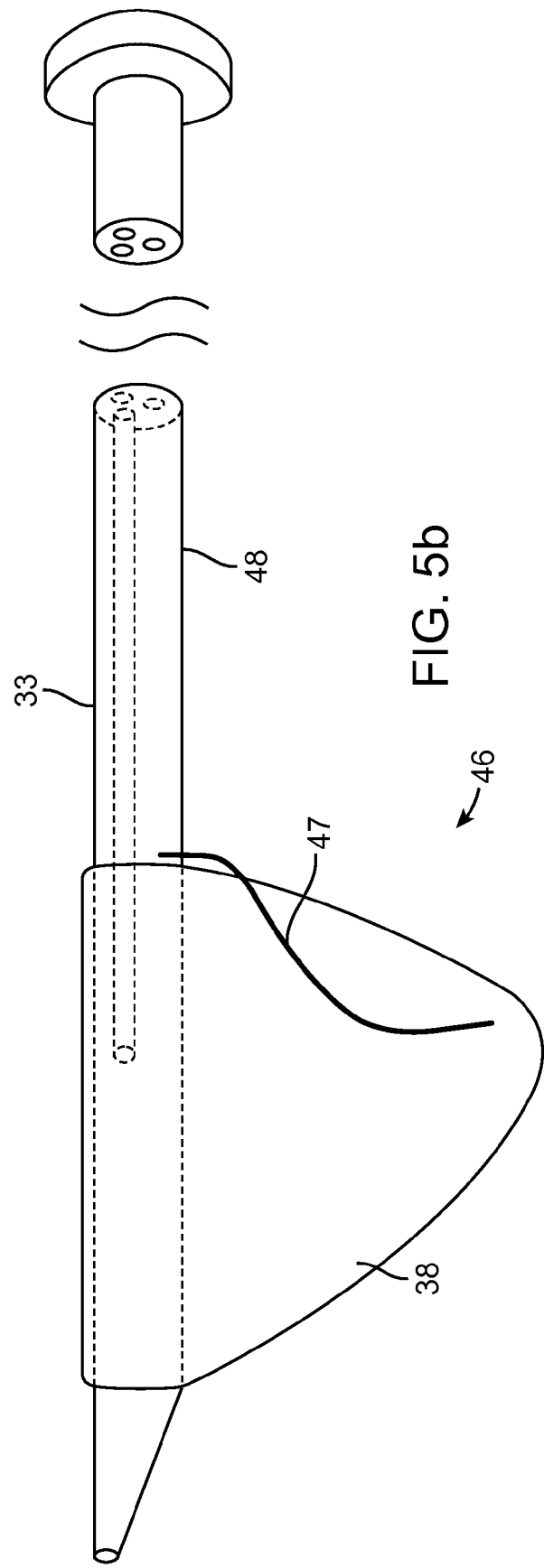
FIG. 5a
FIG. 5b

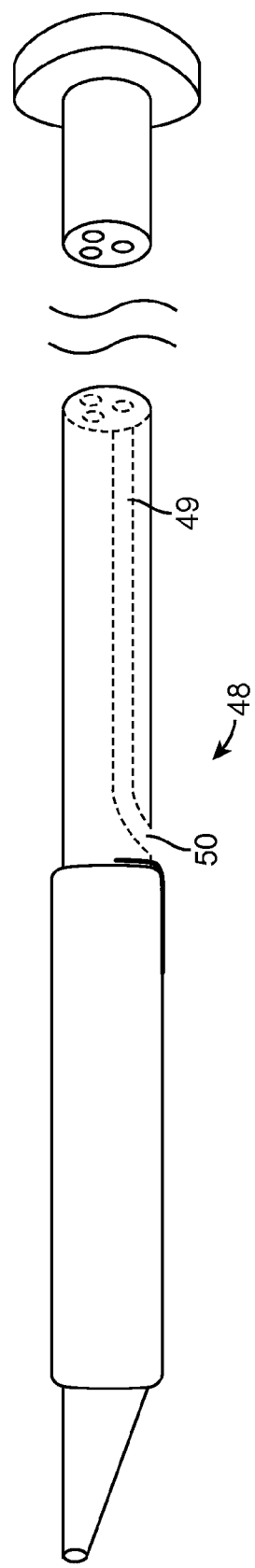
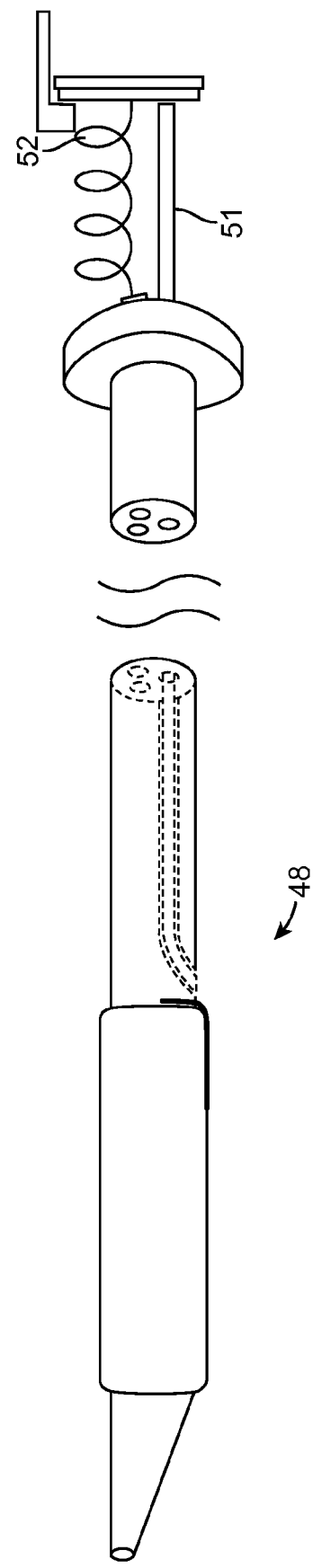
FIG. 6a
FIG. 6b

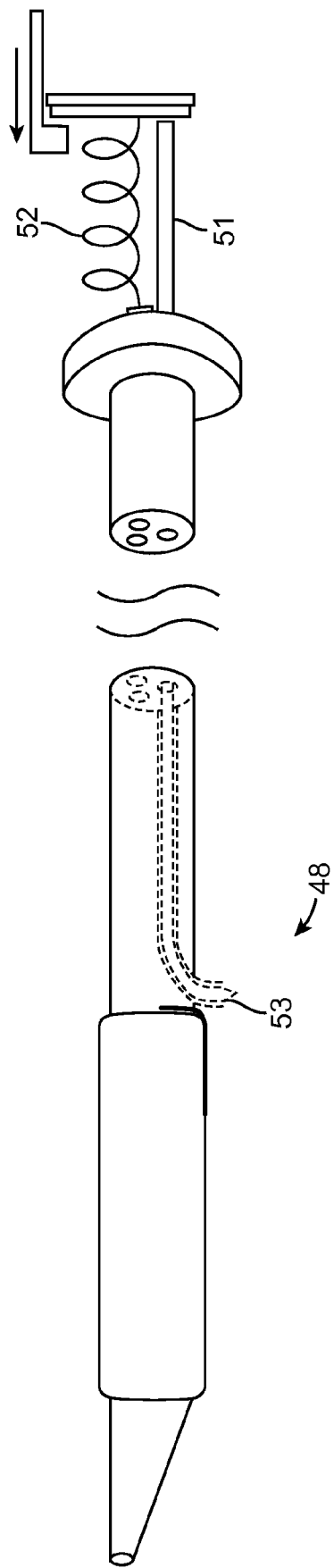
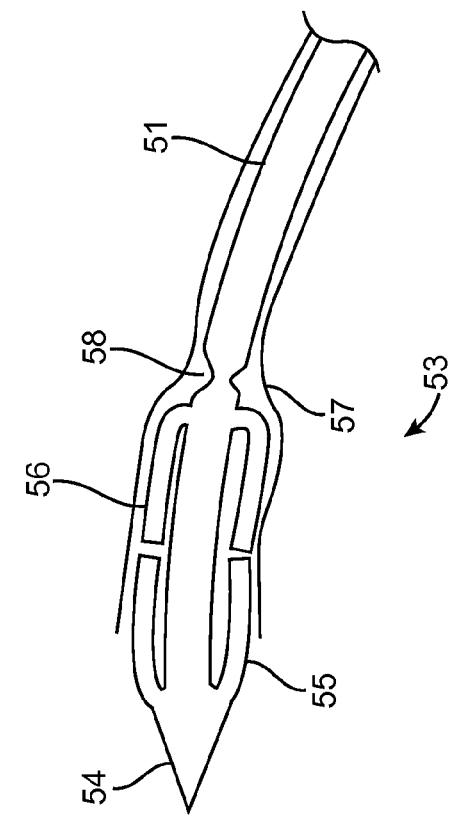
FIG. 6c
FIG. 6d

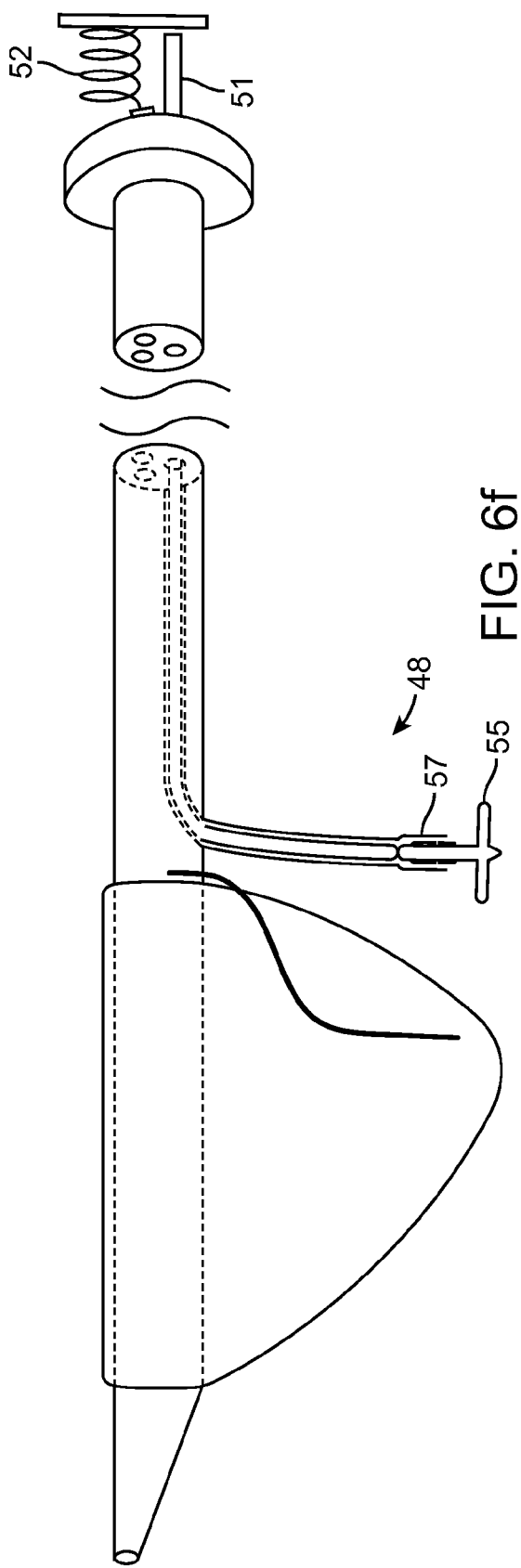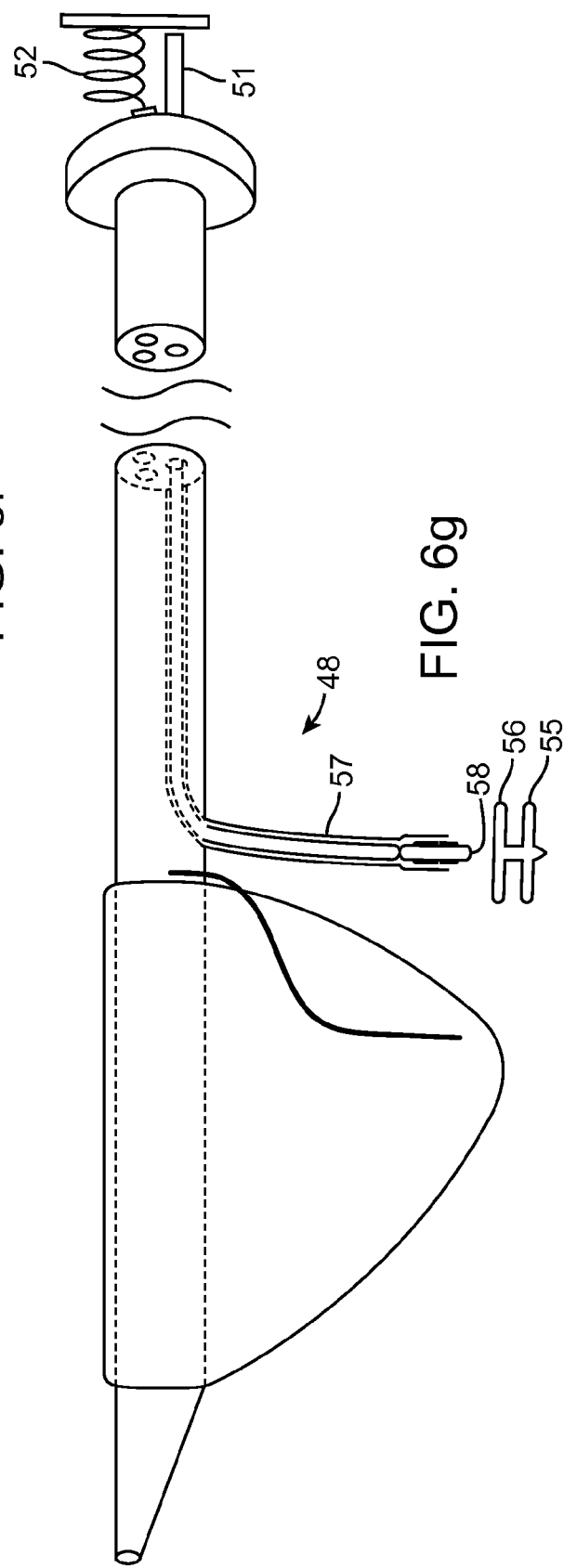

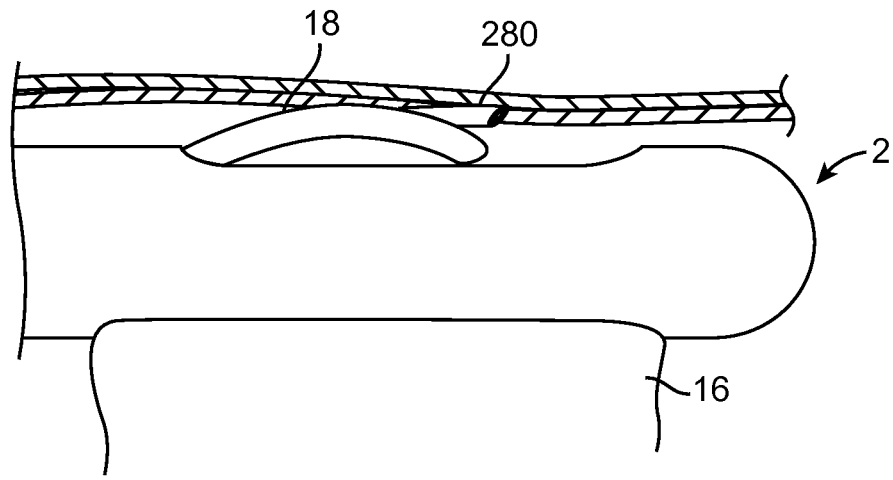
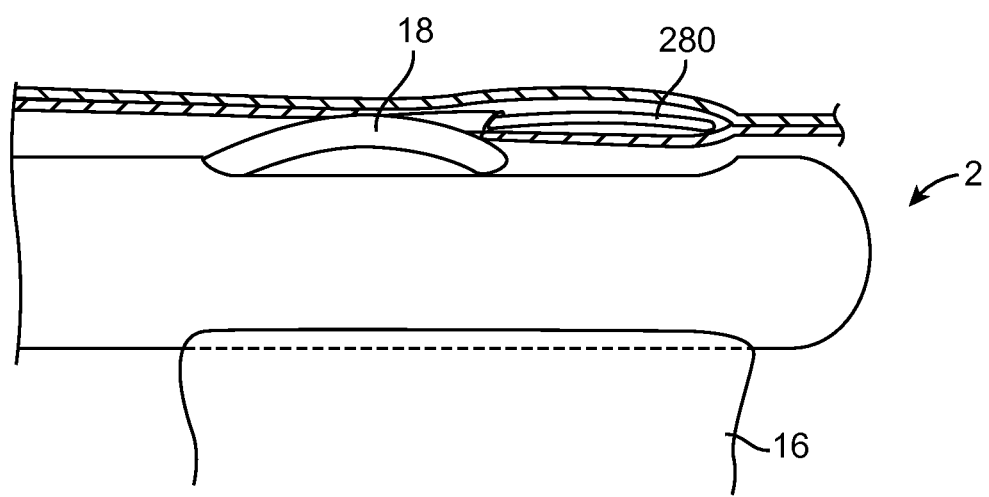
FIG. 30

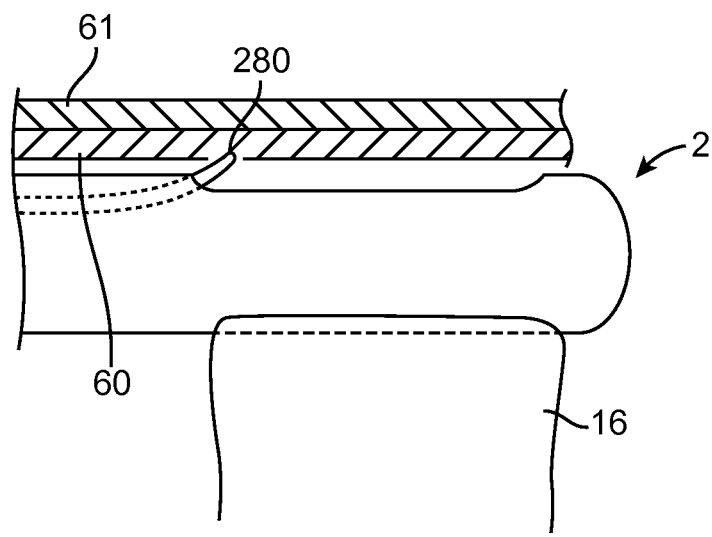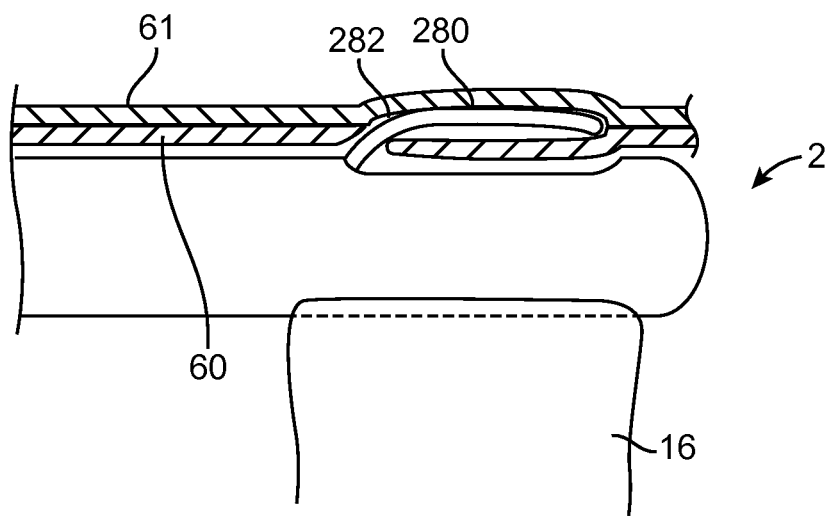
FIG. 31

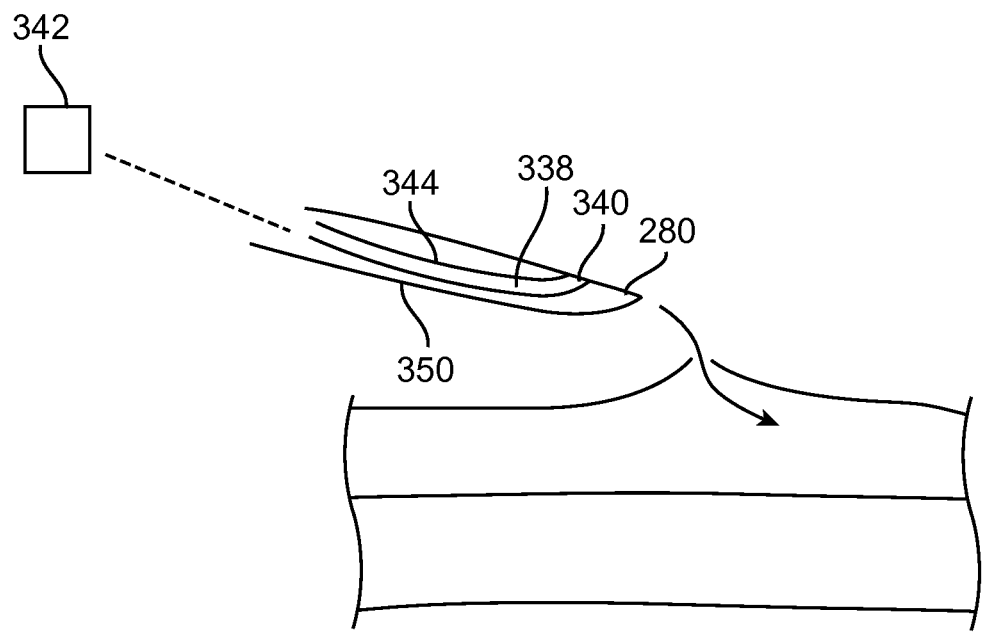
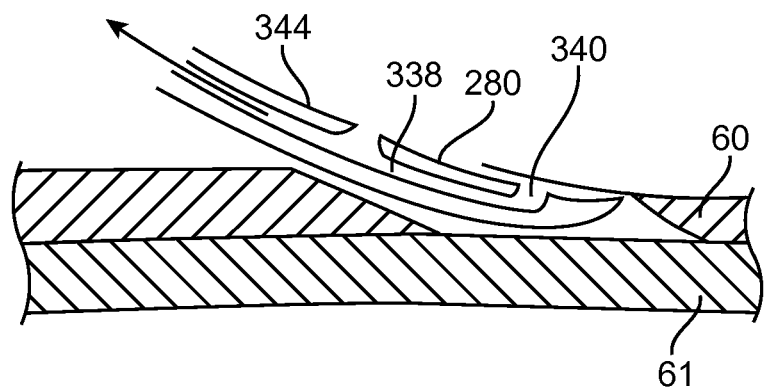
FIG. 38

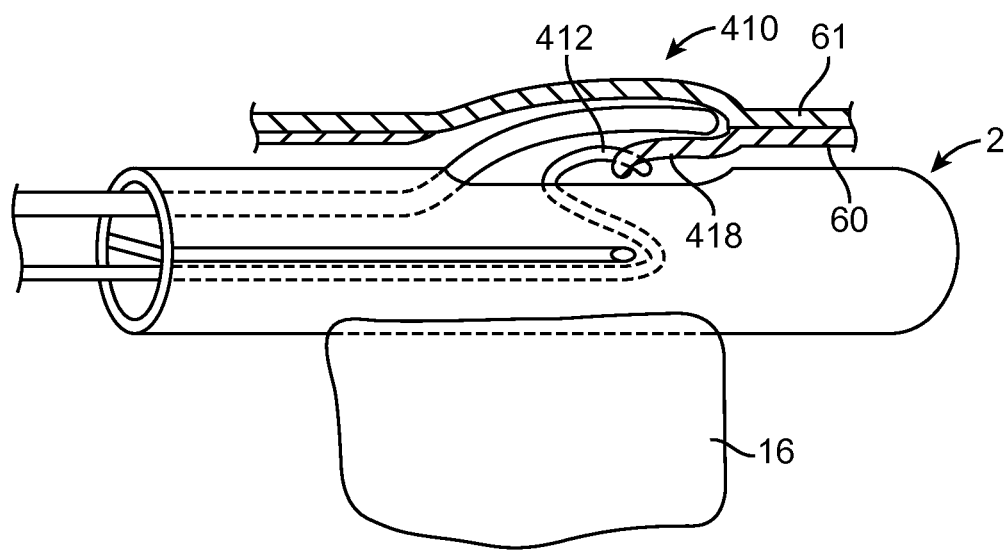
FIG. 40
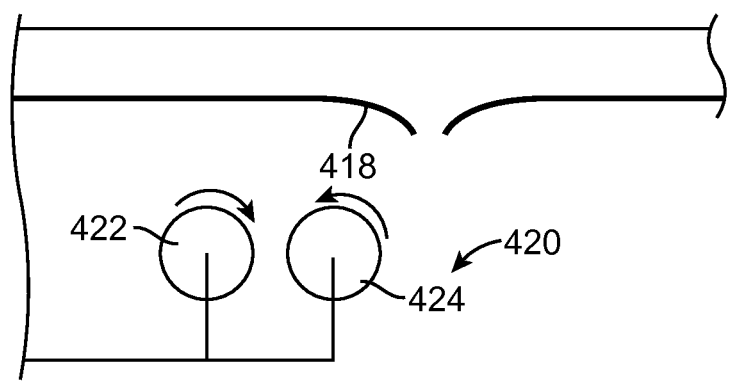
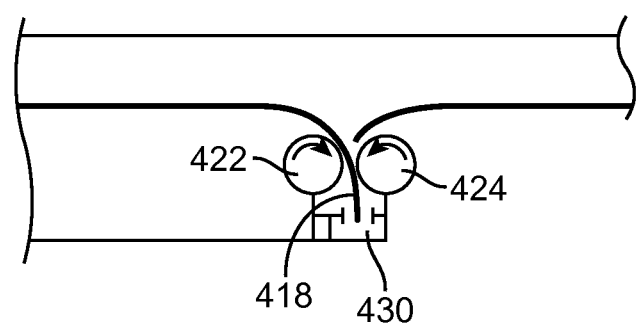
FIG. 41

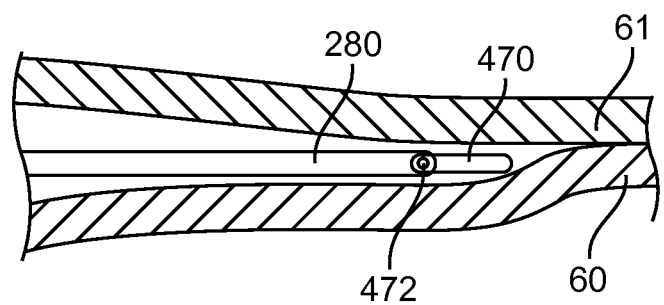
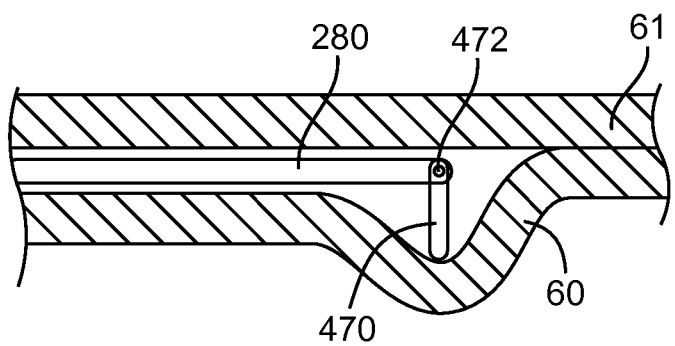
FIG. 44
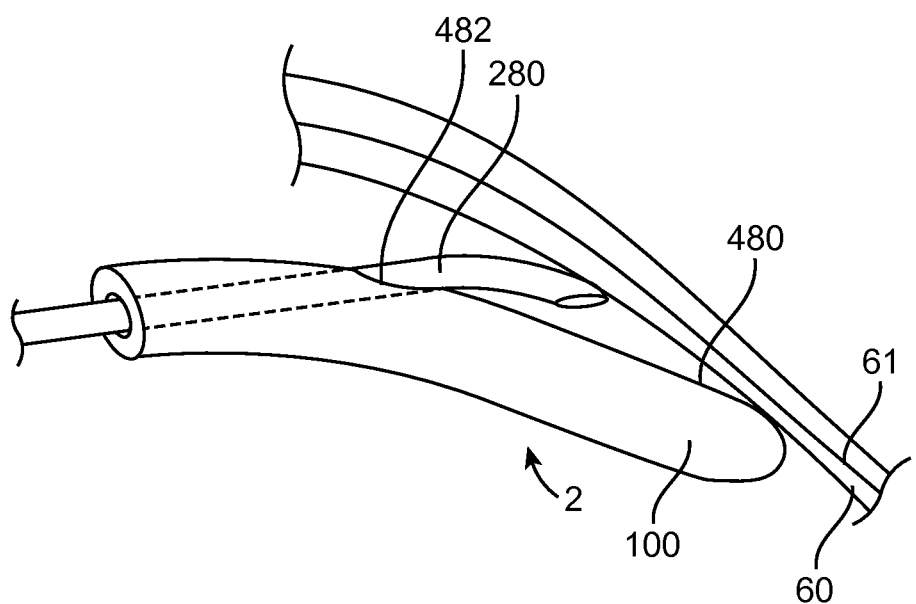
FIG. 45

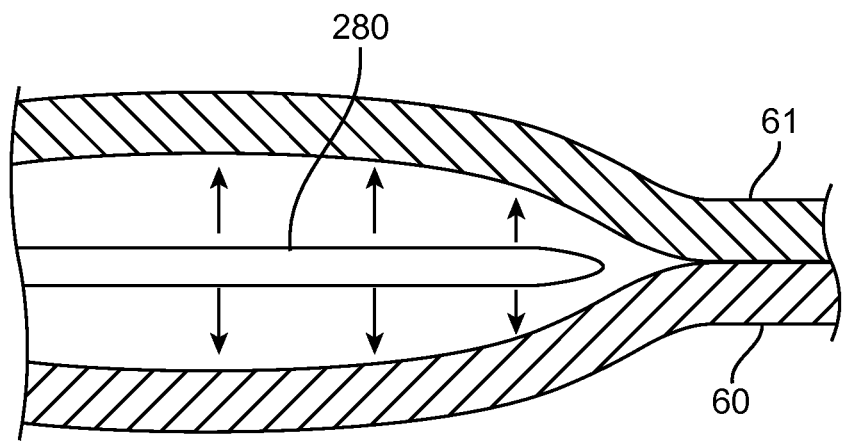
FIG. 46
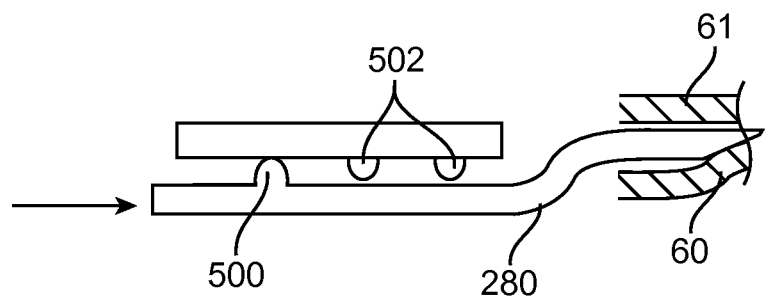
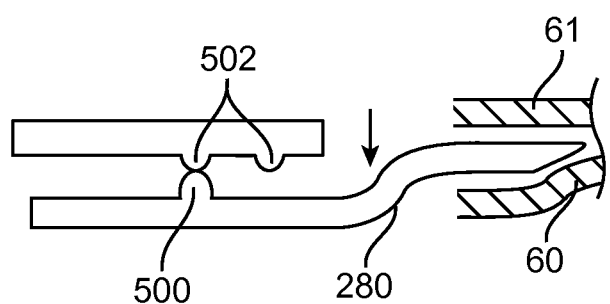
FIG. 47

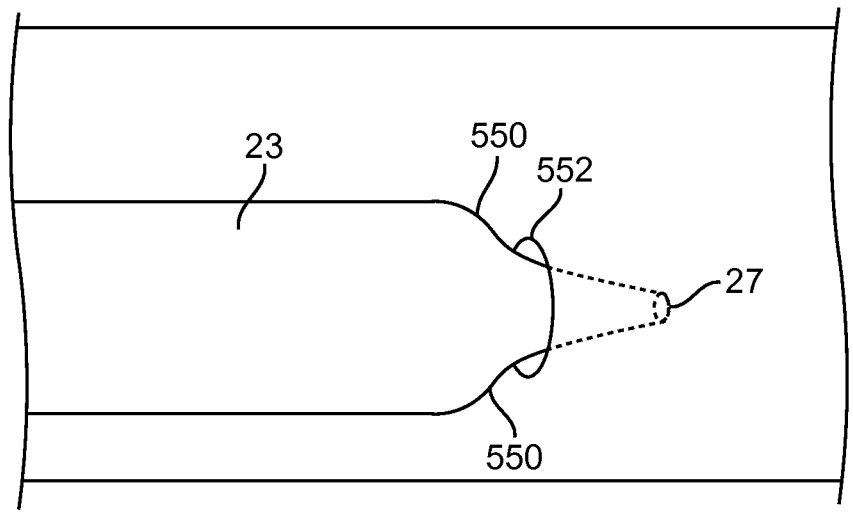
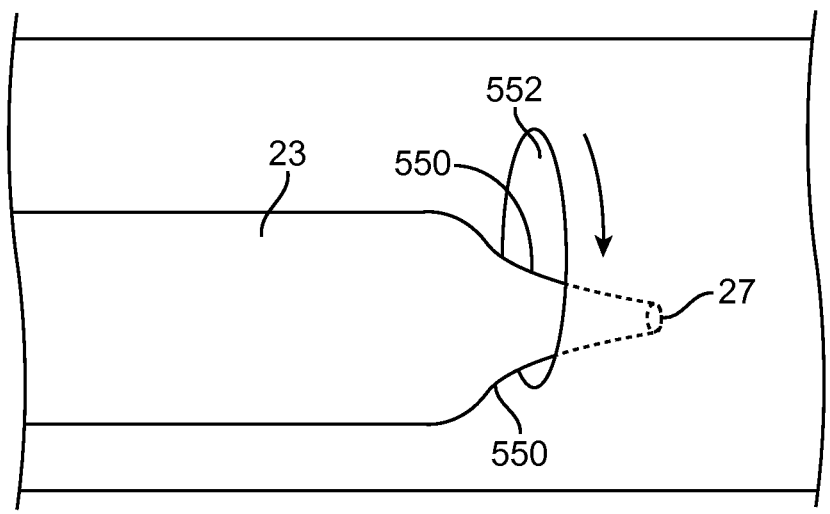
FIG. 53

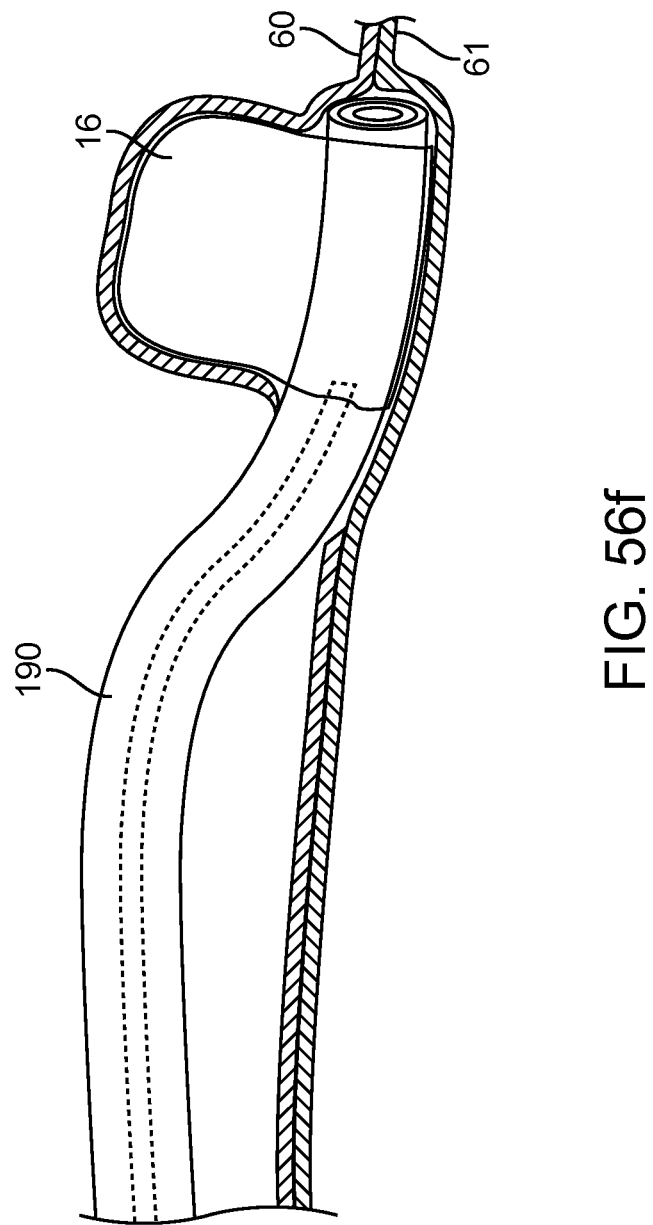

SYSTEMS AND METHODS FOR ENDOLUMINAL VALVE CREATION

RELATED APPLICATION DATA

This application claims priority to and the benefit of U.S. Provisional Patent Application Nos. 61/308,503, filed on Feb. 26, 2010, 61/349,349, filed on May 28, 2010, 61/393,996, filed on Oct. 18, 2010, and 61/420,307, filed on Dec. 6, 2010, the entire disclosure of all of which is expressly incorporated by reference herein.

GOVERNMENT RIGHTS

This invention was made with Government support under contract RR025742 awarded by the National Institutes of Health. The Government has certain rights in this invention.

FIELD

The present application pertains generally to medical systems and methods for creation of an autologous tissue valves within a mammalian body.

BACKGROUND

Venous reflux is a medical condition affecting the circulation of blood, such as in the lower extremities. The valves in the vessel that normally force blood back towards the heart cannot function properly. As a result, blood pools up in the legs, and the veins of the legs become distended. Applicant of the subject application determines that new systems and methods for treating venous reflux would be desirable.

SUMMARY

In accordance with some embodiments, a device for manipulating tissue at a vessel includes an elongated member having a proximal end and a distal end, a guide member at the distal end of the elongated member, the guide member having a blunt distal tip for engagement against an interior wall of the vessel, and a tissue cutting device at the distal end of the elongated member, wherein the tissue cutting device has a sharp tip that is proximal to the blunt distal tip of the guide member.

In accordance with any of the embodiments described herein, the tissue cutting device is configured to cut tissue at the interior wall of the vessel while the guide member engages against the interior wall of the vessel.

In accordance with any of the embodiments described herein, the guide member is configured to orient the tissue cutting device at a desired angle relative to the interior wall of the vessel.

In accordance with any of the embodiments described herein, the guide member is configured to apply pressure at a surface of the interior wall of the vessel to thereby provide tension at the surface.

In accordance with any of the embodiments described herein, the tissue cutting device comprises a tube having a lumen for delivering fluid.

In accordance with any of the embodiments described herein, the device further includes a source of agent for delivering the agent to the tissue cutting device.

In accordance with any of the embodiments described herein, the agent comprises a contrast agent.

In accordance with any of the embodiments described herein, the tissue cutting device has a tapered configuration.

In accordance with any of the embodiments described herein, the tissue cutting device is tapered proximally from a first longitudinal side of the cutting device to a second longitudinal side of the cutting device that is opposite from the first longitudinal side, the first longitudinal side of the cutting device being further from a longitudinal axis of the elongated member than the second longitudinal side.

In accordance with any of the embodiments described herein, a proximal end of the guide member and a proximal end of the tissue cutting device collectively form a stopper for preventing tissue located between the guide member and the tissue cutting device from moving proximally past the stopper.

In accordance with any of the embodiments described herein, the guide member and the elongated member have a unity configuration.

In accordance with any of the embodiments described herein, the tissue cutting device and the elongated member have a unity configuration.

In accordance with any of the embodiments described herein, a length of the tissue cutting device dictates how far the tissue cutting device is to penetrate into the interior wall of the vessel.

In accordance with other embodiments, a device for manipulating tissue at a vessel includes an elongated member having a proximal end and a distal end, a guide member extending distally from the distal end of the elongated member, the guide member configured for engagement against an interior wall of the vessel, a tissue cutting device extending distally from the distal end of the elongated member, wherein a proximal end of the guide member and a proximal end of the tissue cutting device collectively form a stopper for preventing tissue located between the guide member and the tissue cutting device from moving proximally past the stopper.

In accordance with any of the embodiments described herein, the guide member has a blunt distal tip, and the tissue cutting device has a sharp tip that is proximal to the blunt distal tip of the guide member, and the stopper is configured for preventing the cut tissue from moving proximally past the stopper.

In accordance with any of the embodiments described herein, the tissue cutting device is configured to cut tissue at the interior wall of the vessel while the guide member engages against the interior wall of the vessel.

In accordance with any of the embodiments described herein, the guide member is configured to orient the tissue cutting device at a desired angle relative to the interior wall of the vessel.

In accordance with any of the embodiments described herein, the guide member is configured to apply pressure at a surface of the interior wall of the vessel to thereby provide tension at the surface.

In accordance with any of the embodiments described herein, the tissue cutting device comprises a tube having a lumen for delivering fluid.

In accordance with any of the embodiments described herein, the device further includes a source of agent for delivering the agent to the tissue cutting device.

In accordance with any of the embodiments described herein, the agent comprises a contrast agent.

In accordance with any of the embodiments described herein, the tissue cutting device has a tapered configuration.

In accordance with any of the embodiments described herein, the tissue cutting device is tapered from a first longitudinal side of the cutting device to a second longitudinal side of the cutting device that is opposite from the first longitudinal side, the first longitudinal side of the cutting device being further from a longitudinal axis of the elongated member than the second longitudinal side.

In accordance with any of the embodiments described herein, the guide member and the elongated member have a unity configuration.

In accordance with any of the embodiments described herein, the tissue cutting device and the elongated member have a unity configuration.

In accordance with any of the embodiments described herein, a length of the tissue cutting device dictates how far the tissue cutting device is to penetrate into the interior wall of the vessel.

In accordance with other embodiments, a method of manipulating tissue at a vessel includes applying tension by a first device to a surface of an interior wall of the vessel, and using a second device to penetrate tissue at the interior wall of the vessel while the tension is applied by the first device to the surface of the interior wall of the vessel.

In accordance with any of the embodiments described herein, the method further includes advancing the second device distally inside the interior wall of the vessel until a stopper at a proximal end of the second device engages with vessel tissue.

In accordance with any of the embodiments described herein, the second device has a lumen, and the method further comprises delivering fluid through the lumen of the second device into a space that is inside the interior wall of the vessel.

In accordance with any of the embodiments described herein, the fluid is delivered to enlarge the space inside the interior wall of the vessel.

In accordance with any of the embodiments described herein, the second device penetrates the tissue to create an opening at the tissue, and wherein the method further comprises increasing a size of the opening.

In accordance with any of the embodiments described herein, the space is enlarged to create a flap inside the vessel.

In accordance with any of the embodiments described herein, the method further includes securing the flap relative to the vessel.

In accordance with any of the embodiments described herein, the second device penetrates the tissue to create an opening at the tissue, and wherein the method further comprises increasing a size of the opening.

In accordance with any of the embodiments described herein, the first device is also used to orient the second device so that the second device is at a desired angle relative to the surface of the interior wall of the vessel.

In accordance with any of the embodiments described herein, the desired angle comprises an acute angle that is less than 45°.

In accordance with any of the embodiments described herein, the first device comprises an expandable member.

In accordance with other embodiments, a method of manipulating tissue at a vessel includes delivering a first device and a second device percutaneously into a lumen of a vessel, using the first device to orient the second device at an angle relative to an interior wall of the vessel, and penetrate through a surface at the interior wall of the vessel at the angle using the second device.

In accordance with any of the embodiments described herein, the method further includes applying tension by a third device to the surface of the interior wall of the vessel.

In accordance with any of the embodiments described herein, the method further includes advancing the second device distally inside the interior wall of the vessel until a stopper at a proximal end of the second device engages with the vessel tissue.

In accordance with any of the embodiments described herein, the second device has a lumen, and the method further comprises delivering fluid through the lumen of the second device into a space that is inside the interior wall of the vessel.

In accordance with any of the embodiments described herein, the fluid is delivered to enlarge the space inside the interior wall of the vessel.

In accordance with any of the embodiments described herein, the second device penetrates the surface to create an opening at the interior wall of the vessel, and wherein the method further comprises increasing a size of the opening after the space inside the interior wall is enlarged.

In accordance with any of the embodiments described herein, the space is enlarged to create a flap inside the vessel.

In accordance with any of the embodiments described herein, the method further includes securing the flap relative to the vessel.

In accordance with any of the embodiments described herein, the second device penetrates the surface to create an opening at the interior wall of the vessel, and wherein the method further comprises increasing a size of the opening.

In accordance with other embodiments, a method of manipulating tissue at a vessel includes inserting a tubular structure into a first wall portion of the vessel, and using the tubular structure to deliver fluid into the first wall portion of the vessel to create a pocket inside the first wall portion of the vessel.

In accordance with any of the embodiments described herein, the fluid is delivered in pulses.

In accordance with any of the embodiments described herein, the method further includes advancing a distal end of the tubular structure distally while the distal end is inside the first wall portion of the vessel.

In accordance with any of the embodiments described herein, the method further includes delivering additional fluid into the first wall portion of the vessel after the distal end of the tubular structure has been advanced distally.

In accordance with any of the embodiments described herein, the created pocket has a length measured along a longitudinal axis of the vessel that is sufficient to form a flap from the first wall portion of the vessel.

In accordance with any of the embodiments described herein, the tubular structure comprises a distal tip and a port at the distal tip, and the fluid is delivered through the port.

In accordance with any of the embodiments described herein, the tubular structure comprises a side port, and the fluid is delivered through the side port.

In accordance with any of the embodiments described herein, the pocket is created by using the fluid to dissect a layer of tissue from the vessel.

In accordance with any of the embodiments described herein, the layer of tissue forms a flap.

In accordance with any of the embodiments described herein, the method further includes securing the flap to a second wall portion of the vessel.

In accordance with any of the embodiments described herein, the second wall portion is opposite from the first wall portion.

In accordance with any of the embodiments described herein, the tubular structure is inserted through an opening at an interior surface of the vessel, and the method comprises increasing the size of the opening.

In accordance with other embodiments, a system for manipulating tissue at a vessel includes a tubular structure sized for insertion into a first wall portion of the vessel, and a fluid source coupled to a proximal end of the tubular structure, wherein the fluid source is configured to deliver fluid into the first wall portion of the vessel to create a pocket inside the first wall portion of the vessel, and wherein the fluid source is configured to deliver the fluid with a fluid pressure that is strong enough to dissect tissue in the first wall portion of the vessel, but insufficient to puncture through the first wall portion.

In accordance with any of the embodiments described herein, the fluid delivery device is configured to deliver the fluid in pulses.

In accordance with any of the embodiments described herein, the tubular structure comprises a distal tip and a port at the distal tip.

In accordance with any of the embodiments described herein, the tubular structure comprises a side port.

In accordance with any of the embodiments described herein, the system further includes a guide member coupled to the tubular structure.

In accordance with any of the embodiments described herein, the guide device comprises an elongated structure having a blunt distal tip.

In accordance with any of the embodiments described herein, the elongated structure and the tubular structure are coupled together to form a stopper.

In accordance with any of the embodiments described herein, the blunt distal tip of the elongated structure is distal to a distal tip of the tubular structure.

In accordance with any of the embodiments described herein, the system further includes securing mechanism for securing a part of the first wall portion to a second wall portion of the vessel.

In accordance with any of the embodiments described herein, the second wall portion is opposite from the first wall portion.

In accordance with some embodiments, a method of manipulating tissue at a vessel includes advancing a device distally relative to an opening at an interior surface of the vessel, and into a first wall portion of a vessel until an entirety of the device is within the wall of the vessel, the device having a distal end, a proximal end, and a cutting element coupled to the proximal end, and using the cutting element to increase a size of the opening by retracting the device proximally.

In accordance with any of the embodiments described herein, the device comprises an expandable member.

In accordance with any of the embodiments described herein, the expandable member comprises an inflatable member.

In accordance with any of the embodiments described herein, the expandable member comprises a cage.

In accordance with any of the embodiments described herein, the cutting element comprises a blade.

In accordance with any of the embodiments described herein, the method further includes creating the opening before the entirety of the device is inserted into the first wall portion of the vessel.

In accordance with any of the embodiments described herein, the method further includes creating the opening using the device.

In accordance with any of the embodiments described herein, the method further includes using the device to create a flap from a portion of the vessel, wherein the increased size of the opening results in the flap having a desired width.

In accordance with any of the embodiments described herein, the method further includes securing one end of the flap relative to a second wall portion of the vessel.

In accordance with any of the embodiments described herein, the second wall portion is opposite from the first wall portion.

In accordance with other embodiments, a system for manipulating tissue at a vessel includes a tissue separator sized for insertion into a first wall portion of a vessel through an opening at an interior surface of the vessel, the tissue separator having a distal end, a proximal end, and a cutting element coupled to the proximal end, wherein the cutting element is configured to increase a size of the opening.

In accordance with any of the embodiments described herein, the tissue separator comprises an expandable member.

In accordance with any of the embodiments described herein, the expandable member comprises an inflatable member.

In accordance with any of the embodiments described herein, the expandable member comprises a cage.

In accordance with any of the embodiments described herein, the expandable member, when expanded, has a shape and size configured to create a flap from the first wall portion of the vessel.

In accordance with any of the embodiments described herein, the expandable member has an asymmetric configuration.

In accordance with any of the embodiments described herein, the system further includes securing device for securing one end of the flap relative to a second wall portion of the vessel.

In accordance with any of the embodiments described herein, the second wall portion is opposite from the first wall portion.

In accordance with any of the embodiments described herein, the cutting element comprises a blade.

In accordance with any of the embodiments described herein, the system further includes a device for creating the opening before the tissue separator is inserted into the first wall portion of the vessel.

In accordance with any of the embodiments described herein, the device is coupled to the tissue separator.

In accordance with any of the embodiments described herein, the device is separate from the tissue separator.

In accordance with other embodiments, a method of manipulating tissue at a vessel includes inserting a device percutaneously into a lumen of a vessel, advancing the device inside the lumen of the vessel until the device reaches a location in the vessel that has a flap, and using the device to secure the flap relative to an interior surface of the vessel.

In accordance with any of the embodiments described herein, the device comprises a stitching material, and the act of using the device to secure the flap comprises using the stitching material to secure the flap relative to the interior surface of the vessel.

In accordance with any of the embodiments described herein, the device comprises a pin, and the act of using the device to secure the flap comprises using the pin to secure the flap relative to the interior surface of the vessel.

In accordance with any of the embodiments described herein, the device comprises tissue glue.

In accordance with any of the embodiments described herein, the flap is located on a first side of the vessel, and the interior surface is located on a second side of the vessel that is opposite from the first side.

In accordance with any of the embodiments described herein, the method further includes moving the flap from the first side of the vessel towards the second side of the vessel.

In accordance with any of the embodiments described herein, the flap has an end that is separated from the vessel, the end of the flap located at a first position along the vessel, and wherein the flap is moved to reach the second side of the vessel, the end of the flap is located at a second position along the vessel that is offset from the first position.

In accordance with any of the embodiments described herein, the flap is created from a portion of the vessel, and has a first end that is separated from the vessel, and a second end that extends from the vessel.

In accordance with any of the embodiments described herein, the method further includes inserting a cutting device percutaneously into the lumen of the vessel, and using the cutting device in a process to create the flap from a portion of the vessel.

In accordance with any of the embodiments described herein, the act of using the cutting device comprises placing the cutting device inside a wall of the vessel.

In accordance with any of the embodiments described herein, the cutting device comprises a blade.

In accordance with any of the embodiments described herein, the cutting device comprises a tube for delivering fluid.

In accordance with any of the embodiments described herein, the interior surface comprises another flap.

In accordance with other embodiments, a system for manipulating tissue at a vessel includes a first device having an elongated configuration, and carrying a securing mechanism, wherein the first device is sized for insertion into a lumen of a vessel, and wherein the securing mechanism is configured to secure a flap in the vessel relative to an interior surface of the vessel.

In accordance with any of the embodiments described herein, the securing mechanism comprises a stitching material.

In accordance with any of the embodiments described herein, the securing mechanism comprises a pin.

In accordance with any of the embodiments described herein, the securing mechanism comprises tissue glue.

In accordance with any of the embodiments described herein, the flap is located on a first side of the vessel, and the interior surface is located on a second side of the vessel that is opposite from the first side, and wherein the system further comprising a positioning mechanism for moving the flap from the first side of the vessel towards the second side of the vessel.

In accordance with any of the embodiments described herein, the flap has an end that is separated from the vessel, the end of the flap located at a first position along the vessel, and wherein the positioning mechanism is configured to move the flap so that when the flap reaches the second side of the vessel, the end of the flap is located at a second position along the vessel that is offset from the first position.

In accordance with any of the embodiments described herein, the system further includes a cutting device sized for insertion into the lumen of the vessel, wherein the cutting device is configured to penetrate into a wall of the vessel.

In accordance with any of the embodiments described herein, the cutting device comprises a blade.

In accordance with any of the embodiments described herein, the cutting device comprises a tube for delivering fluid.

In accordance with any of the embodiments described herein, the cutting device is configured to create the flap from a portion of the vessel.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIGS. 1-6 illustrate components of a valve creation system in accordance with some embodiments.

FIGS. 30-37 illustrate different tissue layer separation mechanisms that involve a dissection probe in accordance with different embodiments.

FIG. 38 illustrates a probe with suction capability in accordance with some embodiments.

FIG. 40 illustrates a conduit mechanism that includes a stitching mechanism in accordance with some embodiments.

FIG. 41 illustrates a lip grabbing mechanism in accordance with some embodiments.

FIG. 44 illustrates a dissection probe with an actuatable portion in accordance with other embodiments.

FIG. 45 illustrates a dissection probe exiting from a guide member in accordance with some embodiments.

FIG. 46 illustrates a dissection probe that is configured to oscillate in accordance with some embodiments.

FIG. 47 illustrates a dissection probe that is configured to move in a lateral direction in accordance with some embodiments.

FIG. 53 illustrates a sub-intimal access mechanism that includes sharp edges in accordance with some embodiments.

FIGS. 56a-56f illustrate another autologous valve creation system, and a method of using such system in accordance with other embodiments.

DETAILED DESCRIPTION

Figure 1:
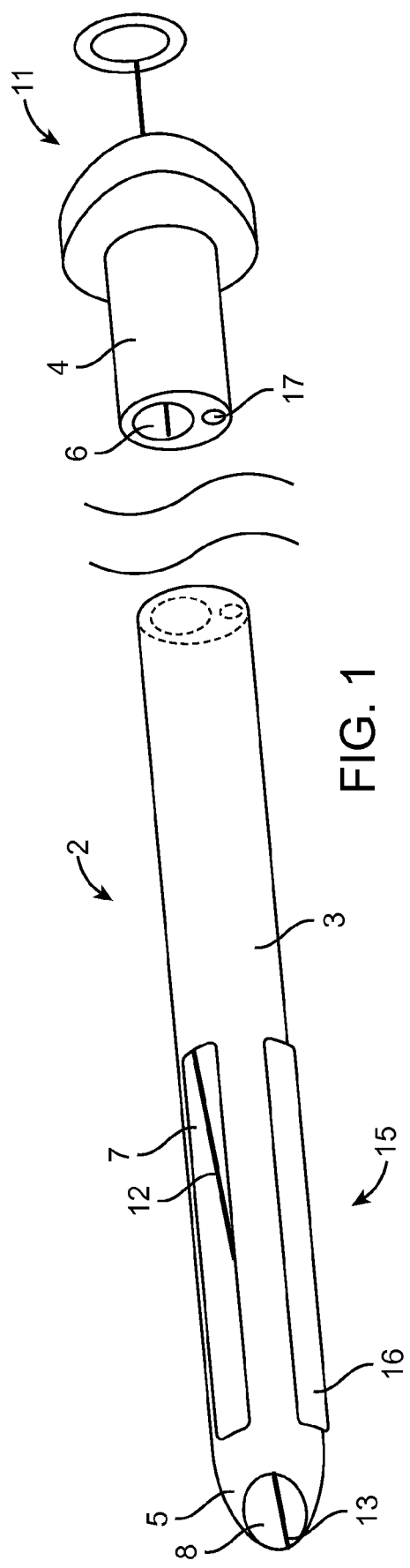

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIGS. 1-6 illustrate components of a valve creation system in accordance with some embodiments. The valve creation system includes a conduit mechanism 2 (FIGS. 1, 2), a sub-intimal access mechanism 18 (FIGS. 3a, 3b), and a sub-intimal pocket creation mechanism 32 (FIGS. 4a, 4b). In some embodiments, the sub-intimal pocket creation mechanism 32 may optionally include an intimal separation mechanism 46 (FIGS. 5a, 5b). Also, in some embodiments, the sub-intimal pocket creation mechanism 32 may optionally include a valve securement mechanism 48 (FIG. 6).

FIG. 1 illustrates a conduit mechanism 2 in accordance with some embodiments. As used in this specification, the term "conduit mechanism" or similar terms refer to any device that provides a conduit, channel, or lumen for housing and/or delivering a component or a substance. The conduit mechanism 2 serves as a platform to support other device components, which can be inserted percutaneously into bodily lumen(s). The conduit mechanism 2 includes an elongated tube 3 with a proximal end 4 and a distal end 5. The conduit mechanism 2 has an internal lumen 6, which extends from the proximal end 4 to the distal end 5 of the elongated tube 3, terminating at a sideway facing exit port 7 near, but some small distance (e.g. 2 mm-10 mm) away from, the distal end 5 of the elongated tube 3. The conduit mechanism 2 also includes a distal exit port 8 located at the distal most tip of the elongated tube 3, wherein the port 8 is in fluid communication with the internal lumen 6.

Figure 2:
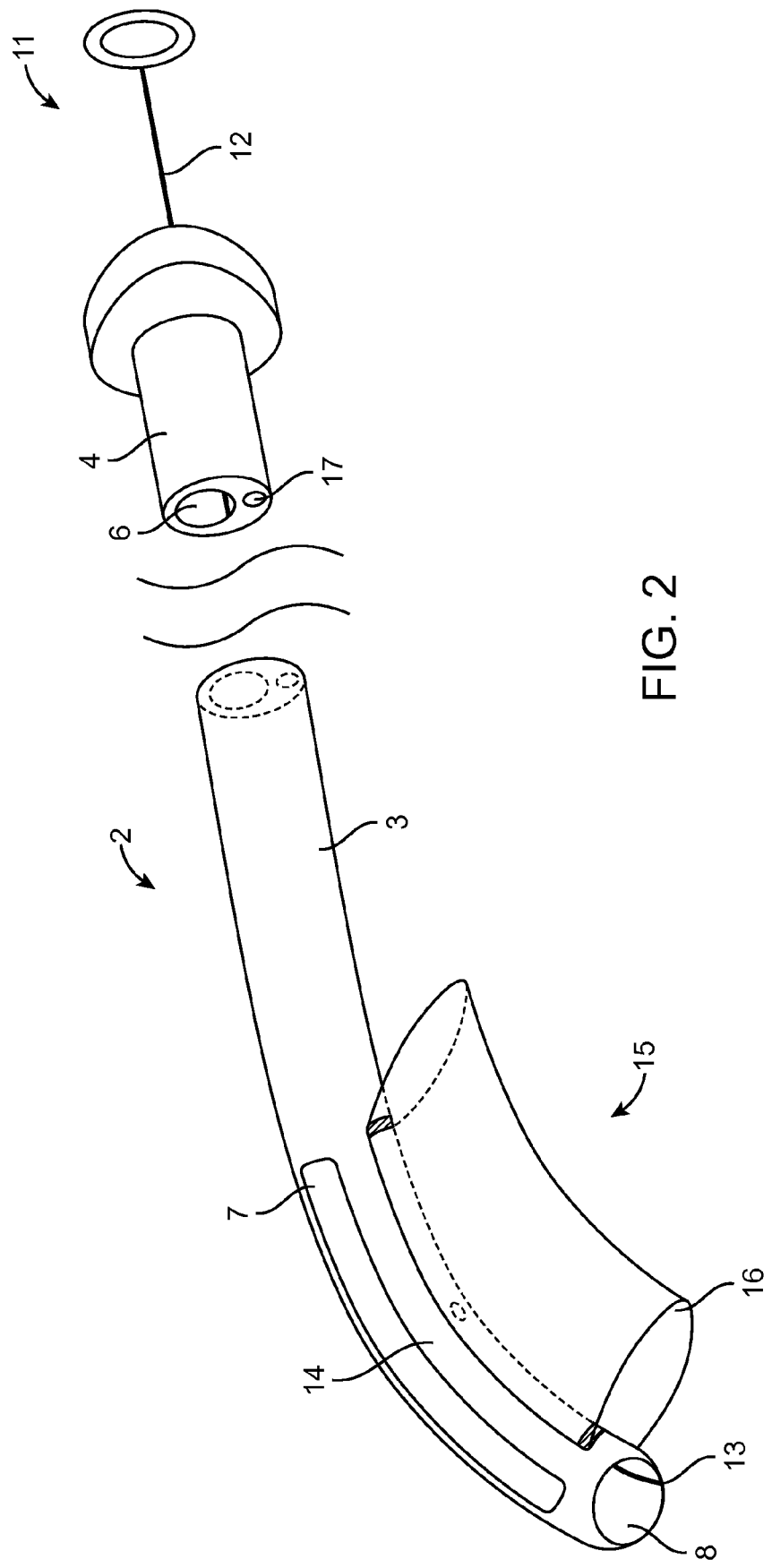

The conduit mechanism 2 also includes an angling mechanism 11. In this embodiment, the angling mechanism 11 takes the form of a wire 12 connected with a mechanical bond 13 to the distal-most end of the internal lumen 6 of the conduit 2. In this embodiment, the angling mechanism 11 extends through the internal lumen 6 and past the proximal end 4 of the conduit 2. In this embodiment, the stiffness of the elongated tube 3 is lower at the distal end than at the proximal end so that when the wire 12 of the angling mechanism 11 is put into tension by the user at the proximal end, the elongated tube forms a curvature 14 near its distal end. Anyone skilled in the art of steerable catheters should understand how this mechanism can be used to create a curvature for the elongated tube 3. This curvature will allow tools to be passed through the sideway facing exit port 7 to take a non-parallel angle relative to the lumen wall, facilitating autologous valve creation. FIG. 1 depicts the conduit mechanism 2 in a straight orientation before actuation of the angling mechanism 11, while FIG. 2 depicts the conduit mechanism 2 in a curved orientation due to the actuation of the angling mechanism 11.

In the illustrated embodiments, the conduit mechanism 2 also includes a wall-tensioning mechanism 15. As used in this specification, the term "wall-tensioning mechanism" or similar terms refer to any device that is configured to apply tension at a wall of a vessel. The wall-tensioning mechanism 15 includes a sideway-facing, inflatable, compliant balloon 16 of nearly cylindrical shape. The balloon 16 is coupled to the elongated tube 3 near the distal end 5 of the elongated tube 3. The balloon is in fluid communication with an inflation lumen 17, which communicates with an inflation port at the proximal end 4 of the elongated tube 3. The inflatable balloon 16 can be inflated to multiple diameters depending on the quantity and pressure of inflation fluid supplied through the inflation lumen 17. FIG. 1 depicts a non-actuated wall-tensioning mechanism 15 with a deflated balloon 16, while FIG. 2 depicts the wall-tensioning mechanism 15 in its actuated orientation with an inflated balloon 16. The balloon 16 is configured (e.g., sized, shaped, etc.) to be placed in a vessel. When expanded, the balloon 16 applies a tension at the wall of the vessel.

Figure 3A:
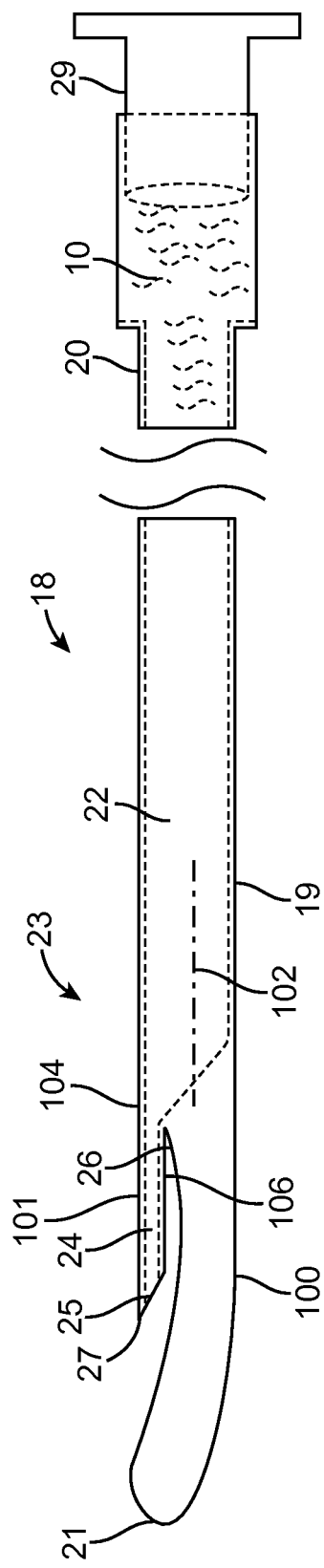

FIG. 3a depicts a sub-intimal access mechanism 18 in accordance with some embodiments. As used in this specification, the term "sub-intimal access mechanism" or similar terms refer to any device, wherein at least a portion of which is configured to be placed inside a wall of a vessel. The sub-intimal access mechanism 18 may be used with the conduit mechanism 2 of FIGS. 1 and 2. In particular, the sub-intimal access mechanism 18 may be introduced through the lumen 6 of the conduit mechanism 2, and out of the sideway facing exit port 7.

In the illustrated embodiments, the sub-intimal access mechanism 18 includes an elongated member 19 with a proximal end 20, a guide member 100 having a closed blunt distal end 21, an internal lumen 22, and a tissue engagement mechanism 23 extending from the elongated tube 19 at a location a small distance (e.g. 2 mm-8 mm) proximal to the closed blunt distal end 21. In this depiction, the tissue engagement mechanism 23 includes a tubular structure 101 with a lumen 24 in fluid communication with the main lumen 22 of the sub-intimal access mechanism 18. There is therefore fluid communication from the proximal end 20 of the sub-intimal access mechanism 18 through the entire length of the main lumen 22 of the sub-intimal access mechanism 18, into the lumen 24 of the tissue engagement mechanism 23, terminating distally at a forward facing exit port 25. In some embodiments, the tissue engagement mechanism 23 forms a relative angle with the elongated tube 19 of the sub-intimal access mechanism 18. The intersection of the tissue engagement mechanism 23 and the body of the elongated tube 19 creates a bottoming-out mechanism 26, in the form of an elbow joint.

In some embodiments, the tissue engagement mechanism 23 may be attached to the elongated tube 19. In other embodiments, the tissue engagement mechanism 23 and the elongated tube 19 may be formed together in an unity configuration. For example, the tissue engagement mechanism 23 may be a part of the elongated tube 19. The tissue engagement mechanism 23 has a sharpened tip 27, to facilitate penetration of an interior wall of a blood vessel. The angular orientation of the bevel of the sharpened tip 27 is such that the distal most point of the bevel is oriented furthest away from a longitudinal axis 102 of the sub-intimal access mechanism 18. In particular, the distal profile of the tip 27 tapers proximally from a first side 104 to a second side 106, wherein the first side 104 is further away from the axis 102 than the second side 106. Such configuration is advantageous because it allows the tip 27 to penetrate into the vessel wall more easily.

Figure 3B:
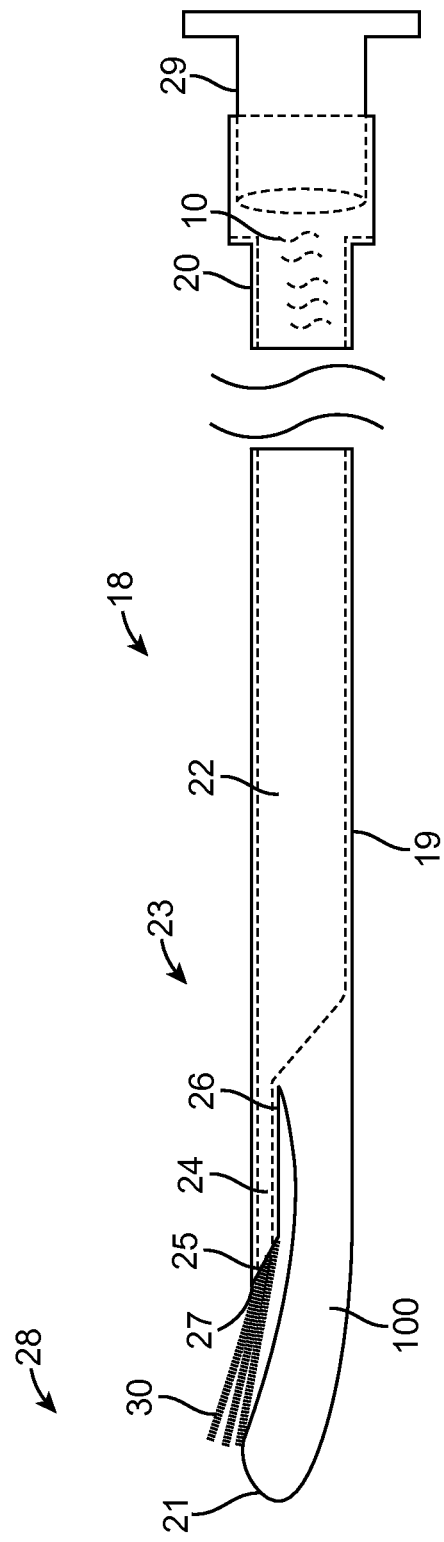

The sub-intimal access mechanism 18 also includes a tissue layer separation mechanism 28. As used in this specification, the term "tissue layer separation mechanism" or similar terms refer to any mechanism that is capable of separating tissue (e.g., dissecting tissue). The tissue layer separation mechanism 28 includes a pressurized source of fluoroscopic contrast agent 10, and a tissue layer separation actuator 29. FIG. 3a depicts the tissue layer separation mechanism 28 prior to actuation, at which point the pressurized source of fluoroscopic contrast agent 10 exists at the proximal end 20 of the sub-intimal access mechanism 18. FIG. 3b depicts the utilization of the tissue layer separation mechanism 28 during actuation, at which point the pressurized source of fluoroscopic contrast agent 10 is forced through the main lumen 22 of the sub-intimal access mechanism 18, and through the lumen 24 of the tissue engagement mechanism 23, until it exits out of the forward facing exit port 25 as a high pressurized stream 30. The tissue layer separation actuator 29 is a manually controlled piston mechanism or syringe. The stream of high-pressure fluid 30 can be used to separate layers of a wall of a vessel by forcing its way between tissue layers, creating a semi-controlled hydrodissection (not depicted here). In some embodiments, the bolus of high-pressure fluid that that is expelled into the inter-layer dissection plane in the vessel is sustained for 3-4 seconds. In the illustrated embodiments, the fluid stream 30 provides a fluid pressure inside the vessel wall that is sufficient to dissect tissue in the vessel wall, but insufficient to puncture through the wall of the vessel. The fluid stream 30 may have a fluid pressure anywhere from 100 mmhg to 1000 mmhg. Also, in some embodiments, the fluid stream 30 may be in pulses.

In some embodiments, the agent 10 may be a contrast agent, which may be imaged using an imaging device, such as a fluosorcopic device. This allows the position of the device 18 to be determined, and the fluid path of the agent 10 to be visualized during delivery of the agent 10. This also allows the progress of the separation of the tissue layers in the vessel to be monitored.

The distal tip 21 of the guide member 100 is configured to be placed on a surface at an interior wall of the vessel to thereby guide the positioning (e.g., orientation) of the tip 27 relative to the vessel wall surface. In some cases, pressure may be applied to the vessel wall surface by pushing the blunt tip 21 distally, which will apply tension to the wall surface, and/or change an orientation of the wall surface—either or both of which will allow the tip 27 to more easily penetrate into the wall of the vessel.

In some embodiments, the tissue layer separation mechanism 28 is configured to dissect tissue in the wall of the vessel to create a pocket inside the wall of the vessel having a size that is sufficient to form a flap at the vessel wall. In such cases, the fluid stream 30 functions as a sub-intimal pocket creation mechanism. In other embodiments, the tissue layer separation mechanism 28 is configured to deliver the fluid stream 30 to create an initial lumen in the wall of the vessel, and another device may be placed in the lumen to expand the size of the lumen to create a pocket that is large enough to form a flap at the vessel wall. FIG. 4a depicts a sub-intimal pocket creation mechanism 32 in accordance with some embodiments. As used in this specification, the term "sub-intimal pocket creation mechanism" or similar terms refer to any mechanism that is configured to create a pocket inside a wall of a vessel. The sub-intimal pocket creation mechanism 32 has an elongated member 33, with a proximal end 34, a blunt, tapered distal end 35, and a contrast lumen 36, which extends from the proximal end 34 to a contrast exit port 37 at the distal end 35 of the mechanism 32. The sub-intimal pocket creation mechanism 32 also includes an inflatable, compliant pocket creation balloon 38, a balloon inflation lumen 39, and an inflation port 40, which connects the balloon inflation lumen 39 to the pocket creation balloon 38. In the illustrated embodiments, the pocket creation balloon 38 is bonded to the outer surface 33 of the sub-intimal pocket creation mechanism 32 to form an air-tight seal.

FIG. 4b depicts a configuration of the mechanism 32, in which the pocket creation balloon 38 is inflated. In the illustrated embodiments, the inflated balloon 38 takes an asymmetric shape upon inflation through the inflation lumen 39, which inflates sideways off of the outer surface of the sub-intimal pocket creation mechanism 32. The pocket creation balloon's largest diameter 41 is some distance closer to the proximal end 42 of the balloon than to the distal end 43 of the balloon. The balloon has a curved distal taper 44 and a curved proximal taper 45, the proximal one being more abrupt. In this embodiment, the sub-intimal pocket mechanism 32 is sized appropriately in its deflated orientation such that it has dimensional clearance through the main lumen 22 of the sub-intimal access mechanism 18, the narrow lumen 24 of the tissue engagement mechanism 23, as well as the forward facing exit port 25.

In some embodiments, the sub-intimal pocket mechanism 32 may optionally further include an intimal separation mechanism 46 that is configured to increase a size of an opening at a surface of a vessel wall (FIG. 5a). As used in this specification, the term "intimal separation mechanism" or similar terms refer to a mechanism for finalizing intimal separation at the top lip of the valve (such as, a mechanism for providing a desired width at the top lip of a flap). In this embodiment, the intimal separation mechanism 46 includes a backward facing cutting mechanism 47, depicted in this embodiment as a thin wire. The cutting mechanism 47 is bonded to the surface 33 of the elongated member 33, just proximal to the pocket creation balloon 38. In this embodiment, the cutting mechanism 47 is bonded such that expansion of the pocket creation balloon 38 will move the cutting mechanism 47 into its operative position, and will force the cutting mechanism 47 into contact with tissue. FIG. 5b shows a depiction of the intimal separation mechanism 46, in which the cutting mechanism 47 assumes an expanded shape upon inflation of the pocket creation balloon 38. In other embodiments, instead of being secured to the elongated member 33, the cutting mechanism 47 may be secured to the balloon 38. Also, in any of the embodiments described herein, the cutting mechanism 47 may include a plurality of sharp particles that is disposed on the surface of the balloon 38.

Figure 6E:
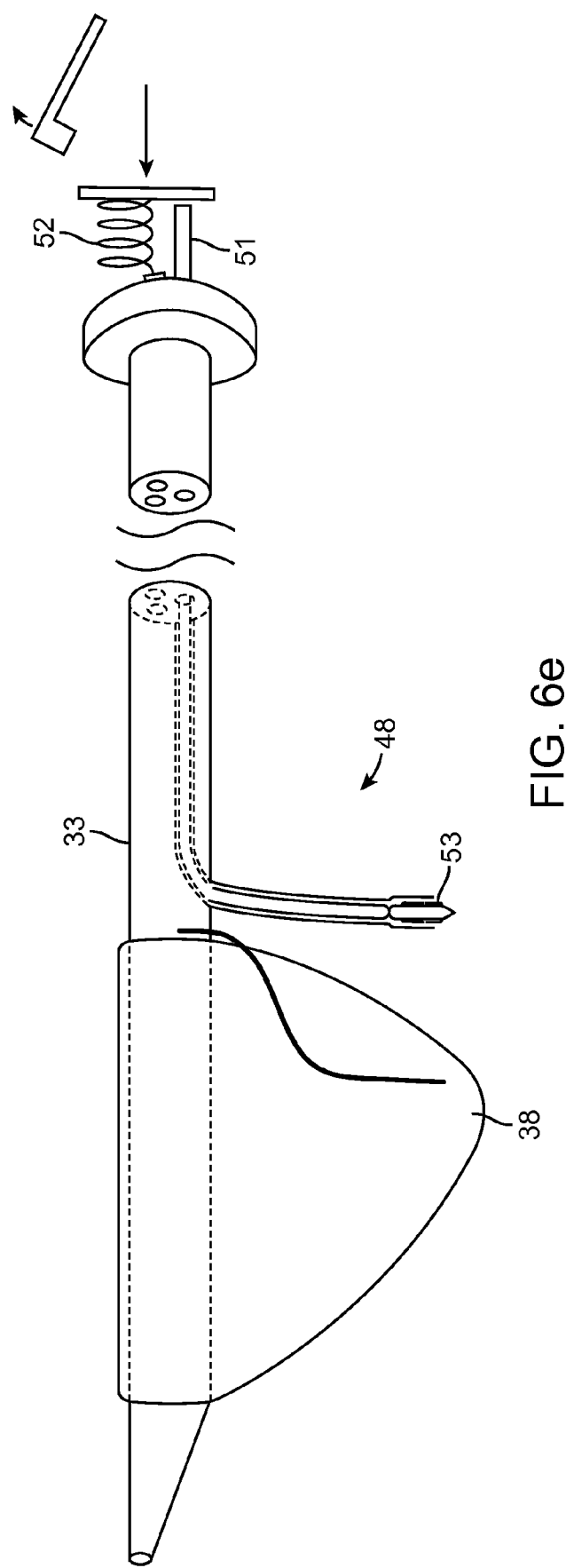

In some embodiments, the sub-intimal pocket mechanism 32 may optionally further include a channel for delivering a valve securement mechanism, wherein the valve securement mechanism is configured to secure a flap against a wall of a vessel. FIG. 6a illustrates a channel 49 located within the elongated member 33 of the mechanism 32, which is for delivering a valve securement mechanism. FIG. 6b depicts a valve securement mechanism 48 in accordance with some embodiments, particularly showing the valve securement mechanism 48 being delivered inside the channel 49. FIG. 6d depicts a more detailed view of the distal end 53 of the securement mechanism 48, which is comprised of a sharp puncturing member 54 at the leading end, two nitinol distal clip arms 55, two nitinol proximal clip arms 56, a constraining sheath 57, and a detachment joint 58, which is located at the interface between the securement delivery system 51 and the securement mechanism distal tip 53. In this depiction, the detachment joint 58 is shown as a notch in the wire. Returning to FIG. 6b, which depicts the securement delivery system 51 as a wire, and an actuation mechanism 52, depicted as a spring and latch system. In the illustrated embodiments, the channel 49 extends from the proximal end of the sub-intimal pocket creation mechanism 32 to an angled side port 50, through which valve securement will be accomplished. FIG. 6c depicts the valve securement mechanism 48 in its initial stage of deployment, in which the delivery system 51 has moved forward pushing the securement mechanism distal tip 53 out of the angled side port 50 by a short distance. FIG. 6e depicts the valve securement mechanism 48 in its second stage of actuation, as a result of activation of the actuation mechanism 52. In this embodiment, the activation of the actuation mechanism 52 occurs after inflation of the pocket creation balloon 38. The delivery system has moved forward to its maximum distance, pushing the securement mechanism distal tip 53 to a distance from the elongated member 33 slightly exceeding that of the outer most portion of the inflated pocket creation balloon 38. FIG. 6f depicts the valve securement mechanism 48 in its third stage of actuation, in an orientation in which the constraining sheath 57 has been retracted enough to allow the distal clip arms 55 to spring outward into an orientation perpendicular to the axis of the delivery system 51 as a result of their shape memory characteristics. The forth stage of actuation is accomplished when the constraining sheath 57 is retracted further to allow the proximal clip arms 56 to spring outward into a orientation perpendicular to the axis of the delivery system 51 as a result of their shape memory characteristics. FIG. 6g depicts the valve securement mechanism 48 in its fifth and final stage of actuation. After the valve securement mechanism 48 has been deployed to secure a flap against a vessel wall, the entire securement mechanism delivery system 51 is retracted forcing the securement mechanism distal tip 53 to detach from the securement mechanism delivery system 51 at the detachment joint 58. The detachment joint 58 is intentionally built to fail in tension at that location, so that the securement mechanism distal tip 53 is left behind upon retraction of the securement mechanism delivery system 51. In this embodiment, the securement mechanism distal tip 53 takes the final orientation of an "H-tag". In other embodiments, the securement mechanism distal tip 53 may have other configurations (e.g., shapes). For example, in other embodiments, the securement mechanism may include one or more tines having different deployed shapes. Also, in other embodiments, instead of the above configurations, the securement mechanism 48 may be tissue glue that is deployed out of the channel 49, or another channel that is at a different device. The tissue glue is used to secure a flap against a vessel wall.

FIGS. 7-12 depict a method of using the above-described devices within the context of a percutaneous valve creation procedure. The described functionality is by no means intended to be descriptive of all possible uses of the devices. It should be noted that one or more acts/functionalities may be omitted for certain procedural situations.

FIGS. 7-12 portray the devices being used within a bodily lumen 59 of a vessel. For simplicity, the bodily lumen is shown with an inner layer 60, and an outer layer 61. In many bodily lumens, such as the vein, the lumen wall is composed of three layers: the intima, media, and adventitia. In the following representations, the inner layer 60 may represent the intima and the media combined, while the outer layer 61 may represent the adventitia. Alternatively, in some embodiments of valve creation, the inner layer 60 may represent the intima, while the outer layer 61 may represent the media and the adventitia combined. In still further embodiments, both the inner layer 60 and the outer layer 61 may include the media.

Figure 7:
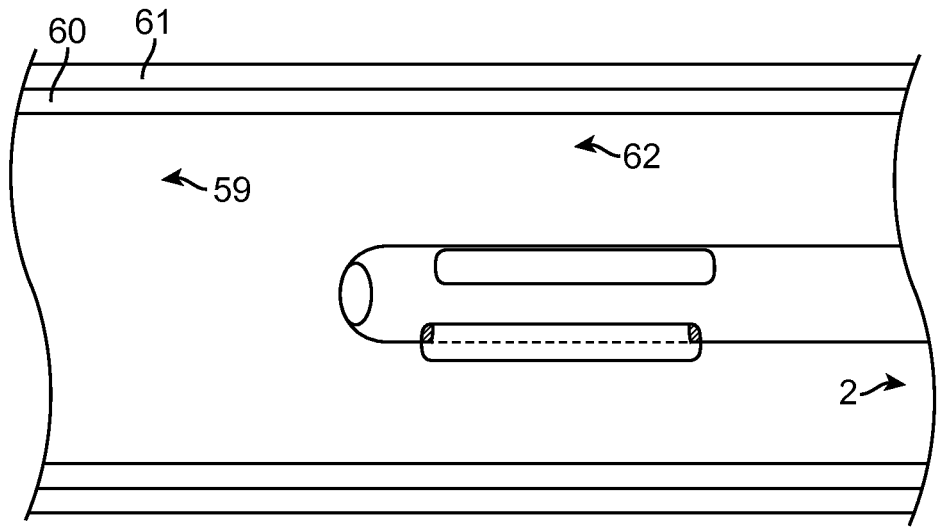
FIGS. 7-12 illustrate a method of creating a valve in accordance with some embodiments.

FIG. 7 depicts the conduit mechanism 2 of FIG. 1, which has been inserted percutaneously and delivered to the valve creation site 62 within a bodily lumen 59, from the retrograde direction. In some embodiments, the user of the device may inject a fluoroscopic contrast agent 10 through the distal exit port of the conduit mechanism 8, so that fluoroscopic visualization may be utilized to view the conduit mechanism 2. This may allow the user to determine the position of the conduit mechanism 2 relative to the valve creation site 62.

Figure 8A:
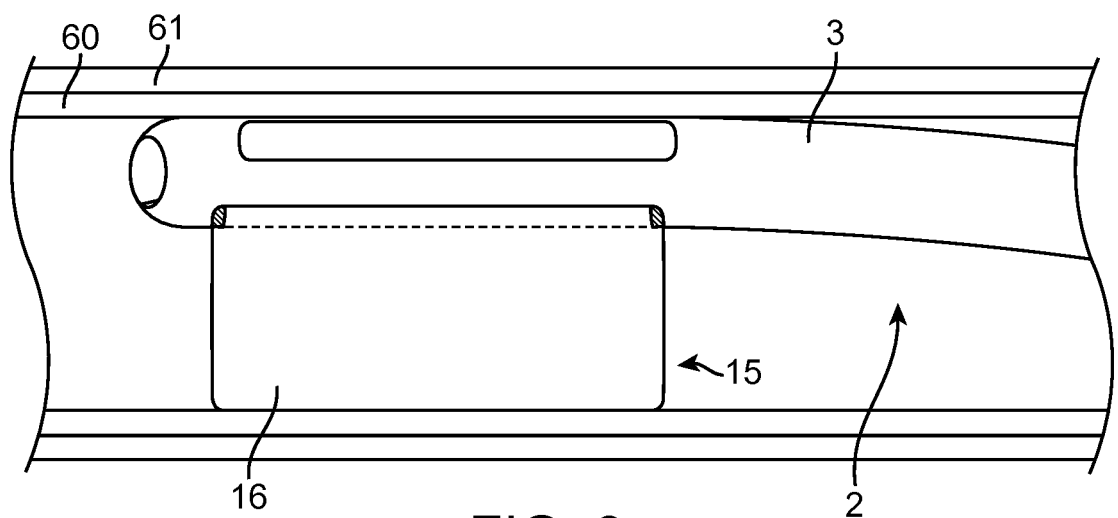

FIG. 8a depicts the conduit mechanism 2, in which the wall-tensioning mechanism 15 has been actuated. In this depiction, the main functional component of the wall-tensioning mechanism 15 is an inflatable compliant balloon 16, which extends perpendicularly from the surface 3 of the conduit mechanism 2 to the inner wall 60 of the bodily lumen 59. The balloon is inflated through the inflation lumen 17 incrementally until a particular pressure is measured which corresponds with proper lumen wall dilation.

Figure 8B:
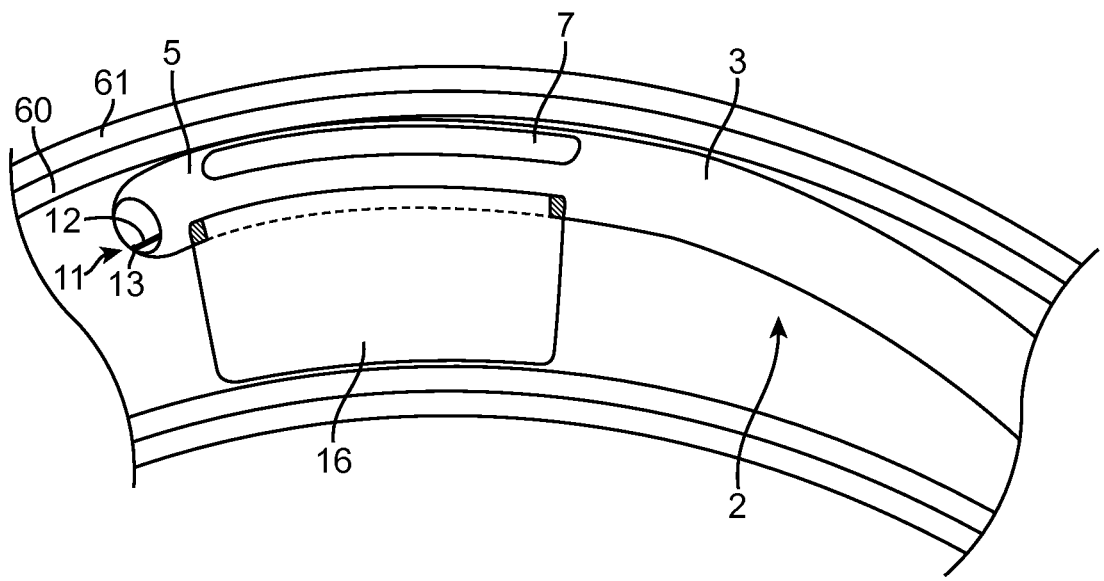

FIG. 8b depicts the conduit mechanism 2, in which the angling mechanism 11 has been actuated. In this depiction, the main functional component of the angling mechanism 11 is a wire 12, which is attached to a mechanical bond 13 to the distal-most end of the internal lumen 6 of the conduit mechanism 2. In this depiction, the wire 12 has been tensioned from the proximal end, which forces the distal end 5 of the conduit mechanism 2, into a bent orientation. With the wall-tensioning mechanism 15 actuated, the catheter surface 3 and the inflated balloon 16 are in flush contact with the inner lumen wall 60, and thus transfer their curved orientation to the bodily lumen 59 itself. In this way, the angling mechanism 11, forces the wall of the vessel to bend. In the illustrated embodiments, the majority of the curvature of the conduit mechanism 2 occurs at or distal to the sideways facing exit port 7. This configuration is advantageous because it allows a tool passing out of the sideways facing exit port 7 to form a non-parallel angle with the wall of the vessel.

Figure 9A:
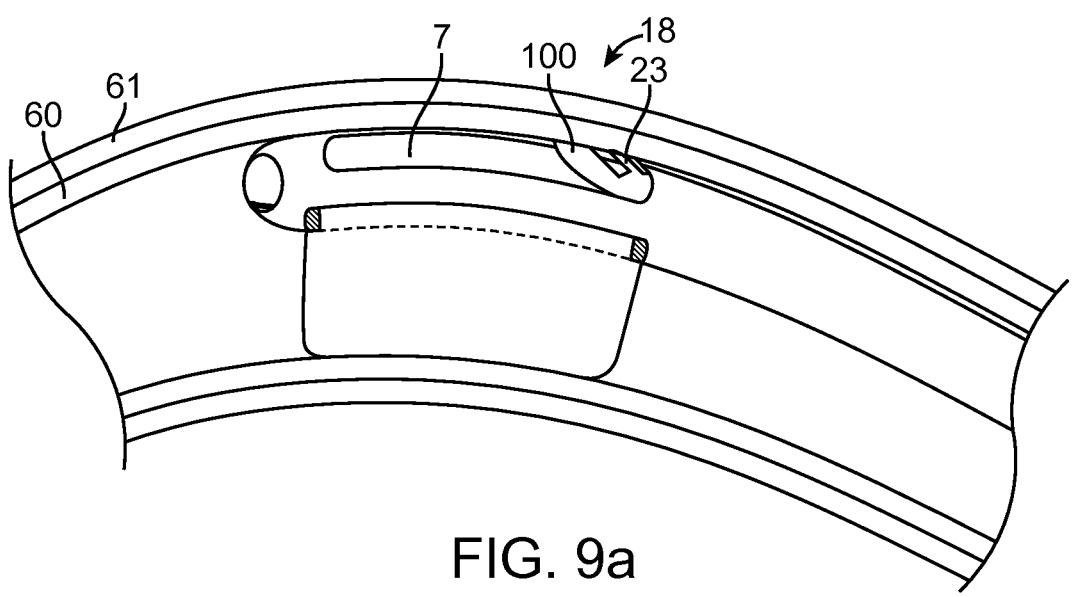
Figure 9B:
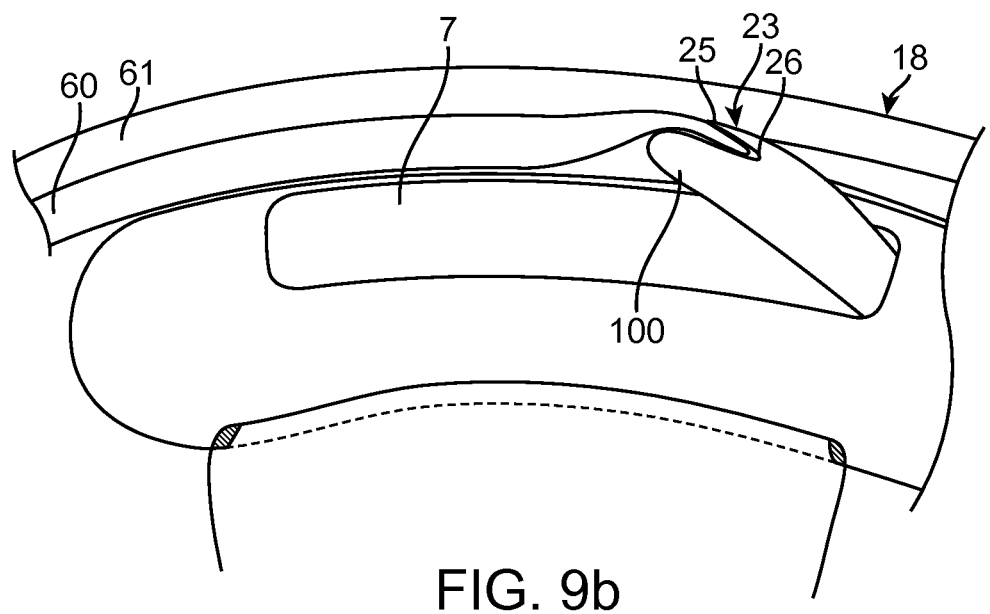

FIGS. 9a-9b depict the sub-intimal access mechanism 18 located in the conduit mechanism 2, and being deployed therefrom. FIG. 9a depicts the sub-intimal access mechanism 18 during actuation as it exits the sideways facing exit port 7, as a result of advancement from the proximal end of the conduit 4. Due to the curvature of the conduit distal to the sideways facing exit port 7, the sub-intimal access mechanism 18 exits the conduit at a non-parallel angle relative to the inner lumen wall 60. The guide member 100 is pressed against the vessel surface to guide the positioning of the tissue engagement mechanism 23. For example, the mechanism 23 may be tilted about the contact point between the guide member 100 and the vessel wall. Thus, the guide member 100 allows the mechanism 23 to enter the vessel wall at a desired angle. In some cases, the guide member 100 also provides some tension at the vessel wall surface (i.e., in addition to that already provided by the balloon 16). FIG. 9*b* depicts the sub-intimal access mechanism 18 after it has been advanced fully and has engaged the inner lumen wall 60. In the illustrated embodiments, the tissue engagement mechanism 23 penetrates the vessel wall, and is advanced until vessel tissue abuts against a stopper (e.g., the region where the proximal end of the tissue engagement mechanism 23 meets the guide member 100). Full engagement occurs after the tissue engagement mechanism 23 penetrates the vessel wall, and when the tissue between the guide member 100 and the mechanism 23 meets the elbow joint of the bottoming-out mechanism 26 (the stopper). Upon full tissue engagement, the forward facing exit port 25 of the tissue engagement mechanism 23 rests completely within the lumen wall.

Figure 10:
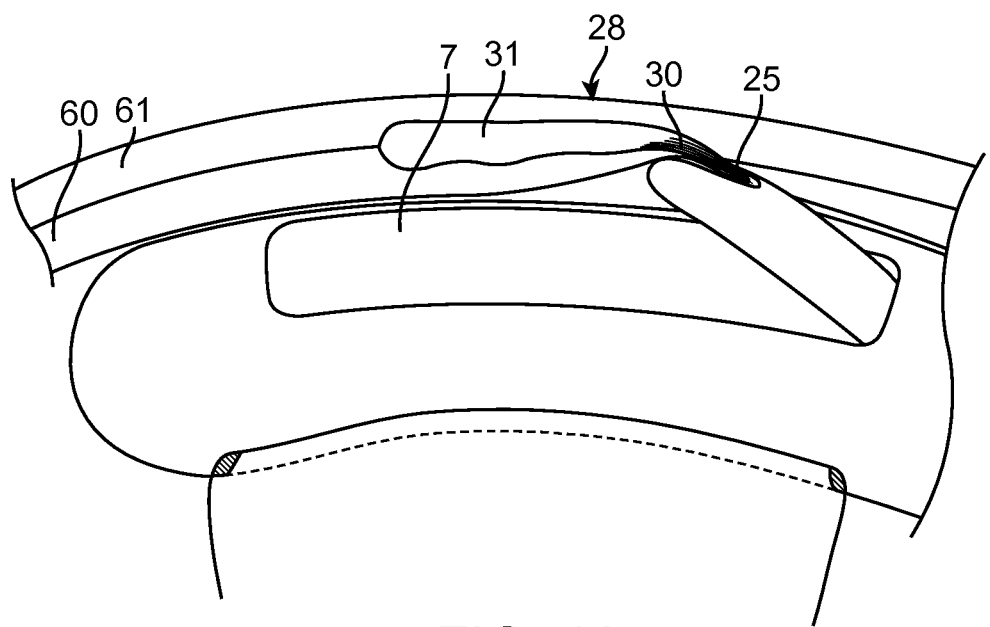

FIG. 10 depicts the tissue layer separation mechanism 28 being used at the valve creation site 62. After the tip 27 of the tissue engagement mechanism 23 has been placed inside the wall of the vessel, the pressurized source of fluoroscopic contrast agent 10 is forced through the main lumen 22 of the sub-intimal access mechanism 18, and through the narrow lumen 24 of the tissue engagement mechanism 23, until it exits out of the forward facing exit port 25 as a high pressure stream 30. This stream of high-pressure fluid 30 acts to atraumatically separate the inner layer 60 from the outer layer 61 of the bodily lumen 59 at the valve creation site 62 by physically breaking interlayer bonds upon injection, creating a semi-controlled, inter-layer dissection plane 31. In some embodiments, the pressure of the stream 30 is sustained until the dissection plane 31 with a certain length has been created. In other embodiments, the stream 30 may be delivered in pulses. Also, in other embodiments, the pressure of the stream 30 may be adjusted (e.g., increased) as the length of the dissection plane 31 is increasing in size. High-pressure fluid dissection offers advantages over blund mechanical dissection with a stiff probe. The dissection force imparted within the vessel wall is spread out over the internal surface area of the dissection pocket, and thus imparts less force in any one location than would a solid probe (or a solid device). Additionally, with fluid dissection, tissue separation automatically occurs along a plane of least-resistance, which may allow dissection to take place at a lower pressure (e.g., compared to using a solid device).

Because a fluoroscopic contrast agent 10 is used in tissue layer separation in this embodiment, the user will have the opportunity to visualize the effect of the fluid delivery on the tissue using fluoroscopic visualization techniques. In particular, through fluoroscopic visualization technique, the user may view the progress of the tissue dissection within the wall of the vessel. The fluoroscopic visualization technique also allows a user to determine if the dissection plane 31 is getting too close to the exterior surface of the vessel wall. In such cases, the user may determine that there is a potential that the vessel wall may be punctured (by the fluid) therethrough, and may stop the process. Additionally, this visualization technique allows the user to evaluate the depth and shape of the newly created inter-layer plane 31 to determine if the tissue layer separation mechanism 28 needs to be actuated again. This process may be repeated indefinitely until a proper tissue layer separation has occurred, which allows for continuation of the procedure.

Figure 11A:
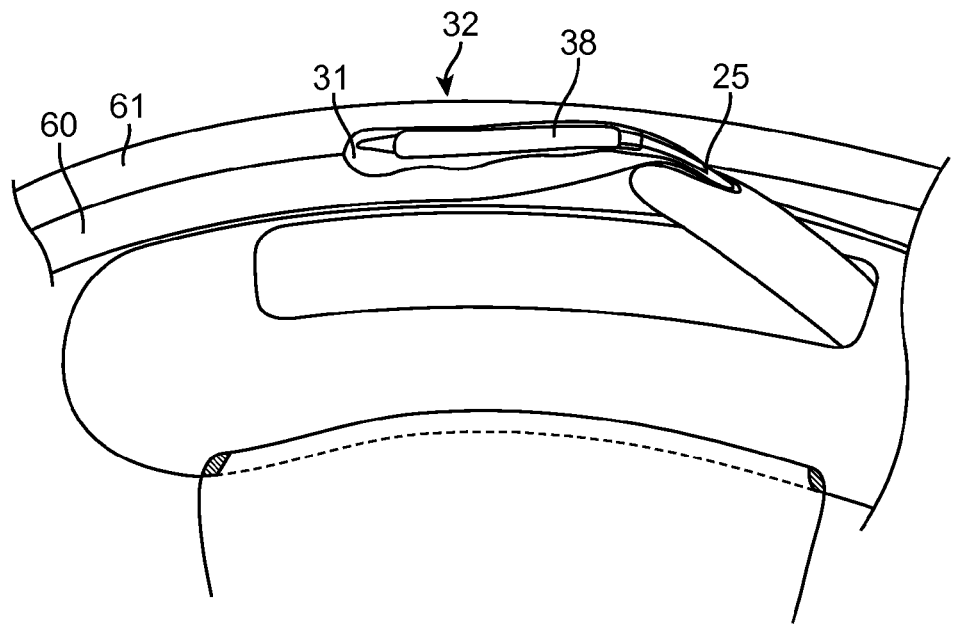

FIG. 11*a* depicts that the sub-intimal pocket creation mechanism 32 is advanced into the inter-layer plane 31. Following proper separation of tissue layers using the tissue layer separation mechanism 28, the sub-intimal pocket creation mechanism 32 is advanced through the main lumen 22 of the sub-intimal access mechanism 18, into the narrow lumen 24 of the tissue engagement mechanism 23, and out of the forward facing exit port 25. As depicted in FIG. 11*a*, the sub-intimal pocket creation mechanism 32 is advanced out of the forward facing exit port 25 of the tissue engagement mechanism 23, and into the newly created inter-layer plane 31 that now exists between the inner layer 60 and the outer layer 61 of the lumen wall. The sub-intimal pocket creation mechanism 32 is advanced far enough such that the proximal most portion of the deflated pocket creation balloon 38 is at least within the inter-layer plane 31.

Figure 11B:
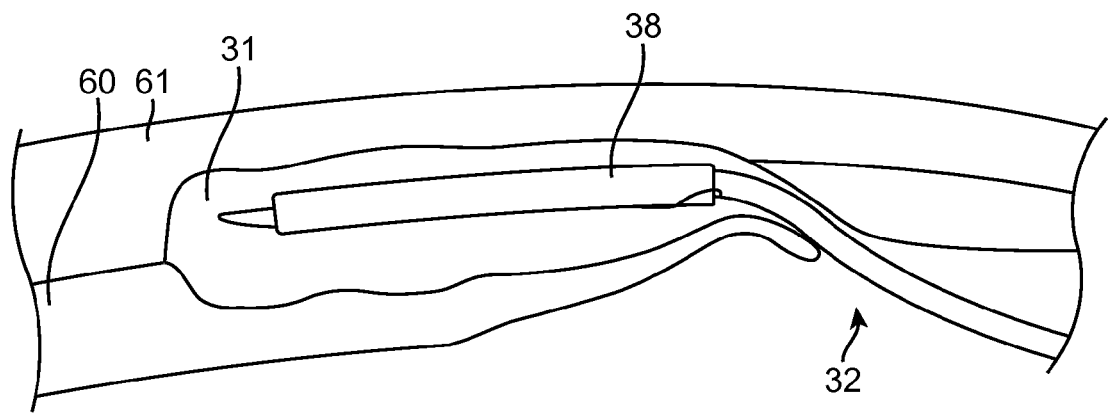

FIG. 11*b* depicts that the sub-intimal access mechanism 18 along with the conduit mechanism 2 has been removed, leaving only the sub-intimal pocket creation mechanism 32 behind, within the inter layer plane 31 previously created.

Figure 11C:
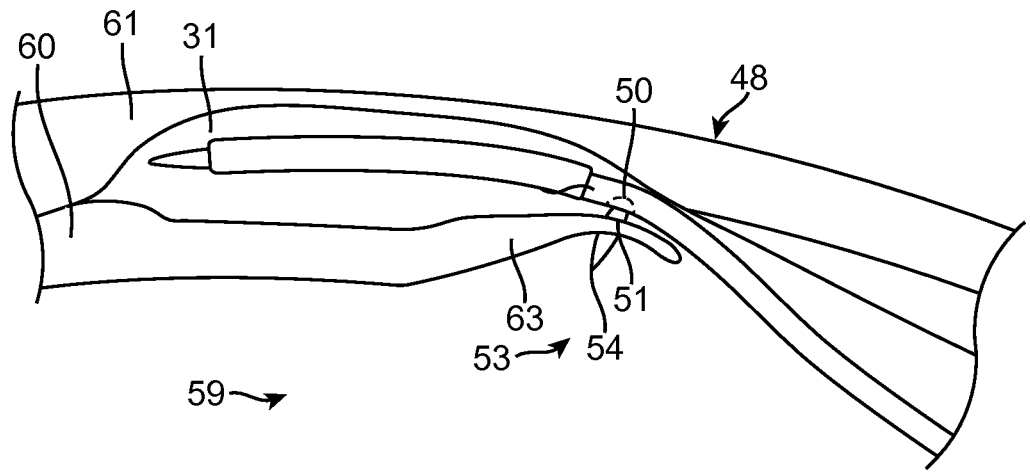

FIG. 11*c* depicts the first stage of actuation of the valve securement mechanism 48, which occurs prior to the sub-intimal pocket creation. Once the sub-intimal pocket creation mechanism 32 is advanced sufficiently into the newly created inter-layer plane 31, the securement mechanism delivery system 51 is advanced forward a small amount pushing the securement mechanism distal tip 53 out of the angled side port 50. Because of its sharp puncturing member 54, and the position and angular orientation of the angled side port 50 with respect to the newly separated inner tissue flap 63, the securement mechanism distal tip 53 punctures through the inner tissue layer flap 63 from its inter-layer plane 31 side, and emerges into the inside of the bodily lumen 59. The valve securement mechanism maintains control of the inner tissue layer flap 63 throughout the completion of sub-intimal pocket creation, prior to completing the subsequent stages of the valve securement.

Figure 11D:
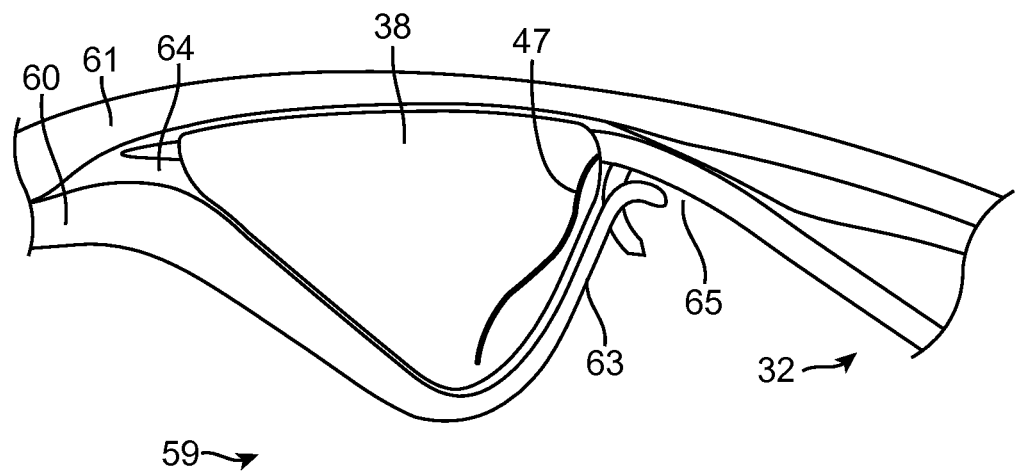

FIG. 11*d* depicts the sub-intimal pocket creation mechanism 32 being utilized. Following the first stage of actuation of the valve securement mechanism 48, and with the entire deflated pocket creation balloon 38 immersed within the inter-layer plane 31, the pocket creation balloon 38 is inflated through the inflation lumen 39, prompting expansion to its asymmetric shape. As depicted, the balloon expansion within the inter-layer plane 31 acts to further separate the inner layer tissue flap 63 from the outer layer 61 of the lumen wall, until a full sub-intimal pocket 64 has been created between the layers 61, 62. The geometry of this sub-intimal pocket 64 is determined by the shape, size and position of the pocket creation balloon 38 upon inflation. At this point, there exists a narrow inlet 65 in the top of the sub-intimal pocket with a circular shape just large enough to allow for dimensional clearance of the sub-intimal pocket creation mechanism 32. This inlet was created originally when the tissue engagement mechanism 23 penetrates through the vessel surface and into a wall of the vessel.

Figure 11E:
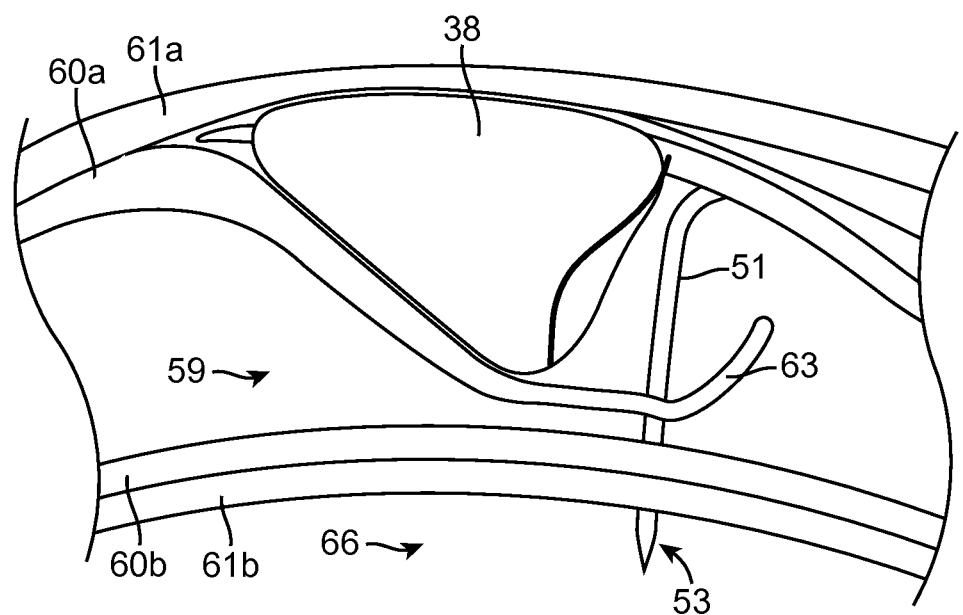

FIG. 11*e* depicts the second stage of actuation of the valve securement mechanism 48 immediately following, or simultaneously with, the sub-intimal pocket creation. After/during inflation of the pocket creation balloon 38, the securement mechanism delivery system 51 is further advanced, which acts to push the securement mechanism distal tip 53 through both the inner tissue layer 60*b* and the outer tissue layer 61*b* at the opposing side of the lumen, so that it rests in the extra-luminal space 66.

Figure 11F:
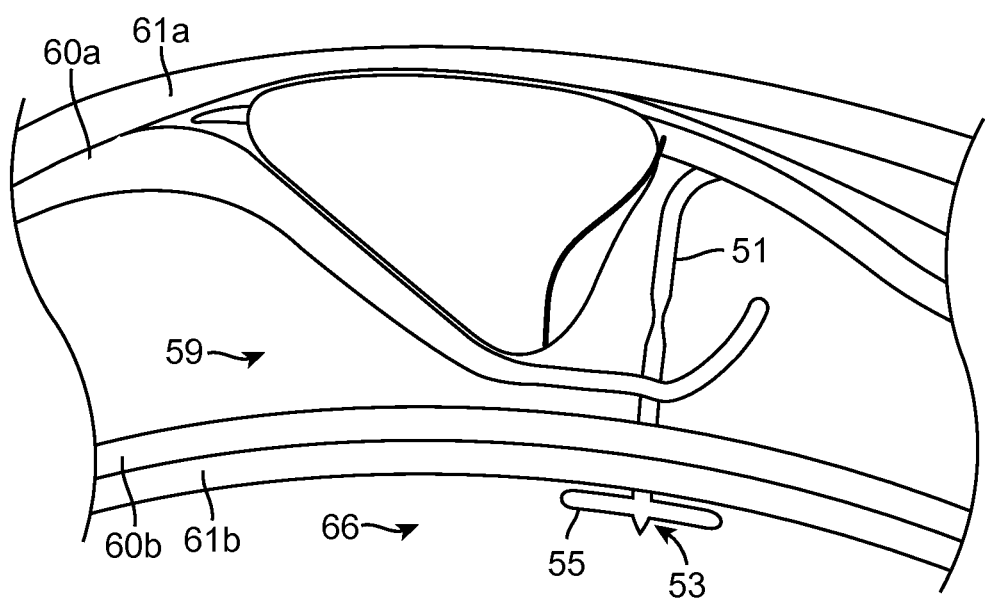

FIG. 11*f* depicts the third stage of actuation of the valve securement mechanism 48. Once the securement mechanism distal tip 53 has been advanced into the extra-luminal space 66, the constraining sheath 57 (not depicted) is retracted a small amount, allowing the distal clip arms 55 to spring outward into an orientation perpendicular to the axis of the delivery system 51 as a result of their shape memory characteristics. This clip orientation restricts the distal tip 53 from inadvertently disengaging in the backwards direction from the tissue layers through which it has been advanced.

Figure 11G:
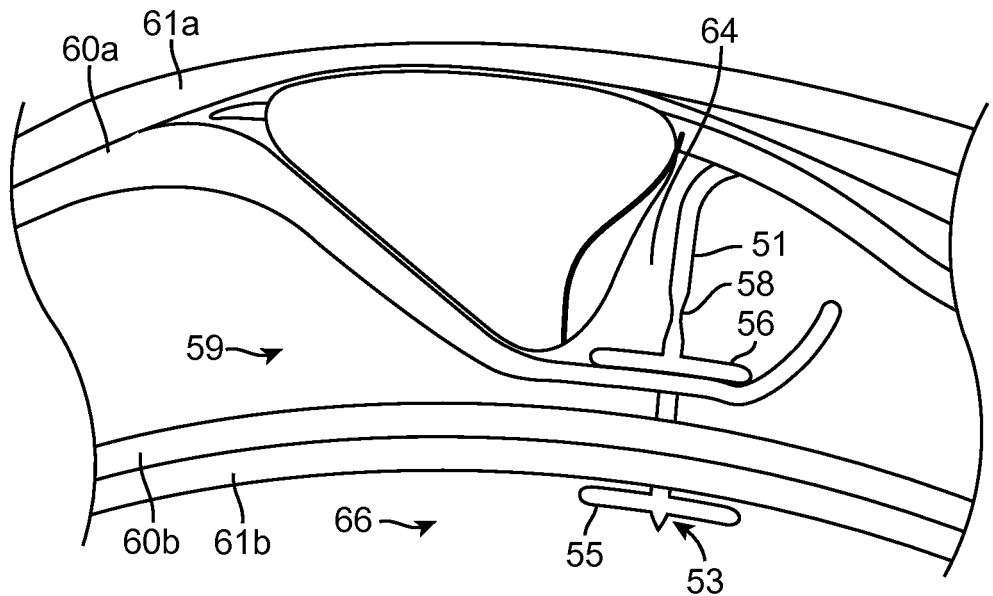

FIG. 11g depicts the forth stage of actuation of the valve securement mechanism 48. The constraining sheath 57 (not depicted) is retracted further to allow the proximal clip arms 56 to spring outward into a orientation perpendicular to the axis of the delivery system 51 as a result of their shape memory characteristics. Once expanded, the proximal clip arms 56 rest within the sub-intimal pocket 64. At this point the inner tissue layer 60a from one side of the lumen, the inner tissue layer 60b from the other side of the lumen, and the outer tissue layer 61b from the other side of the lumen, are constrained between the proximal clip arms 56 and the distal clip arms 55. Thus, the clip secures the flap formed from a first wall portion of a vessel relative to a second wall portion that is opposite from the first wall portion.

Figure 11H:
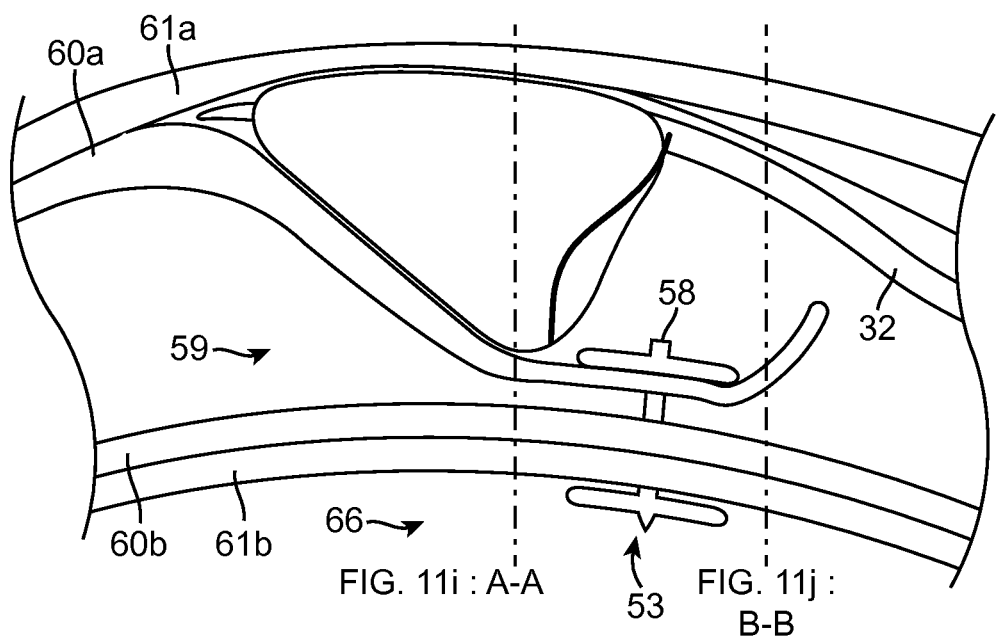

FIG. 11h depicts the fifth and final stage of actuation of the valve securement mechanism 48. The entire securement mechanism delivery system 51 is retracted forcing the securement mechanism distal tip 53 to detach from the securement mechanism delivery system 51 at the detachment joint 58. In this way, the securement mechanism distal tip 53 is left behind, depicted in this embodiment as an "H-tag" upon detachment. This form acts to prevent the newly separated inner tissue layer 60a from assuming its natural orientation against the outer tissue layer 61a, thus preventing it from biologically re-adhering in its original location. The delivery system 51 and the constraining sheath 57 are completely removed from the anatomy through the securement tool lumen 49 of the sub-intimal pocket creation mechanism 32. In other embodiments, instead of relying on tension to break the detachment joint 58, the joint 58 may be disintegratable in response to a current or heat applied therethrough.

Figure 11I:
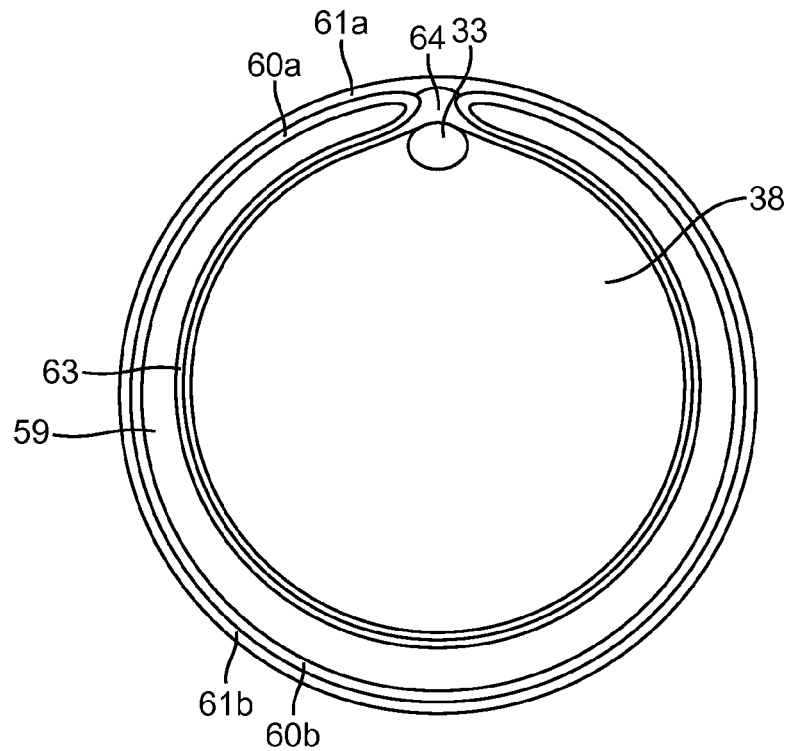

FIG. 11i depicts a cross-section view of the bodily lumen 59 at the longitudinal position of the pocket creation balloon's 38 largest diameter (denoted A-A on FIG. 11h). A large percentage of the area of the bodily lumen is occupied by the newly created inter layer pocket 64.

Figure 11J:
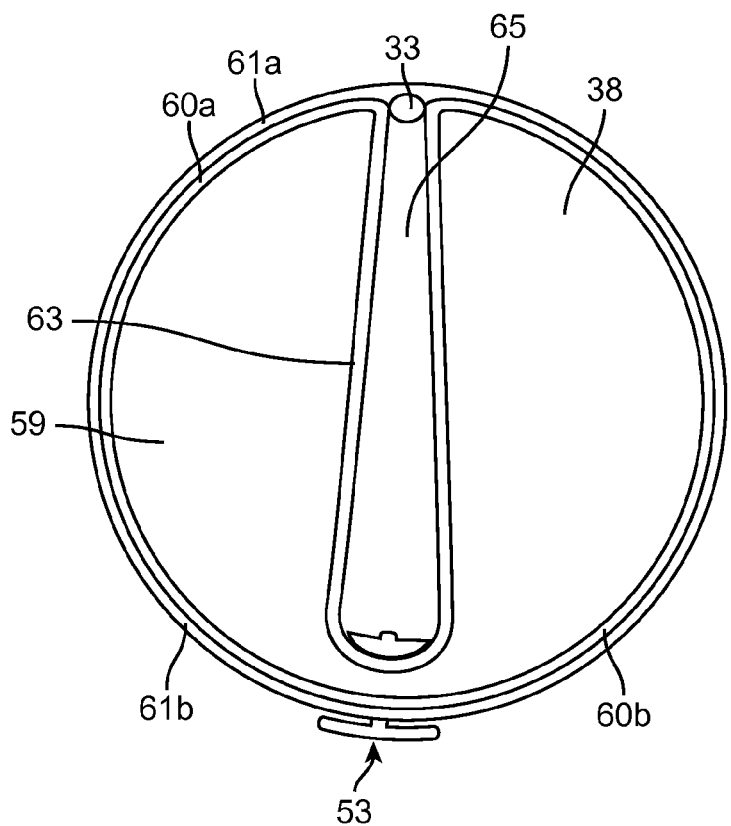

FIG. 11j depicts a cross-section view of the bodily lumen 59 at the longitudinal position just proximal on the sub-intimal pocket creation mechanism 32 to the pocket creation balloon 38 (denoted B-B on FIG. 11h). At this location, the narrow inlet 65 at the top of the inner tissue layer flap 63 is seen, and is a much smaller opening than the full extent of the pocket diameter at a more distal location.

Figure 12A:
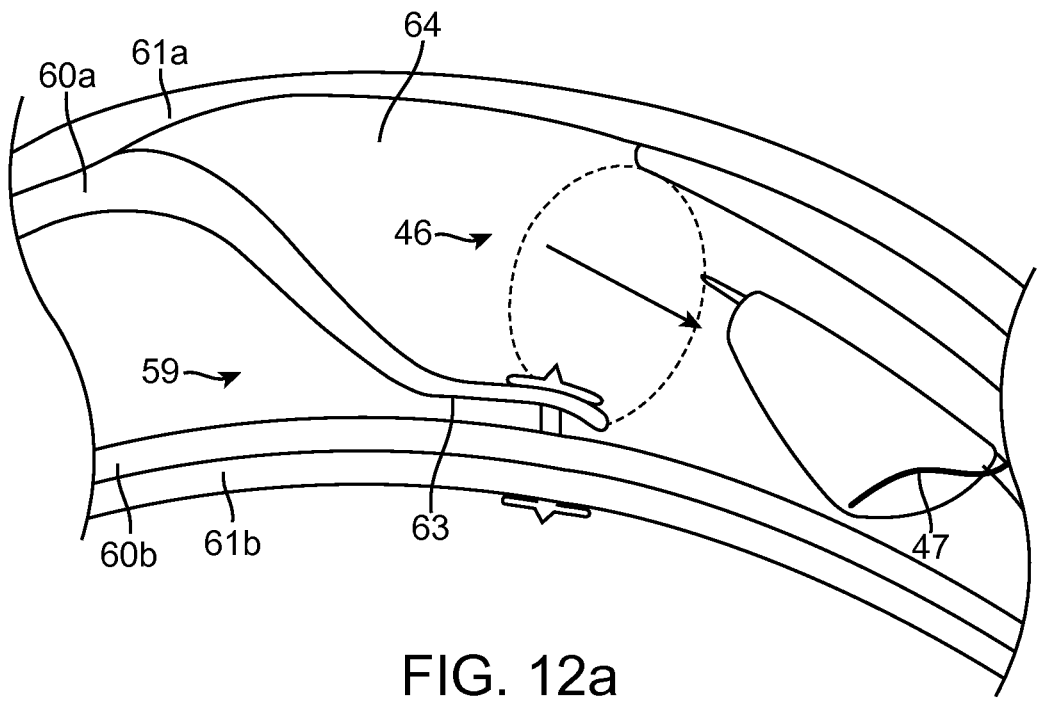
Figure 12B:
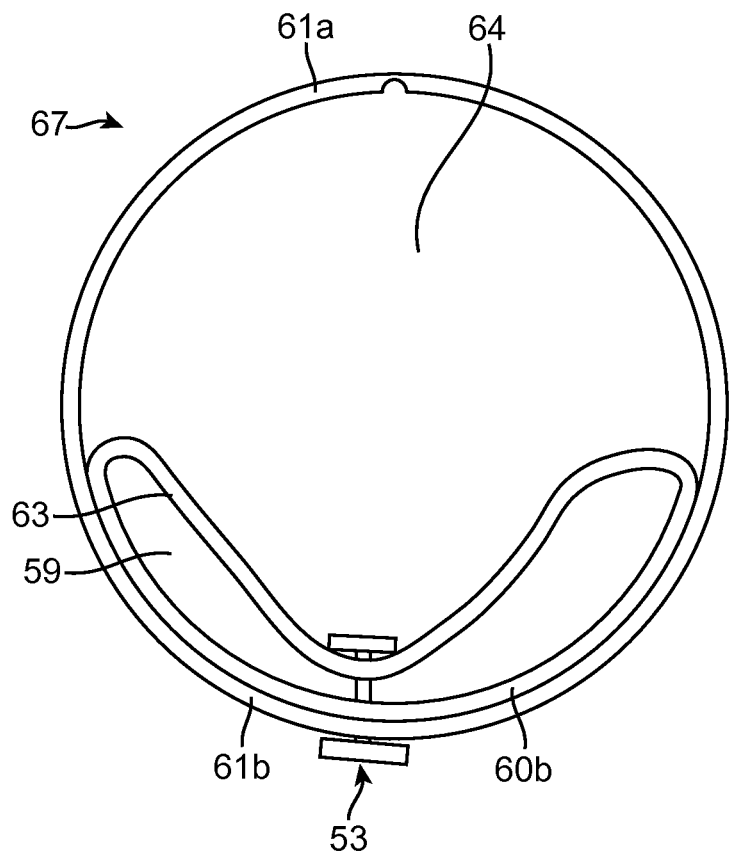

FIGS. 12a-12b depict the intimal separation mechanism 46 being utilized. The act of inflation of the pocket creation balloon 38 during the creation of a sub-intimal pocket 64 actuates the backward facing cutting mechanism 47 to its expanded orientation (depicted in FIG. 11d). As depicted in FIG. 12a, the sub-intimal pocket creation mechanism 46 is removed from the newly created sub-intimal pocket 64 while the pocket creation balloon 38 is still inflated. The proximal movement of the mechanism 46 causes the cutting mechanism 47 to cut tissue next to the opening 65 at one end of the flap 63, thereby increasing the size of the opening 65. This provides the flap 63 with the desired width. It should be noted that as the inflated balloon 38 of the mechanism 46 is removed proximally out of the inlet 65, counter-tension is created at the vessel wall, which allows the backward facing cutting mechanism 47 to make a clean, consistent cut at the vessel wall along a path (e.g., a curved path) according to the shape of the expanded backward facing cutting mechanism 47. In the embodiment depicted, the circumferential angle (measured along the circumference of the vessel) of the inner tissue layer separation is over 180° (e.g., 180°+10°), and the cut is near horizontal (i.e., the direction of the cut is approximately perpendicular to the longitudinal axis of the vessel). In other embodiments, the cut may not be horizontal. Also, in other embodiments, the length of the cut made by the cutting mechanism 47 may be less than 180°. The separation of the inner tissue layer flap 63 finalizes the top lip of the newly created autologous valve 67. At this point, the pocket creation balloon 38 is deflated, and the autologous valve creation has been accomplished. FIG. 12b depicts a cross-sectional view of the fully created autologous valve 67 at the longitudinal plane located directly proximal to the securement of the inner tissue layer flap 63 (denoted B-B on FIG. 11h), after the device has been fully removed.

After the valve 67 is created, the user may visualize the effect of autologous valve creation using fluoroscopic visualization techniques. Contrast agent 10 can be injected through the forward facing exit port 25 of the pocket-creation mechanism 32 (or through another fluid delivery device) at any appropriate time during the procedure. This tool will be especially useful after valve creation has been accomplished. In this case, the user may first deflate the pocket creation balloon 38 to facilitate placement of the forward facing exit port 25 in the newly created sub-intimal pocket 64. Standard techniques—including manual pumping of the calf muscle—can be used to force blood flow through the autologous valve 67 for evaluation. Once visualization confirms that autologous valve 67 is functioning properly, the device is removed from the bodily lumen.

Figure 13A:
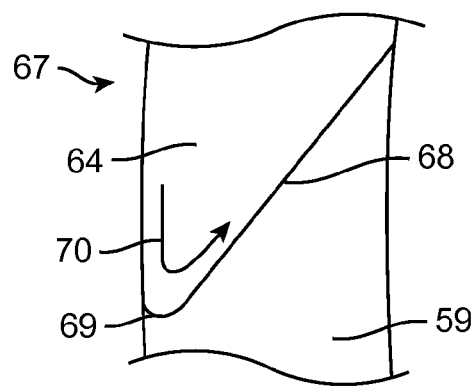
FIGS. 13a-13e depict different aspects of a valve geometry in accordance with some embodiments.
Figure 13B:
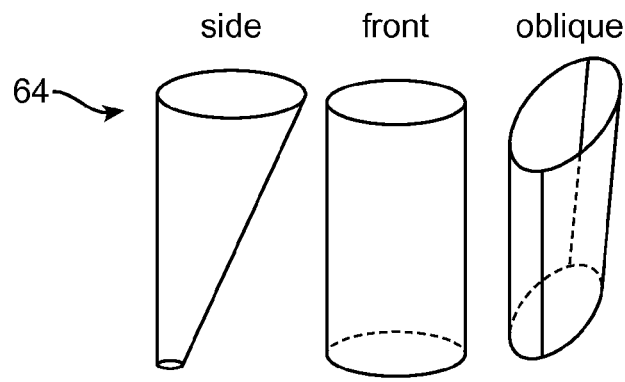
Figure 13C:
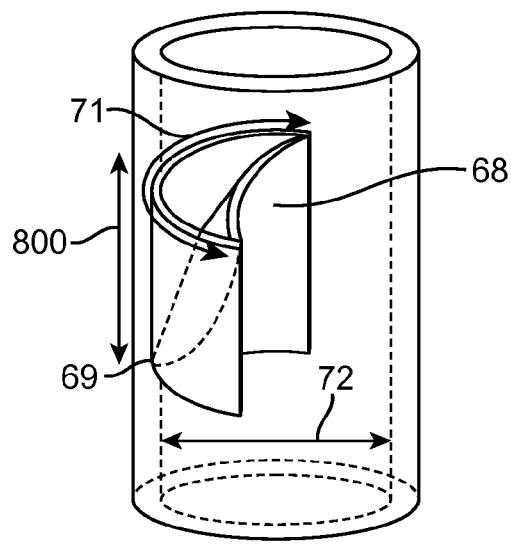
Figure 13D:
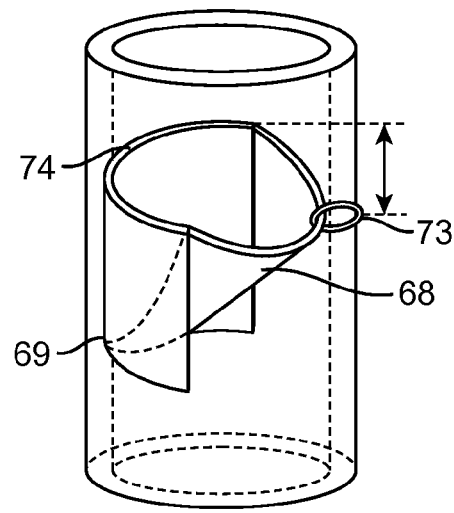
Figure 13E:
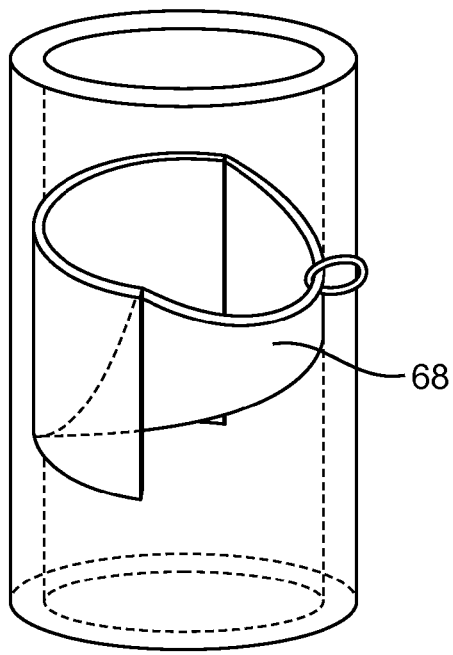

Upon creation of the autologous valve 67 depicted in FIG. 12b, a specific valve geometry is created. FIG. 13a-13e depict many aspects of one specific preferred valve geometry that could be created in a bodily lumen 59 using embodiments of the devices described herein. FIG. 13a depicts a cross-sectional view of a monocuspid valve geometry. A leaflet 68, composed of the inner layer tissue flap 63 is shown protruding from one lumen wall and extending toward and up to the lumen wall at the opposing side of the lumen, creating a mono-directional autologous valve 67. In this embodiment, the valve cusp 69 takes a curved shape, which allows for blood circulation 70, preventing stagnation. FIG. 13b depicts different shapes of the sub-intimal pocket 64 created between the leaflet 68 and the luminal wall from where the flap was dissected. This pocket 64 takes the shape of an up-side-down triangular extrusion with a curved side, which matches the lumen wall. FIG. 13c depicts approximate relative dimensions for the height 800 and circumferential width 71 of a valve geometry in accordance with some embodiments. The height 70 of the leaflet 68 (at its tallest point) is greater than the inner diameter of the lumen 72, and the circumferential width 71 of the leaflet 68 is slightly greater than 180°, as similarly discussed. As described previously, a securement mechanism 48 may be used to secure the flap of the valve to a vessel wall in accordance with some embodiments. FIG. 13d depicts the location of securement 73 to be longitudinally lower than the line of detachment 74 of the inner tissue layer 60 from the rest of the lumen wall (see arrow in figure representing the offset). FIG. 13e depicts the effect of this securement location during the closing cycle of the autologous valve 67, which results in the lateral movement of redundant tissue of the leaflet 68 so that it may freely occlude against the opposing lumen wall in the closed valve orientation, without having to over-stretch the tissue of the leaflet 68.

It should be noted that the system and method for creating a valve inside the vessel is not limited to the embodiments described previously. In other embodiments, the system may have different configurations. Also, in other embodiments, the method may be carried out using different devices and/or techniques.

Figure 14:
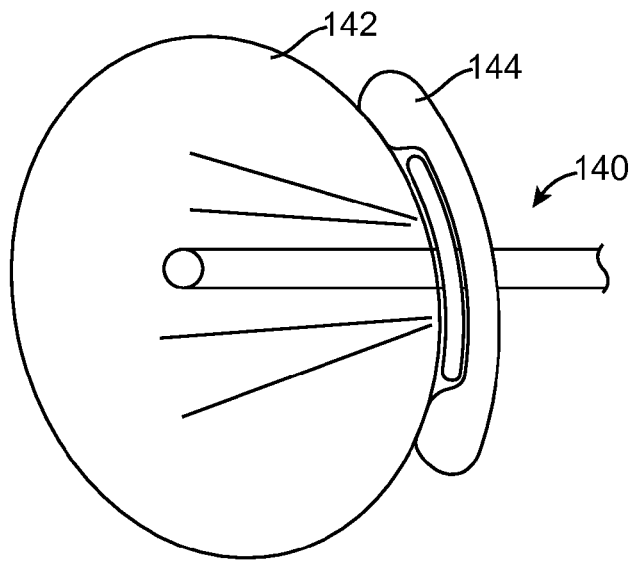
FIG. 14 illustrates an ultrasound device in accordance with some embodiments.

In the above embodiments, the device has been described as utilizing contrast solution and fluoroscopic techniques for \visualization. In other embodiments, the device may utilize an external ultrasound device to facilitate navigation of the conduit mechanism 2 to the desired target location, to monitor progress of the valve creation procedure, and/or to confirm that a desired valve has been created. FIG. 14 an ultrasound probe 140 with a specific shape to conform to the external anatomy of the thigh 142 or other external anatomical locations. In such embodiments, if used in the venous system, the depth of penetration may be programmed for focus on the deep vein anatomy of the average patient with deep vein insufficiency, particularly for superficial femoral vein, the popliteal vein, the common femoral vein, or any of other veins of the deep venous system. In the embodiment depicted, the front end of the probe has a fixturing mechanism 144 so that upon actuation the probe can remain static with respect to the leg. In this embodiment, the fixturing mechanism includes a suction cup that can be actuated to create a low-pressure chamber by sealing off the chamber while removing some air within the chamber. Such a mechanism can be easily reversed to decouple the device from the patient when necessary. In another embodiment, the fixturing mechanism 144 may be a strap that wraps around the patients leg, and can be tightened or loosened with a latching mechanisms for semi-permanent clamping. In some such embodiments, the ultrasound probe 140 has a paired video output on the probe itself, allowing the physician to visualize the underlying vein by looking directly at the patient's leg.

In a previous embodiment, the device 140 was described as an ultrasound device placed external to the patient for achieving visualization. In other embodiments, the device 140 may be another external imaging modality. For example, in other embodiments, the visualization may be accomplished with magnetic resonance imaging. In other embodiments, the visualization may be accomplished with computed tomography scanning. In still other embodiments, the visualization may be accomplished with optical coherence tomography. In further embodiments, the visualization may be accomplished with intravascular ultrasound.

In other embodiments, the visualization may be achieved with other sensing technologies that help evaluate certain hemodynamic parameters, which aid in identifying the proper location for intervention or for assessing procedural success during and/or after the procedure. Such modalities may include device for measuring localized blood pressure, flow meters, pulse oximetry, or for performing other physical examination(s).

In other embodiments, the visualization may be achieved using a direct visualization technique. In one such embodiment, the interventional site is evacuated of blood. For example, proximal and distal balloons may be delivered into the vessel lumen, where they are inflated, and blood is evacuated through a port in the catheter between the two balloons. In one such embodiment, the two balloons are housed on separate but parascoping catheters. In another such embodiment, the balloons are on the same catheter. In some cases, the balloons utilized for evacuation of blood may also provide additional longitudinal countertension. After the blood between the balloons is removed, a camera may then be delivered in the vessel for viewing. In another embodiment, an external wrap and turnakit system may be used to exsanguinate the leg of blood prior to the procedure. In other embodiments, direct visualization is obtained without evacuating the site of blood, but by housing a camera within a balloon. The balloon can be inflated with a clear liquid or gas, and pushed against a luminal wall, allowing direct visualization of the wall and surrounding anatomy. In another embodiment, the camera can be housed within a device having a clear solid surface which allows the camera to view tissue therethrough. In one other embodiment, clear gas or liquid can be continuously introduced in front of the camera to ensure continuous visualization through blood.

In other embodiments, direct visualization may be obtained with a camera positioned within the sub-intimal access mechanism 18. In another similar embodiment, the camera is located within the conduit mechanism 2 directed toward the interventional site through the sideways facing exit port. In other embodiments, the camera may be mounted on a separate guide that can be fed at anytime through any of the previously described lumens. In further embodiments, the camera may be housed in a completely separate guiding device, that may be introduced to the interventional site through the same or different incision point. For example, the visualization device may be inserted percutaneously at a first incision point to enter into the vessel lumen, and any of the valve creation devices described herein may be inserted percutaneously at a second incision point to enter into the same vessel lumen. The visualization device and any of the devices described herein may be advanced inside the vessel from opposite directions to reach the same target location.

Figure 15:
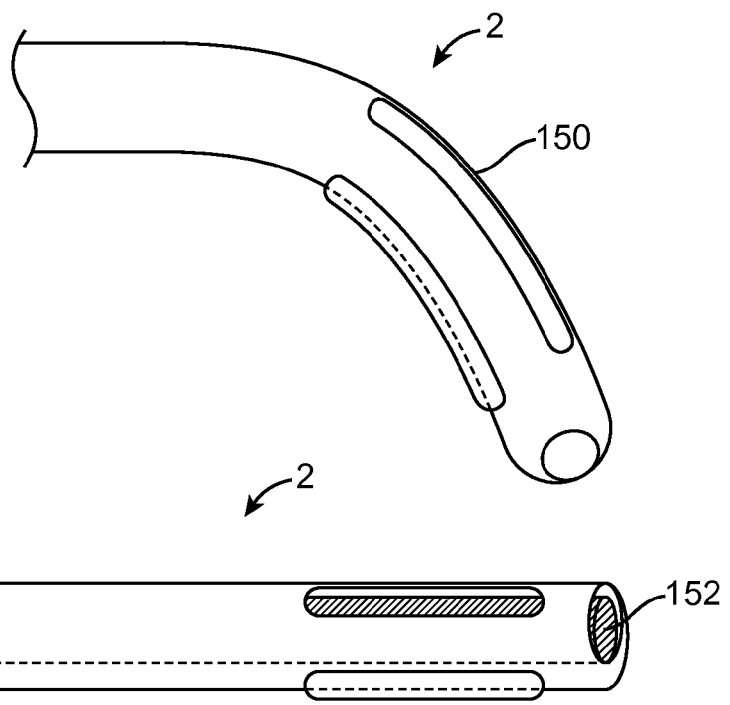
FIG. 15 illustrates a conduit mechanism with a pre-formed curvilinear configuration in accordance with some embodiments.

In the above embodiments, the device has been described as utilizing a tensioned wire bonded to the distal tip of the conduit mechanism 2 for the angling mechanism 9. In other embodiments, as depicted in FIG. 15, the device may utilize a pre-formed conduit mechanism 2 with a curve at the distal section 150. In this embodiment, the conduit is naturally curved at the distal section 150, but may be straightened during access of the bodily lumen if necessary by inserting a straight stiff stylet 152 in the internal contrast lumen 6.

Figure 16:
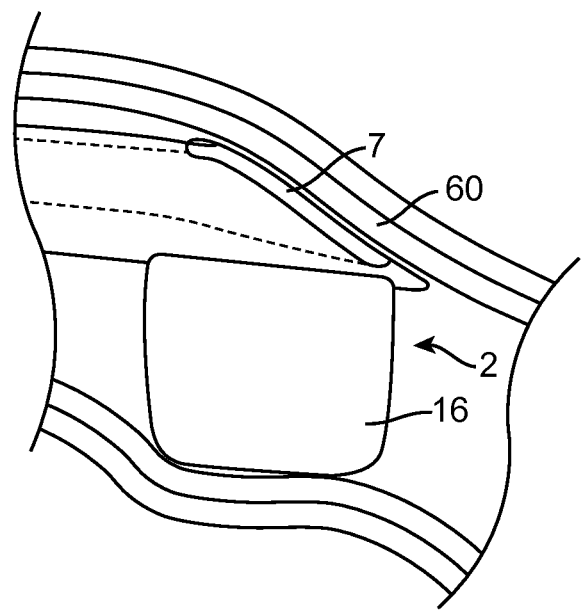
FIG. 16 illustrates a conduit mechanism having an angling mechanism in accordance with some embodiments.

FIG. 16 depicts another embodiment, in which the angling mechanism 11 is embodied as a taper on one side of the conduit mechanism 2 at approximately the same longitudinal and radial position of the sideways facing exit port 7. Upon actuation of the wall-tensioning mechanism 15, the inner tissue layer 60 will conform to the tapered geometry, thus forming an angle relative to a longitudinal axis of the conduit mechanism 2. In such configuration, when the sub-intimal access mechanism 18 exits through the port 7, the mechanism 18 will penetrates into the inner tissue layer 60 at a desired angle relative to the tissue layer 60.

Figure 17:
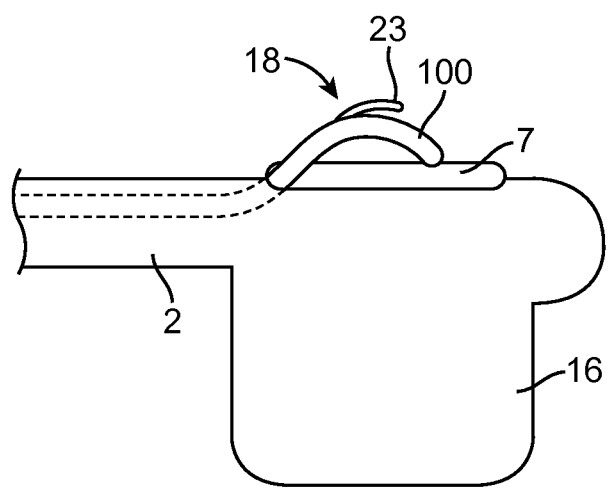
FIG. 17 illustrates an angling mechanism being embodied as the sub-intimal access mechanism in accordance with some embodiments.

FIG. 17 depicts another embodiment, in which the angling mechanism 11 is embodied as the sub-intimal access mechanism 18 itself, wherein the mechanism 18 has a pre-formed shape achieved by making at least a part of the mechanism 18 using Nitinol or other material having shape-memory characteristic. In this embodiment, the sub-intimal access mechanism 18 is shaped so that upon exiting the constraints of the conduit lumen 6 through the sideways facing exit port 7, it takes its natural angled shape so that it penetrates the inner tissue layer 60 at a desired angle relative to the layer 60. In this way, the sub-intimal access mechanism 18 takes an appropriate angle with the inner tissue layer 60 upon exiting the sideways facing exit port 7.

Figure 18:
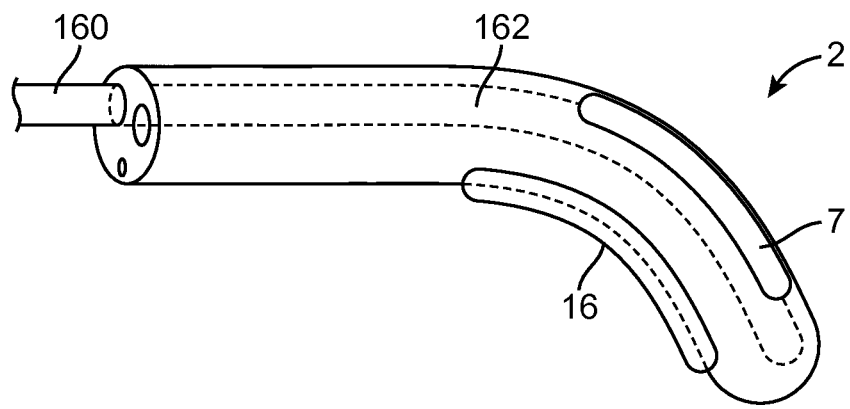
FIG. 18 illustrates an angling mechanism embodied as a curved stylet in accordance with some embodiments.

FIG. 18 depicts another embodiment, in which the angling mechanism 11 is embodied as a curved stylet 160 which is introduced through an additional lumen 162 in the conduit mechanism 2. Upon introduction, because the curved stylet 160 has sufficient stiffness to transfer that curvature to the conduit mechanism 2 and the vessel itself, the inner tissue layer 60 of the vessel will be forced to curve along the surface of the conduit mechanism 2.

Figure 19:
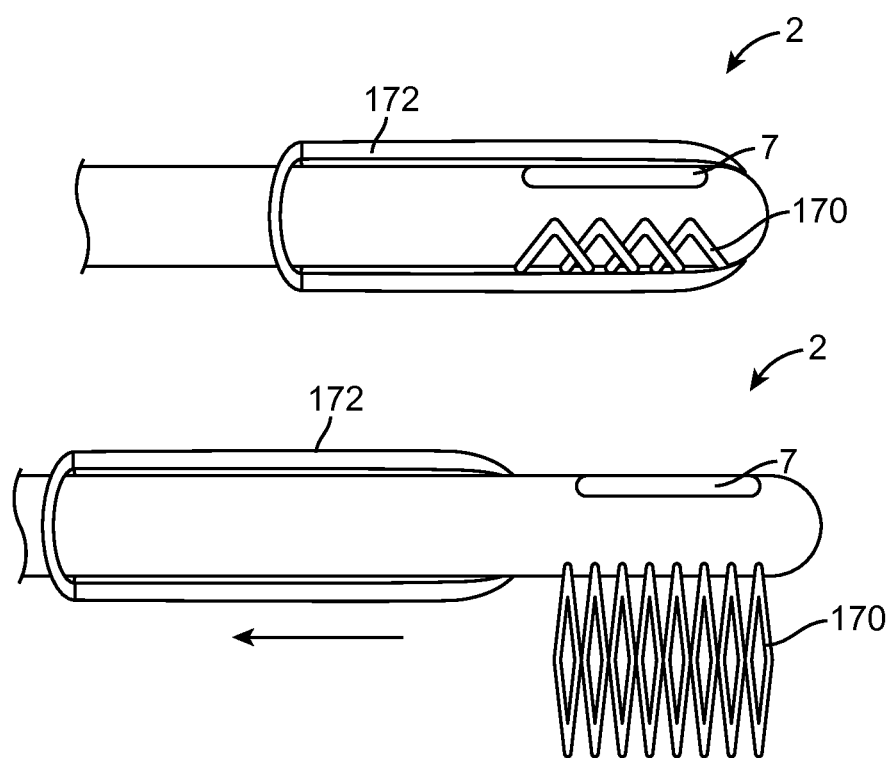
FIG. 19 illustrates a cage as a wall-tensioning mechanism in accordance with some embodiments.

It should be noted that the wall-tensioning mechanism 15 is not limited to the balloon 16 described previously, and that in alternate embodiments the wall-tensioning mechanism 13 may be implemented using other device(s) and technique(s). FIG. 19 depicts one such embodiment, in which the wall-tensioning mechanism 15 is an expandable cage 170 made from shape-memory Nitinol attached to the side of the conduit mechanism 2. Prior to actuation, a sheath 172 rests over the compressed Nitinol cage 170. To actuate the wall-tensioning mechanism 15, the sheath 172 is retracted such that the cage 170 assumes its shape memory expanded configuration.

In other embodiments of the wall-tensioning mechanism 15, the cage 170 is made of Stainless Steel (or any of other suitable materials, such as pure metals, alloys, or shape memory polymers), and may be expanded with assistance from an expanding balloon.

Figure 20:
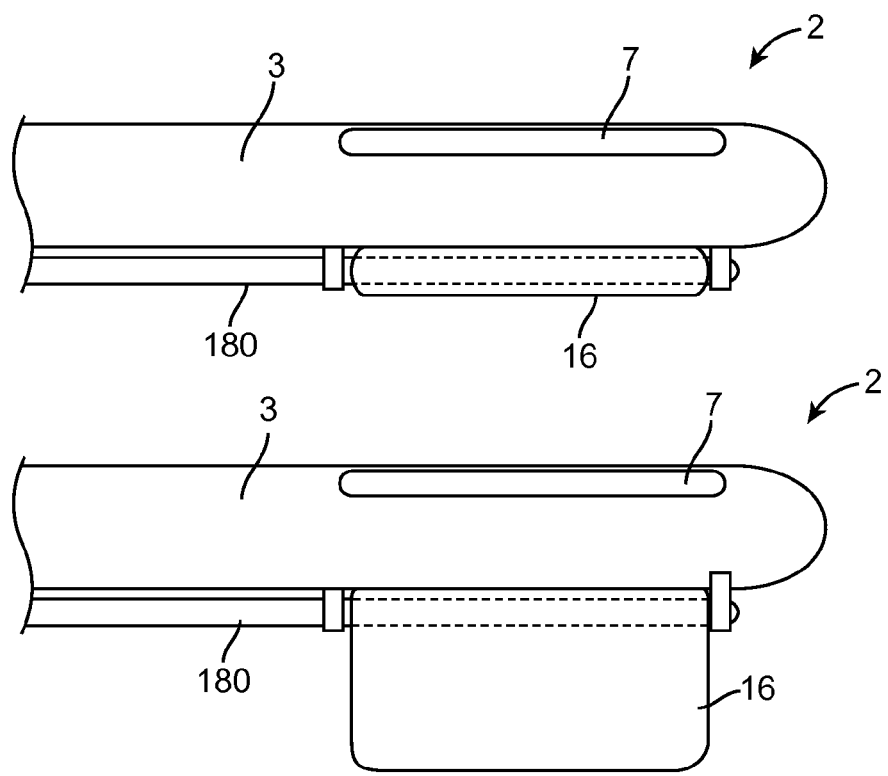
FIG. 20 illustrates another conduit mechanism in accordance with some embodiments.

In some embodiments described herein, the wall-tensioning mechanism 15 is an expanding balloon 16 attached to the elongated member 3 of the conduit mechanism 2. In other embodiments, as depicted in FIG. 20, instead of a side-ways facing balloon 16 bonded to the surface of the conduit mechanism 2, a radially symmetric balloon is mounted to a delivery catheter 180, and the center of the balloon 16 is offset from the axis of the catheter 180. In such configuration, that expansion of the balloon 16 in one direction is constrained by the wall of the elongated member 3. In such embodiments, the balloon 16 is forced to expand outward with a bias toward the interior vessel wall, offset from the longitudinal axis (e.g., central axis) of the main conduit mechanism 2. In other embodiments, the balloon 16 may be made from a first material that is stiffer on one side (the side closer to the elongated member 3), and relatively less stiff on the opposite side (the side further away from the elongated member 3). Such configuration allows the balloon 16 to expand to an asymmetric shape, or to a shape having a central axis that is offset from the axis of the catheter 180.

Figure 21:
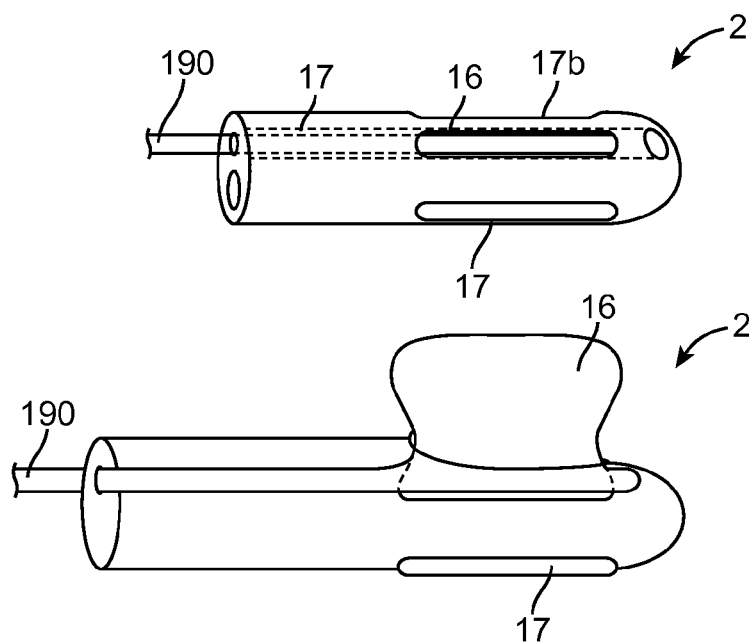
FIG. 21 illustrates a conduit mechanism being used with an expandable member in accordance with some embodiments.

FIG. 21 depicts another embodiment, in which a radially symmetric balloon 16 is attached to an independent balloon guide 190 with an inflation lumen of its own. This balloon guide 190 and balloon 16 is housed within a balloon lumen 17 within the conduit mechanism 2. The inflation lumen 7 is in fluid communication with the proximal end of the conduit mechanism 2. In this embodiment, there exists a sideways facing exit port 7b in the conduit surface, at the same longitudinal position as the balloon 16 itself, spanning a length of at least that of the balloon 16. Upon inflation of the balloon 16, the balloon 16 is constrained on one side by the wall of the balloon lumen 17, but free to expand out of the balloon side-port 17b, which allows for outward expansion in a perpendicular direction to a longitudinal axis of the conduit mechanism 2. In other embodiments, the balloon 16 may have an asymmetric configuration. Also, in any of the embodiments described herein, the balloon 16 may be compliant.

In any of the embodiments described herein, the balloon 16 may be configured to expand in a lateral direction, wherein the balloon 16 is mounted to the conduit mechanism 2 with its direction of expansion being perpendicular to the longitudinal axis of the conduit mechanism 2. In such configuration, when the balloon 16 is inflated, it expands laterally to dilate the vessel wall.

Figure 22:
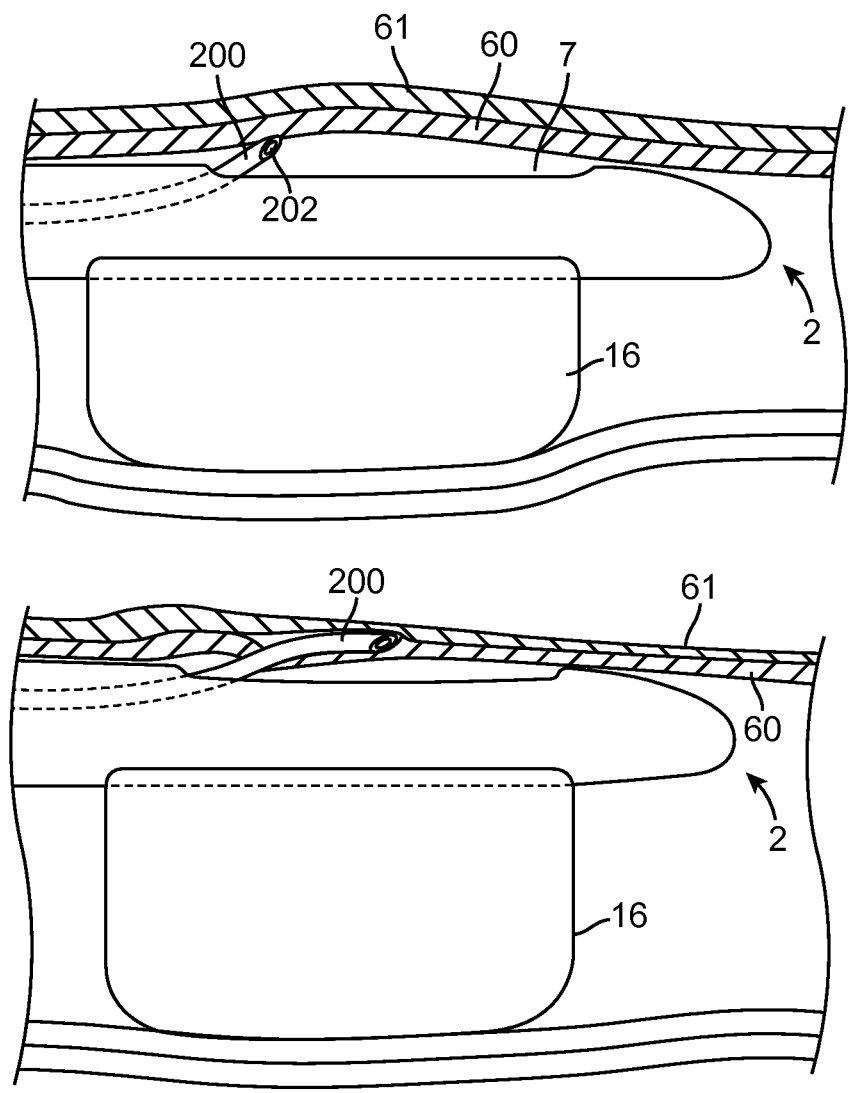
FIGS. 22-26 illustrate different sub-intimal access mechanisms in accordance with different embodiments.

The sub-intimal access mechanism 18 is not limited to the embodiments described previously, and may have different configurations in different embodiments. FIG. 22 depicts the sub-intimal access mechanism 18 having a naturally curved, forward facing needle 200 with internal lumen 202, used to directly gain access into the sub-intimal space. The curved needle 200 takes a tight curve outward toward the vessel wall as it initially exits from the port 7, but straightens out such that it becomes parallel with the longitudinal axis of conduit mechanism 2 after it has been further deployed into the wall of the vessel. In this embodiment, the sub-intimal access mechanism 18 is advanced through the main lumen 6 of the conduit mechanism 2 until it approaches the sideways facing exit port 7. The lack of constraint provided allows the curved needle 200 to take its natural shape described. It is then advanced further until it penetrates the inner tissue layer 60, which bottoms out within the cusp created between the sub-intimal access mechanism shaft and the conduit surface. At this point, a tissue layer separation mechanism, such as fluid, an expandable device, or both, may be delivered out of the lumen 202 of the needle 200 to separate the layers 60, 61.

Figure 23:
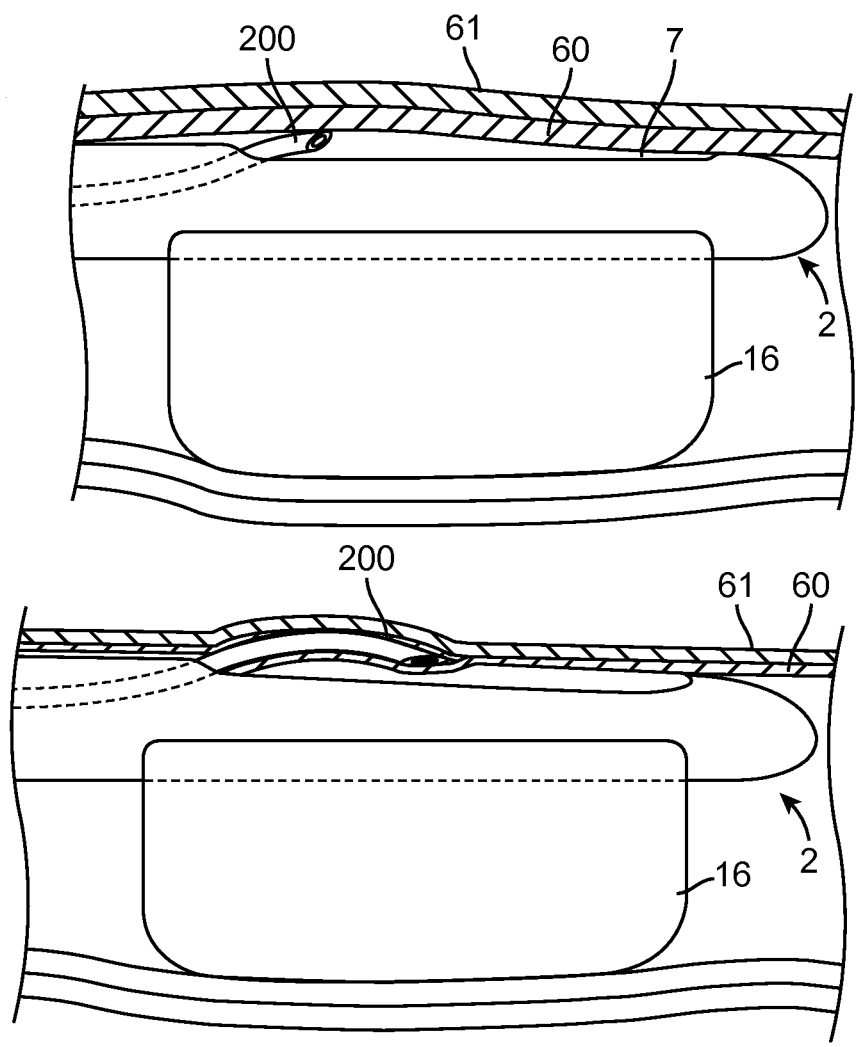

FIG. 23 depicts another embodiment in which the sub-intimal access mechanism 18 takes the form of a curved needle 200 used in a similar way as the previous embodiment. The curved needle 200 takes a tight curve outward toward the vessel wall as it is initially delivered out of the port 7 (top figure). As the needle 200 is further advanced distally, it curves back slightly away from the layer 61 of the vessel wall (bottom figure). This configuration allows the needle tip to first contact the tissue at an angle that is almost parallel (e.g., $0°\pm10°$) to the vessel wall, then as the curved needle 200 is advanced so that its full curvature exits the sideways facing exit port 7, the needle tip begins to change angle so that its tip is pointing towards the center of the vessel lumen. This embodiment allows for the curved needle 200 to gain access to the inter layer plane between the layers 60, 61, but then helps to prevent full perforation of the vessel wall by not allowing the needle 200 to continue advancing distally towards the layer 61.

Figure 24:
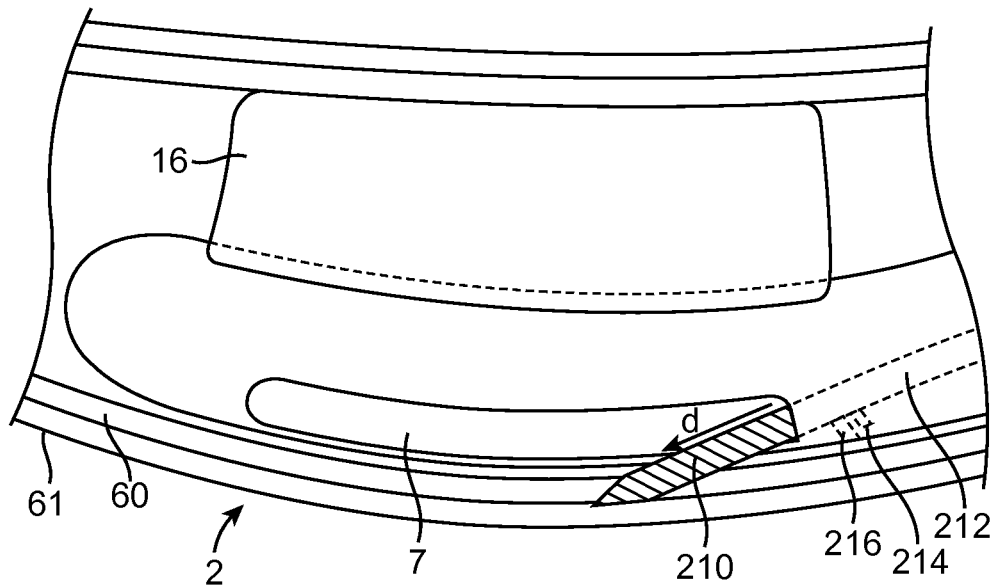

FIG. 24 depicts another embodiment, in which the sub-intimal access mechanism 18 is a forward facing needle 210 with internal lumen 212, that is accelerated in a specific way in order to directly gain access into the sub-intimal space. In this embodiment, the needle 210 is accelerated a fixed distance out of the sideways facing exit port 7 of the conduit mechanism 2. Upon exiting the conduit mechanism 2, the needle 210 punctures the inner tissue layer 60 at a non-perpendicular angle to the vessel wall. The accelerated motion will help to prevent visco-elastic dynamic effects of the vessel wall, including recoil and relaxation from recoil back toward the puncturing element. This mechanism and method provides a safe way to get to a specific distance within the lumen wall, as there will be close to a one to one correspondence between the distance the needle 210 is extended and the depth of penetration. Actuation of this forward motion may be facilitated by a spring mechanism on the proximal end of the device, much like the actuation mechanism 52 of the securement mechanism 48 previously described. In this embodiment, the distal tip of the needle 210 is advanced up to the interface between the inner tissue layer 60, and the outer tissue layer 61. Depth of penetration is controlled by a mechanical stop 214 located some distance from the distal end of the needle 210. The mechanical stop 214 is configured to abut against a protrusion 216 at the conduit mechanism 2 to thereby stop the advancement of the needle 210. The delivered needle 210 may be used to carry out various functionalities as similarly described previously with reference to the tissue engagement mechanism 23.

Figure 25A:
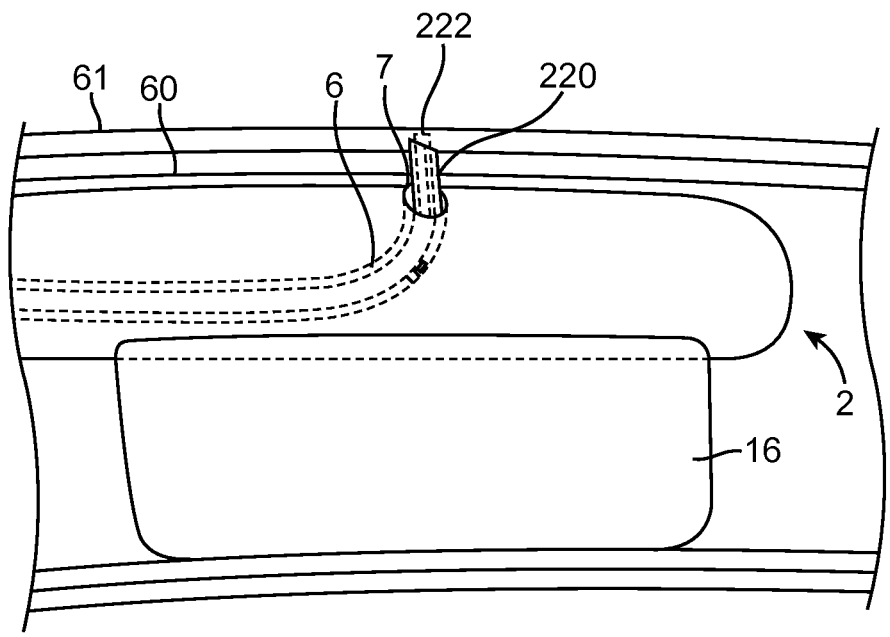

FIG. 25a depicts another embodiment. In this embodiment, the sub-intimal access mechanism 18 is a needle 220 with an internal lumen 222 that is configured to exit out of the side port 7 at the conduit mechanism's distal end. The distal tip of this needle 220 is sharp. The needle 220 is accelerated a fixed distance out of the sideways facing exit port 7 of the conduit mechanism 2 and into the inner tissue layer at a perpendicular angle to the luminal wall. In this depiction, the sideways exit port 7 is circular rather than a long oval and is connected to an internal delivery lumen 6 within the conduit mechanism 2. This delivery lumen 6 has a 90-degree curvature near the distal end of the conduit mechanism 2, which connects to the sideways facing exit port 7. The delivered needle 210 may be used to carry out various functionalities as similarly described previously with reference to the tissue engagement mechanism 23.

Figure 25B:
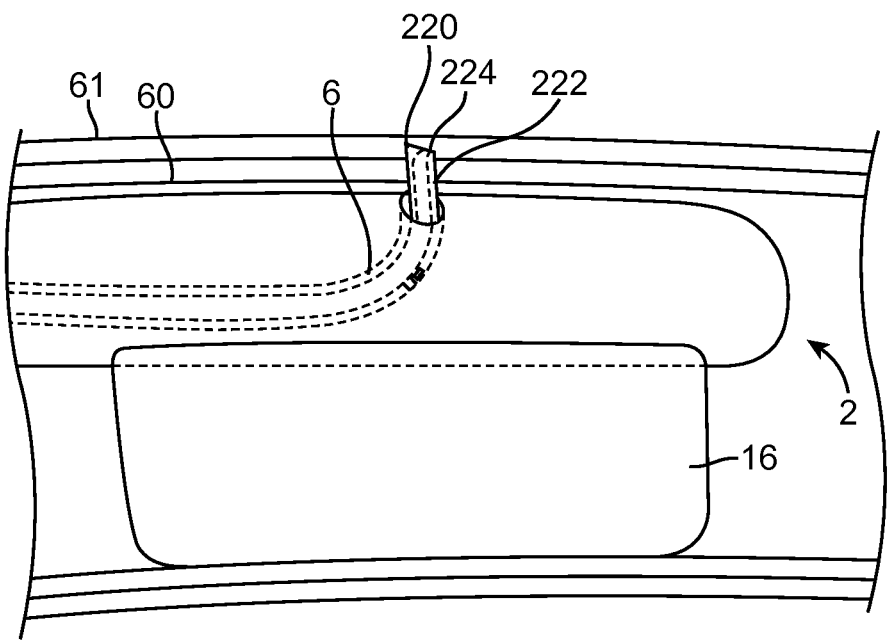
Figure 25C:
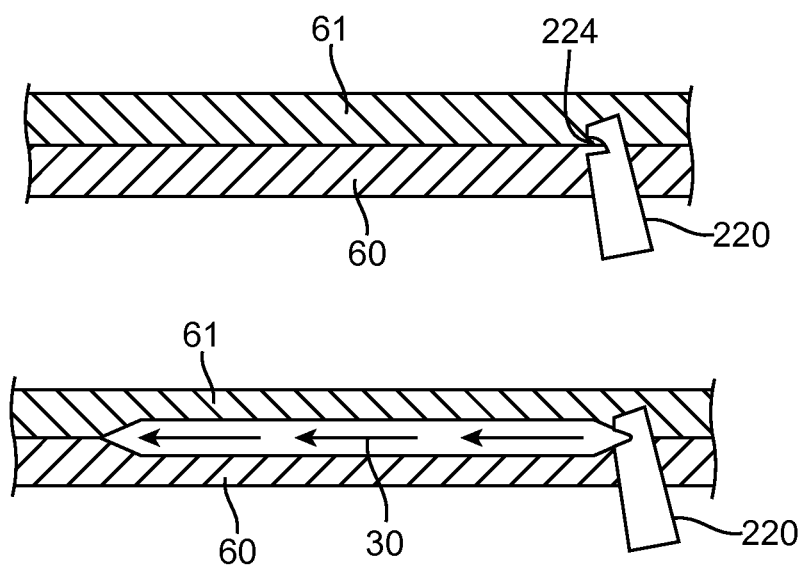

FIGS. 25b-25c depict alternative embodiments, in which the needle 220 is comprised of an internal lumen 222 in fluid communication with a port 224 at the distal end. In these depictions, the needle tip is sharp but closed, and the port 224 faces towards a direction that is approximately parallel (e.g., 0°±10°) to the vessel wall. Such configuration allows the fluid 30 exiting the needle 220 to travel at a direction that is approximately parallel to the vessel wall to thereby dissect tissue in the vessel wall.

In other embodiments of the sub-intimal access mechanism 18, a guidewire may be used in place of a forward facing needle to penetrate the inner tissue layer 60. In some cases, the guidewire may be configured to accelerate distally to travel a fixed distance, as similarly described previously with reference to the needle. In one such embodiment, the guidewire penetrates into the vessel wall at a non-parallel angle to the lumen wall. In another such embodiment, the guidewire penetrates into the lumen wall at an angle that is perpendicular to the wall of the vessel. In these embodiments, a hollow tube (which may be considered to be a part of the sub-intimal access mechanism 18, or a separate device) may be passed over the guidewire upon gaining access to the interface between the inner tissue layer 60 and the outer tissue layer 61, until it too rests in the inter-tissue plane. The delivered tube may be used to carry out various functionalities as similarly described previously with reference to the tissue engagement mechanism 23.

Figure 26A:
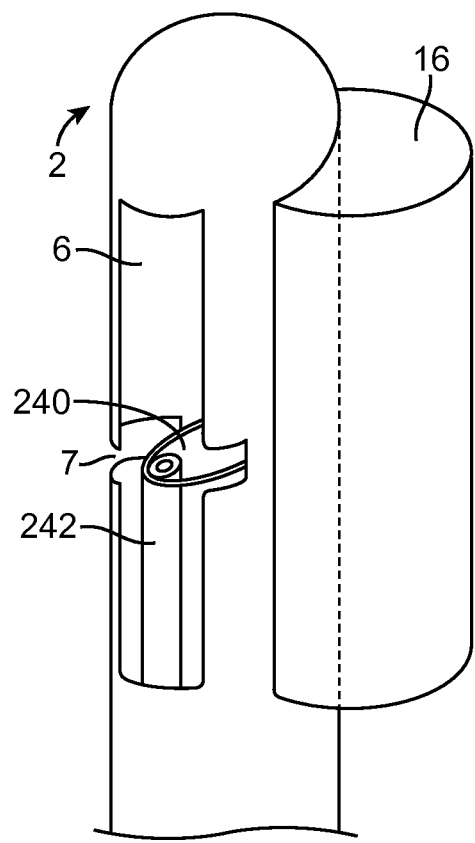
Figure 26B:
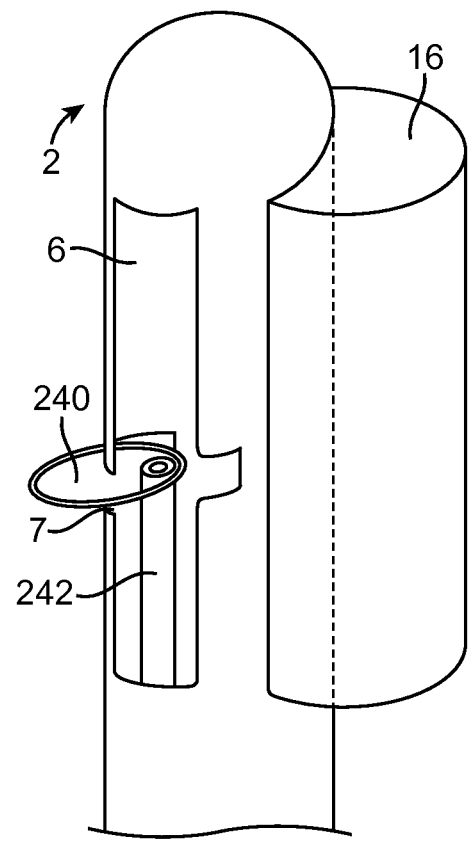

In the above embodiments, the device has been described as having a tissue engagement mechanism 23 (which may include a needle, or a guidewire) for penetrating into the wall of the vessel. FIGS. 26a-26b depict an alternate embodiment, in which the sub-intimal access mechanism 18 includes a curved blade 240, mounted on a rotary guide 242, which is free to rotate within the main lumen 6 of the conduit mechanism 2. A sideways facing exit port 7, allows the blade 240 to periodically protrude radially past the surface of the conduit mechanism 2. In this way, through a certain range of angles of rotation, the blade 240 is safely constrained within the outer surface of the conduit mechanism 2, and therefore not in contact with the vessel wall, as depicted in FIG. 26a. Conversely, through another certain range of angles of rotation, the blade 240 protrudes radially past the outer surface of the conduit mechanism 2, and thus contacting the wall of the vessel, as the conduit surface itself is in contact with the vessel wall (due to the actuation of the wall-tensioning mechanism 15), as depicted in FIG. 26b. Once the blade 240 is rotationally actuated from the proximal end, an incision is made in only the inner tissue layer 60, due to the fixed depth of cut provided by the limited reach of the blade 240 from the sideways facing exit port 7. In these embodiments, a delivery device (e.g., a hollow guidewire, a needle, a probe, etc.) which functions as a delivery mechanism for the tissue layer separation mechanism (e.g., fluid, balloon, expandable device, etc.) can then be introduced through the incision created by the blade 240, by passing through the sideways facing exit port 7. Henceforth, the valve creation procedure can be completed in similar way as that described previously, with the exception that the blade 240 is used to accomplish the task of cutting across a portion of the inner wall layer 60 circumferentially to provide a desired width for a flap. Thus, the intimal layer separation mechanism 46 is not required in this embodiment for increasing a size of a previously created opening to create a flap with a desired width.

The sub-intimal access mechanism 18 that includes the rotational blade 240 may have different configurations in different embodiments. In one such embodiment, the blade 240 is linear instead of curved. In some embodiments, the blade 240 is supported by the rotary guide at some point along the shaft of the guide as opposed to at the distal end. In some such embodiments, the rotary guide can be removed from the conduit lumen 6 when the blade 240 is rotated to point inward toward the lumen 6 of the conduit mechanism 2. In other such embodiments, the rotary guide is longitudinally fixed but allowed to move laterally within the conduit lumen 6, effectively changing the axis of the blade rotation. In other such embodiments, the rotary guide is permanently fixed on the same rotational axis.

The previous embodiments were described with reference to using high-pressure contrast solution 10 to separate the layers (i.e. hydrodissection). However, in any of the embodiments described herein, alternate embodiments of the tissue layer separation mechanism may be used. In other embodiments, saline may be used. In further embodiments, a fluid based anti-thrombogenic agent may be used. In still further embodiments, water or another fluid may be used.

In any of the embodiments described herein, a shorter period of sustained hydrodissection may be used, in contrast to the 3-4 second duration described previously. In one such embodiment, the bolus of hydrodissection is sustained for a duration of 1-2 seconds. In another such embodiment, the bolus of hydrodissection is sustained for a fraction of a second.

A variety of embodiments have been described that utilize hydrodissection as the mechanism for tissue layer separation. In some such embodiments, hydrodissection is administered through the lumen 22 of the sub-intimal access mechanism 18. In other embodiments, hydrodissection can be administered through a hollow guidewire, needle or probe inserted through a previously created opening at the inner wall of the vessel. The following schematics depict different forms and utilizations of hydrodissector delivery mechanisms. As used in this specification, the term "hydrodissector delivery mechanism" or similar terms refer to the element that delivers pressurized fluid between tissue layers for the purpose of tissue layer separation.

Figure 27:
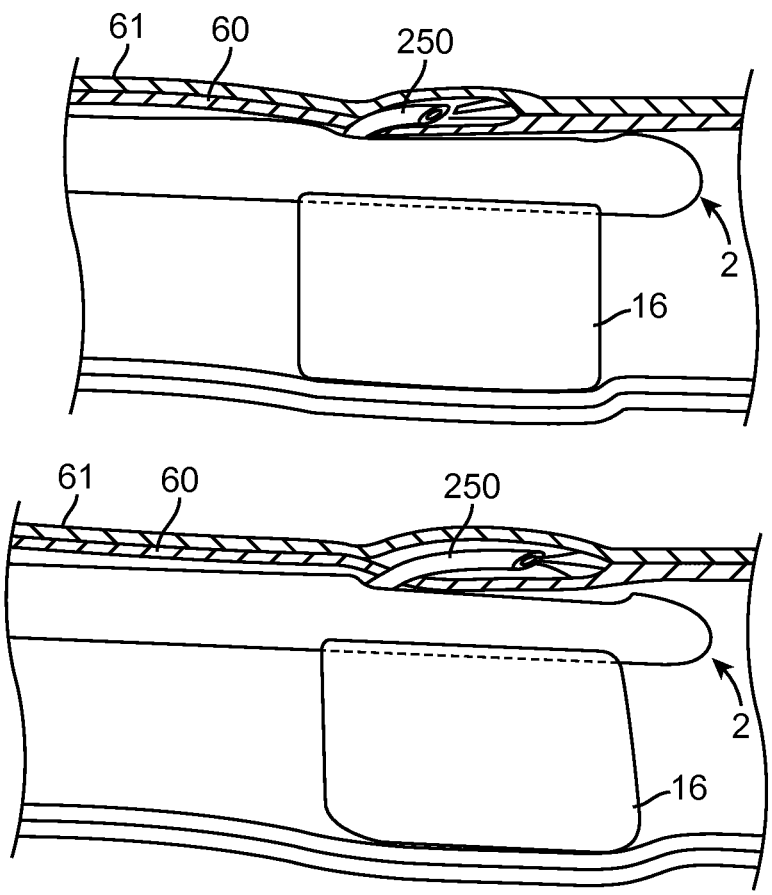
FIGS. 27-29 illustrate different hydrodissectors in accordance with different embodiments.

FIG. 27 depicts an embodiment of the hydrodissector delivery mechanism 250 of the tissue layer separation mechanism 18, which provides a volume of high-pressure fluid at the point of sub-intimal access. After the fluid is delivered, the hydrodissector delivery mechanism 250 is advanced into the inter layer plane so that a second hydrodissection can be performed to further separate the tissue layers. In this embodiment, such cycles of hydrodissection followed by hydrodissector delivery mechanism 250 advancement may be repeated as many times as needed. In other embodiments, the hydrodissector delivery mechanism 250 is advanced simultaneously during hydrodissection. In further embodiments, the hydrodissector delivery mechanism 250 is rotated during advancement while injecting pressurized fluid out of the exit port(s) at the mechanism 250. The hydrodissector delivery mechanism 250 may be any tubular structure, such as that with lumen 24, or any of the needles described herein.

Figure 28:
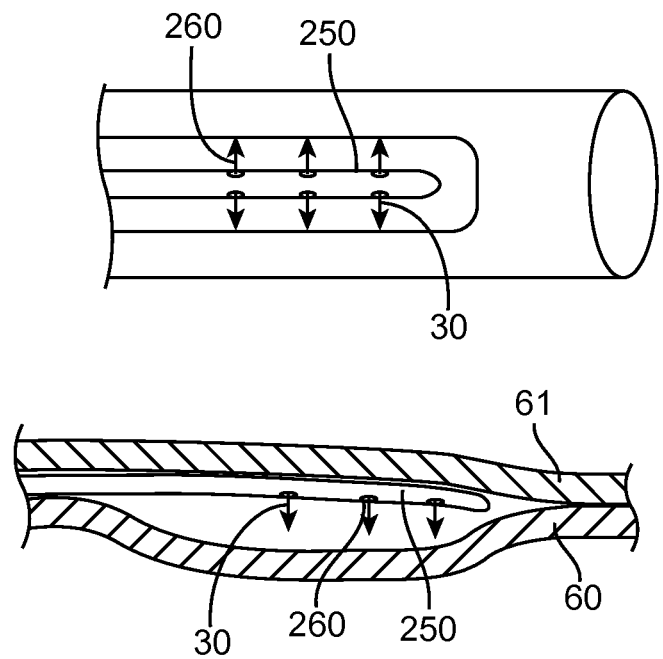
Figure 29:
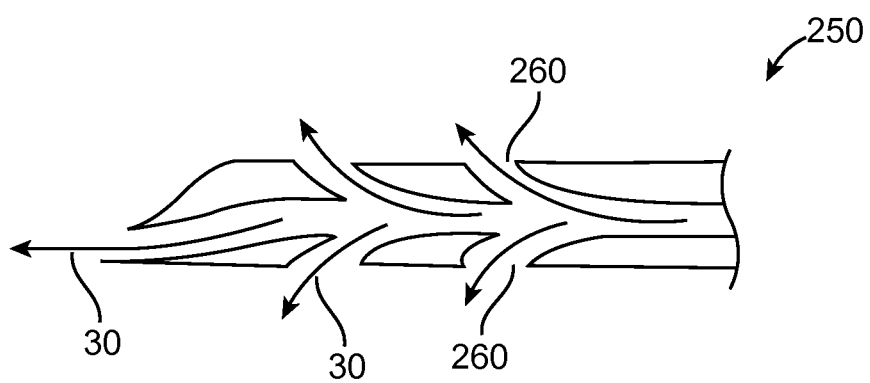

FIGS. 28 and 29 depict other embodiments, in which the hydrodissector delivery mechanism 250 contains multiple exit ports 260, which are strategically placed such that the stream of pressurized fluid 30 is directed along the intended direction of dissection to separate tissue layers. FIG. 28 depicts an embodiment, in which the hydrodissector delivery mechanism 250 is advanced lengthwise some distance into the sub-intimal space, close to parallel to the vessel wall. In this embodiment, the hydro-dissector 250 contains multiple sideways facing exit ports 260 along the opposite longitudinal sides of the hydrodissector delivery mechanism 250 (top figure). In other embodiments, the ports 260 may be located on one side of the hydrodissector delivery mechanism 250 (bottom figure). In the illustrated embodiments, the ports 260 are oriented so that they face towards the inner tissue layer side 60 (facing towards the center of the lumen). In this way, pressurized fluid 30 is forced sideways to create a greater width of inter-layer pocket. Additionally, the ports facing the center of the vessel lumen help to peal the inner tissue layer 60 away from the outer tissue layer 61. In any of the embodiments described herein, the hydrodissector delivery mechanism 250 may optionally further contain forward facing exit port(s), which point in the direction of dissection.

FIG. 29 depicts an embodiment in which the previously described sideways facing exit ports 260 are angled slightly in the direction of dissection as opposed to being perpendicular to the longitudinal axis of the hydrodissector delivery mechanism 250.

In any of the embodiments described herein, a hydrodissection control mechanism may be utilized to control the depth and width of tissue separation created by the hydrodissector delivery mechanism 250. The hydrodissection control mechanism regulates the flow-rate, flow-volume, flow duration, and/or pressure of flow of the hydrodissection fluid 10. These parameters can thus be tuned to create tissue separation at specific distances from a specific exit port. In one such embodiment, such parameters are controlled on the proximal end with an electronically incorporated valved system. In another such embodiment, such embodiments are regulated by a mechanical device near or at the exit ports 260. In some embodiments forward facing ports may have different sizes than side ports to impart different flow-rates in different directions. This will help to control the width and depth of the dissection pockets separately. The same principal may apply to side ports 260 facing the intima, and flow-rates may be controlled for functional or safety reasons. In some cases, it may be more clinically or technically feasible to have a hydrodissection that only has the force to dissect tissue in close proximity to the exit ports 260 themselves. In such embodiments, the movements of the hydro-dissector 250 can be controlled circumferentially and longitudinally to control the size and shape of the dissection pocket.

In any of the embodiments described herein, high-pressure gas may be used as the mechanism for the tissue layer separation. For example, in any of the embodiments described herein that utilize a form of hydrodissection for tissue layer separation, the hydrodissecting fluid 10 can be replaced by a pressurized gas. In these cases, the tissue layer separation mechanism 250 includes a source of gas, and a tissue layer separation actuator, which may be a manually (or machine) operated piston mechanism.

In any of the embodiments described herein, the tissue layer separation actuator may include a spring and piston mechanism as opposed to a manually driven piston mechanism. In other embodiments, the tissue layer separation actuator may include an electrically driven pump, such as a peristaltic pump.

In other embodiments, instead of using fluid to separate the layers 60, 61 at the vessel wall, a mechanical device may be used to physically separate the tissue layers. These embodiments create a controlled dissection in the inter-layer space by mechanically separating the tissue layers 60, 61 by advancing a probe forward within the space between the layers 60, 61. In these embodiments, the tissue layer separation mechanism is comprised of a dissection probe and an advancement mechanism.

FIG. 30 depicts an embodiment in which the tissue layer separation mechanism includes a dissection probe 280 that takes the form of a blunt, solid, stiff probe. The probe 280 is configured to peal apart tissue layers upon advancement. This embodiment utilizes previously achieved access (e.g., through a previously created opening at the vessel wall surface) to insure the correct depth is chosen. Such access is created by the sub-intimal access mechanism 18. In the embodiment depicted, the dissection probe 280 is fed into the inter layer plane through the lumen 24 of the sub-intimal access mechanism 18. This may be achieved through an actuation of an advancement mechanism at the proximal end.

FIG. 31 depicts an alternate embodiment in which the tissue layer separation mechanism includes a dissection probe 280 that takes the form of a blunt, solid, stiff probe, which acts to peal apart tissue layers upon advancement. The dissection probe 280 is advanced directly through the lumen 6 of the conduit mechanism 2 until it exits the sideways facing exit port 7 and enters a previously achieved access opening through the inner tissue layer 60. The probe 280 includes a delivery shaft 282 having a curved shape such that a specific path of advancement is taken upon exiting the conduit mechanism 2. In this embodiment, the sub-intimal access mechanism 18 is removed from the conduit mechanism 2 prior to actuation of the tissue separation mechanism 280. As depicted, this embodiment must utilize previously achieved access (e.g., opening) through the inner tissue layer 60 to insure the correct depth is chosen. Such access may be created by the sub-intimal access mechanism 18 in accordance with some embodiments.

Figure 32:
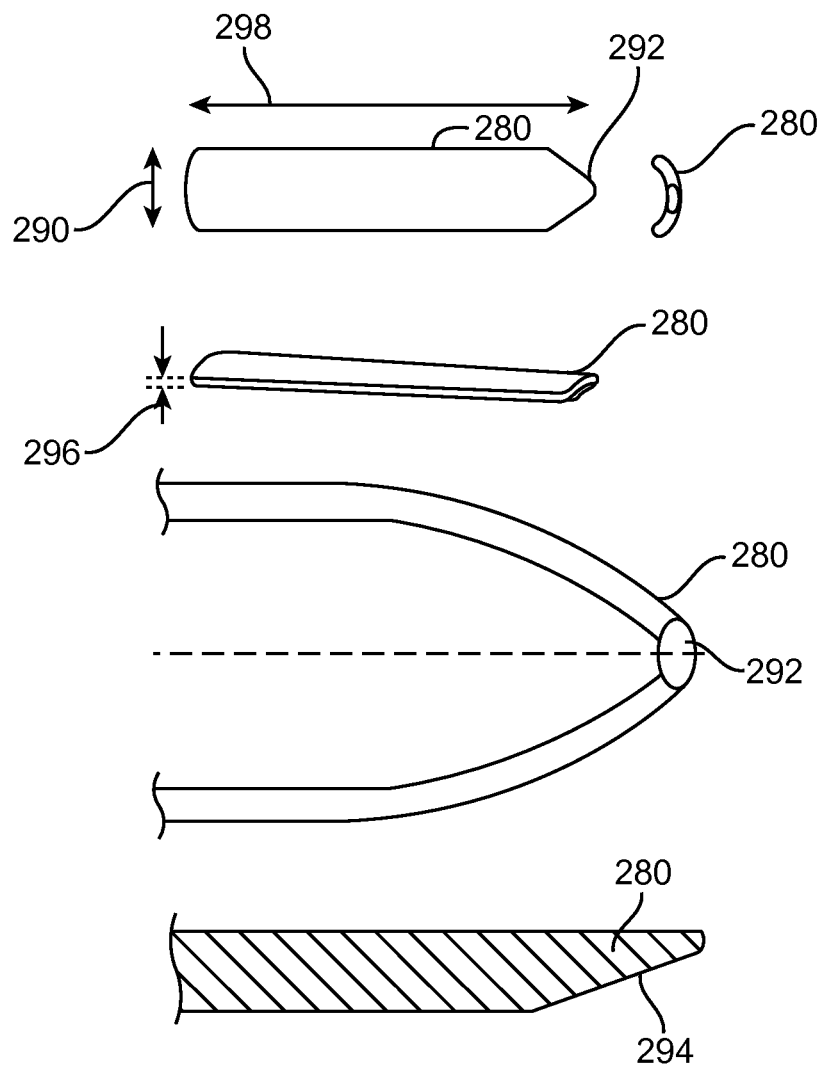

FIG. 32 depicts the blunt dissection probe 280 in accordance with some embodiments. The probe 280 is curved along the width dimension 290 to closely match the curvature of the taut vein wall. In this embodiment, the probe width 290 is between 0.1 mm and 10 mm. In more preferable embodiments, the probe width 290 is between 1 mm and 6 mm. In still more preferable embodiments, the probe width 290 is between 2 mm and 3 mm. In non-venous applications, or in large veins, the probe width 290 may be bigger than 10 mm. In the embodiment depicted, the distal most nose 292 of the probe is rounded in the width dimension, while a linear taper 294 extends from the rounded nose to the full width of the probe 280. In other embodiments the linear taper 294 is replaced by a curved chamfer. In the embodiment depicted, the probe thickness 296 is significantly smaller than the probe width 290. Additionally, there exists a gradual taper in the thickness dimension from the distal tip 292 of the probe 280 terminating at some distance from the distal tip 292 of the probe 280 with the full thickness of the probe. In the embodiment depicted, the probe's length dimension 298 is significantly longer than the width 290 and thickness dimensions 296. The probe 280 will have sufficient length 298 to create a narrow pocket sufficient for the necessary pocket depth of the valve to be created. In this embodiment, the probe length 298 is greater than the diameter of the bodily lumen, and is between 3 mm and 20 mm. In more preferable embodiments, the probe length 298 extends between 8 mm and 14 mm. In still more preferable embodiments, the probe length 298 extends between 10 mm and 12 mm. In another dissection probe embodiment, the probe has a radially symmetric shape, with the tip having a smaller diameter cross-section than the shaft, much like a cone.

In any of the embodiments described herein, the dissection probe 280 may have a sharp distal tip. In such cases, the probe 280 itself may be used to penetrate into the wall of the vessel. Thus, the use of the probe 280 does do not require previously achieved access through the inner tissue layer 60 to insure the correct depth is chosen, and thus constitute both the sub-intimal access mechanism and the tissue layer separation mechanism. In such embodiments, the dissection probe 280 may be fed into through the lumen 6 of the conduit mechanism 2, and out of the sideways facing exit port 7. The probe 280 may then be pushed toward the inner tissue layer 60. The dissection probe 280 then penetrates into the inner tissue layer 60, and is advanced into the inter layer plane between the layers 60, 61 at the vessel wall. This may be achieved through an actuation of an advancement mechanism at a proximal end.

Figure 33A:
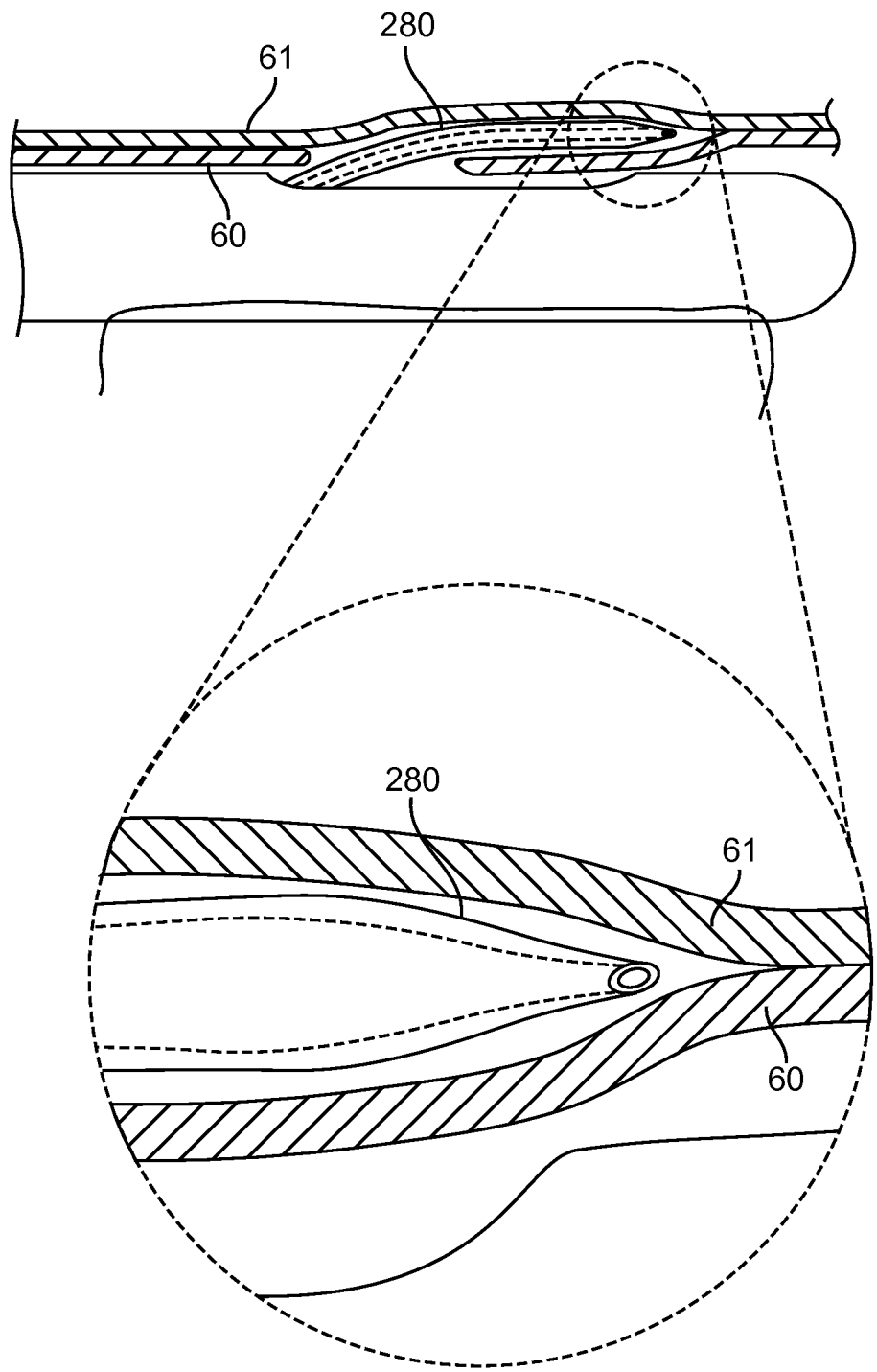
Figure 33B:
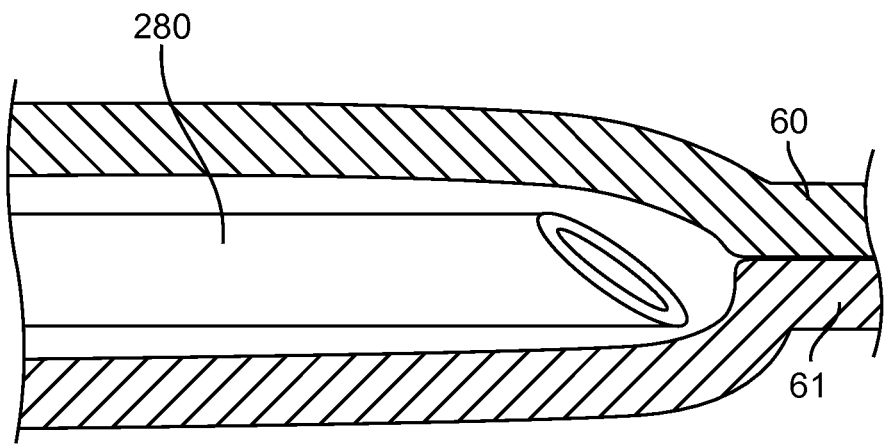
Figure 33C:
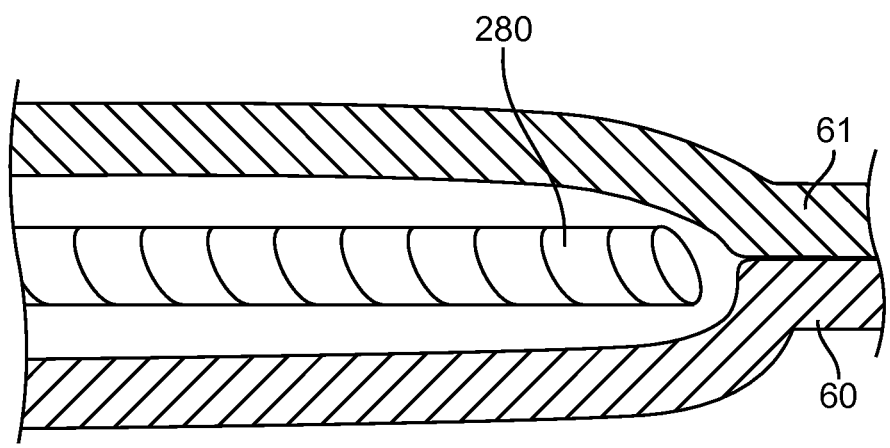

FIGS. 33a-33c depict different embodiments of a sharp dissection probe 280, with different geometries. The probe 280 may be advanced for use as a tissue layer separation mechanism.

FIG. 33a depicts an embodiment of the dissection probe 280 which takes the form of a hollow needle with a pencil point tip, which is configured to penetrate into the inner tissue layer 60, then is advanced forward to create a narrow dissection plane between the tissue layers 60, 61. The probe 280 has a radially symmetric taper from the full probe diameter down to the sharp tip, which keeps the sharp tip shielded from the inner layer 60 and outer layer 61 during advancement.

FIG. 33b depicts an embodiment of the dissection probe 280 which takes the form of a hollow needle with a beveled tip, which is configured to puncture the inner tissue layer 60. The probe 280 may be advanced forward to create a narrow dissection plane between the tissue layers 60, 61.

FIG. 33c depicts an embodiment of the dissection probe 280 which takes the form of a guidewire. The guidewire may puncture the inner tissue layer 60, and may be advanced forward to create a narrow dissection plane between the tissue layers 60, 61.

Figure 34:
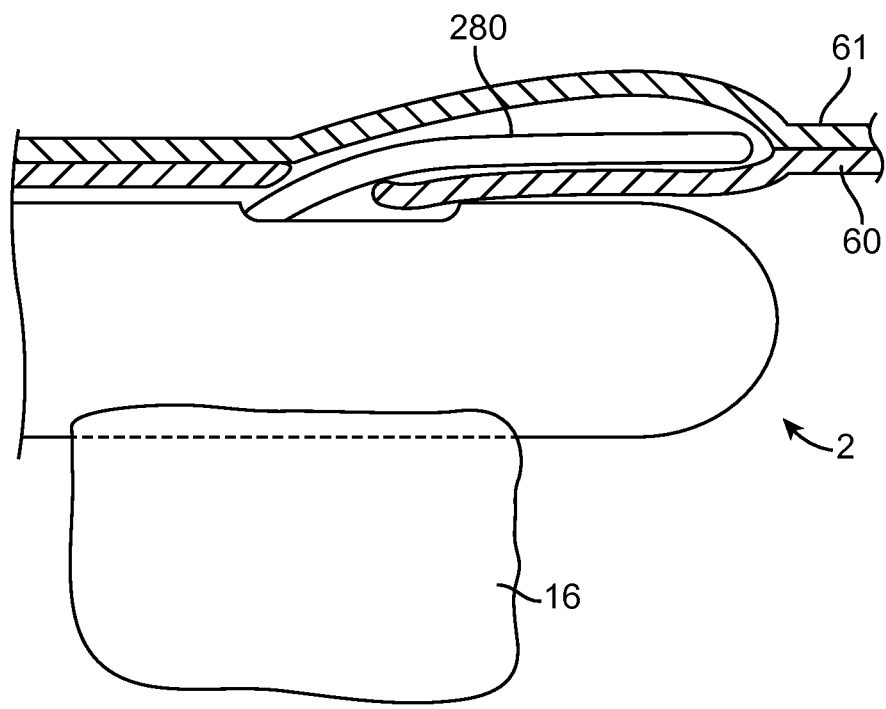

As illustrated in the previous embodiments described with reference to FIG. 31, the dissection probe 280 protrudes from the sideways facing exit port 7, but always remains within the longitudinal confines of the exit port 7. In the embodiment depicted, the probe 280 performs the dissection outside of the conduit mechanism 2, but along the length of the sideways facing exit port 7. In other embodiments, the probe 280 may be configured to perform dissection at other locations relative to the port 7. FIG. 34 depicts another embodiment, in which the dissection probe 280 extends out of sideways facing exit port 7, and past the side port 7. In the embodiment depicted, the probe 280 may perform the dissection outside of the conduit mechanism 2, but along the length of the sideways facing exit port 7, or along a side of the conduit mechanism 2, but distal to the sideways facing exit port 7, or distal to the conduit mechanism 2. The probe 280 may have a sharp or blunt tip.

Figure 35:
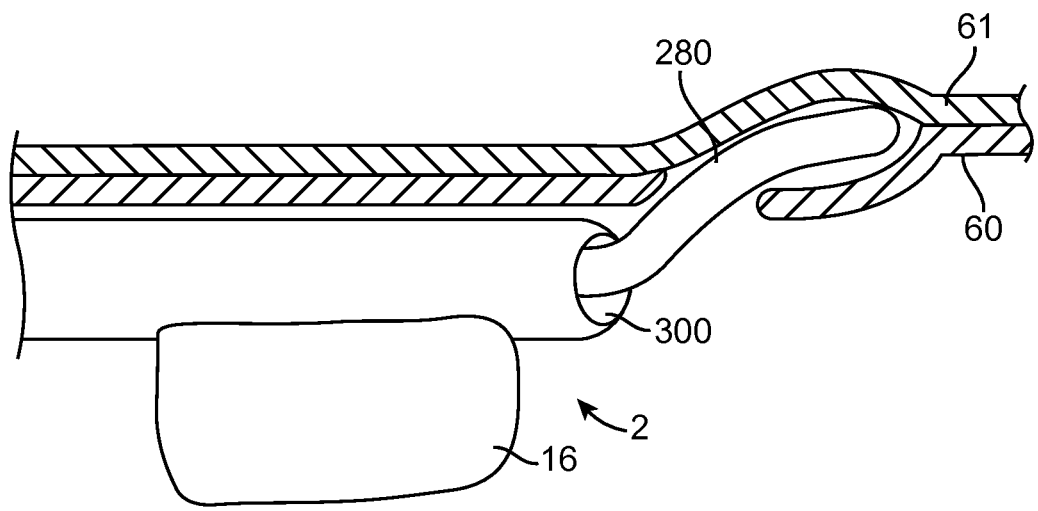
Figure 36A:
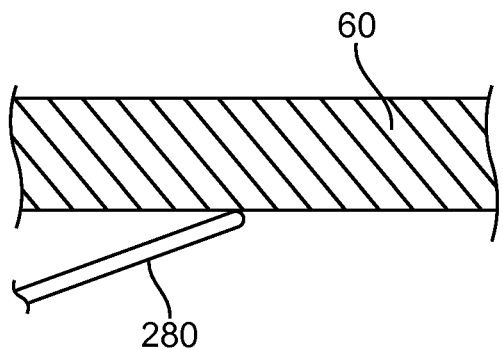
Figure 36B:
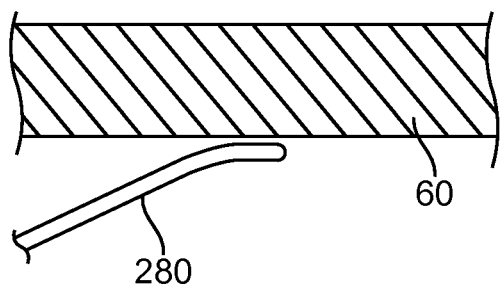
Figure 36C:
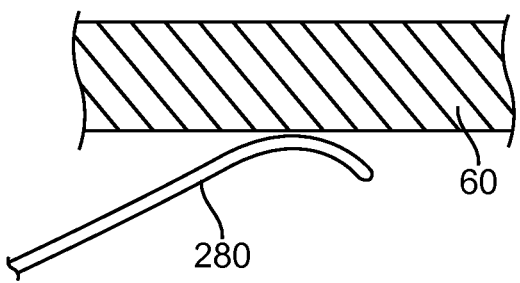
Figure 36D:
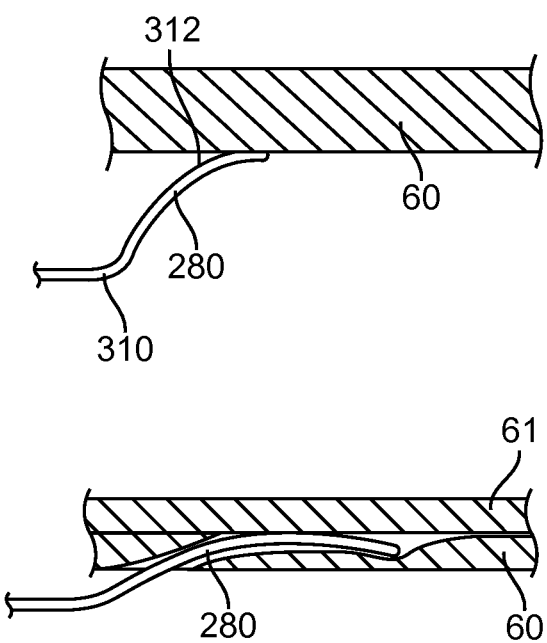

FIG. 35 depicts another embodiment, in which the dissection probe 280 is delivered out of an opening 300 at the distal tip of the conduit mechanism 2. The opening 300 is connected to the main lumen 6 of the conduit mechanism 2. In this embodiment, the probe 280 dissects through the tissue only beyond the distal tip of the conduit mechanism 2. The probe 280 may have a sharp or blunt tip.

In any of the embodiments described herein, the dissecting probe 280 may be constructed out of a shape memory alloy such as nitinol so that it may take a specified shape when exposed out of an exit port of the conduit mechanism 2.

FIGS. 36a-36d depict other embodiments of the dissection probe 280, particularly showing the probe 280 having different profiles along the length dimension 298 so that the probe 280 takes a specific path with the tissue as it exits the sideways facing exit port 7. In one embodiment depicted in FIG. 36a, the probe 280 is angled linearly, with a shallow/gentle angle, outward toward the inner layer 60 at the vessel wall. In another embodiment depicted in FIG. 36b, the dissection probe 280 is angled linearly outward toward the vessel wall along most of its length, but takes a curve close to the distal end of the probe 280, so that the distal section of the probe 280 is parallel or close to parallel to the direction of advancement (e.g., parallel with the taut lumen wall in the longitudinal direction). In another embodiment depicted in FIG. 36c, the dissection probe 280 takes a tight curve outward toward the vessel wall, but straightens out close to the distal end of the probe 280, and then curves back at the very distal most section of the probe 280. In such configuration, an intermediate portion of the probe 280 is parallel or close to parallel to the direction of advancement (e.g., parallel with the taut lumen wall in the longitudinal direction). In another embodiment depicted in FIG. 36d, the dissection probe 280 takes a double curvature, with a tight proximal curve 310 outward toward the vessel wall, and a second distal curve 312 slightly near the distal end of the probe 280. This configuration allows the probe tip 280 to first contact the tissue at an angle approximately parallel (e.g., within 10°) to the vessel wall. Then as the probe 280 is advanced and the full curvature 312 of the probe 280 exits the catheter, the tip begins to change angle toward the center of the vessel lumen. This embodiment allows for the probe 280 to gain access to the inter layer plane between layers 60, 61, but then helps to prevent full perforation of the vessel wall by not presenting the outer tissue layer 61 with an outward edge of the probe 280 during advancement. Additionally, this configuration helps to pull the inner tissue layer 60 inward and away from the outer tissue layer 61, assisting in the dissection.

Figure 37:
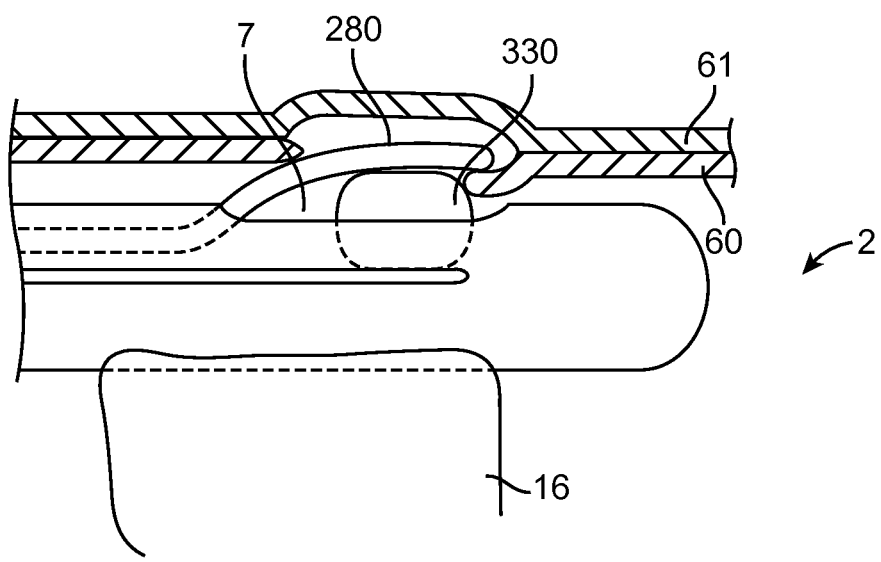

FIG. 37 depicts another embodiment in which an inflatable balloon 330 is used to push the dissector probe 280 laterally out of the sideways facing exit port 7 toward the vessel wall. The balloon 330 assists in guiding the probe 280 to penetrate into the vessel wall at a certain desired angle relative to the vessel wall. In other embodiments, an expandable Nitinol cage may be used to push the dissector probe 280 laterally toward the vessel wall.

FIG. 38 depicts another embodiment in which the dissector probe 280 contains a suction lumen 338, which communicates with a suction source 342 at the proximal end of the conduit mechanism 2. The probe 280 contains suction ports 340 on the inward-facing side 344 of the dissection probe 280, which communicate with the suction lumen 338. As the dissector probe 280 is advanced, the top most lip of the inner tissue layer 60 that has been recently separated from the outer tissue layer 61 will become temporarily adhered to the inward facing side 344 of the dissector probe 280 as it contacts the exposed suction port 340. As the dissection probe 280 is further advanced, the top lip of the inner tissue layer flap slides to other suction port 340 situated further down the length of the dissection probe 280. In other embodiments, multiple suction ports 340 are replaced by one continuous suction window. In further embodiments, the probe 280 may contain suction ports on the outward-facing side 350 of the dissection probe 280, which communicate with the suction lumen 338. When the probe 280 is advanced out of the sideways facing exit port 7 at the conduit mechanism 2, the suction forces at the side 350 of the dissector probe 280 forces the probe 280 towards the vessel wall so that dissection can occur in a controlled manner.

Figure 39:
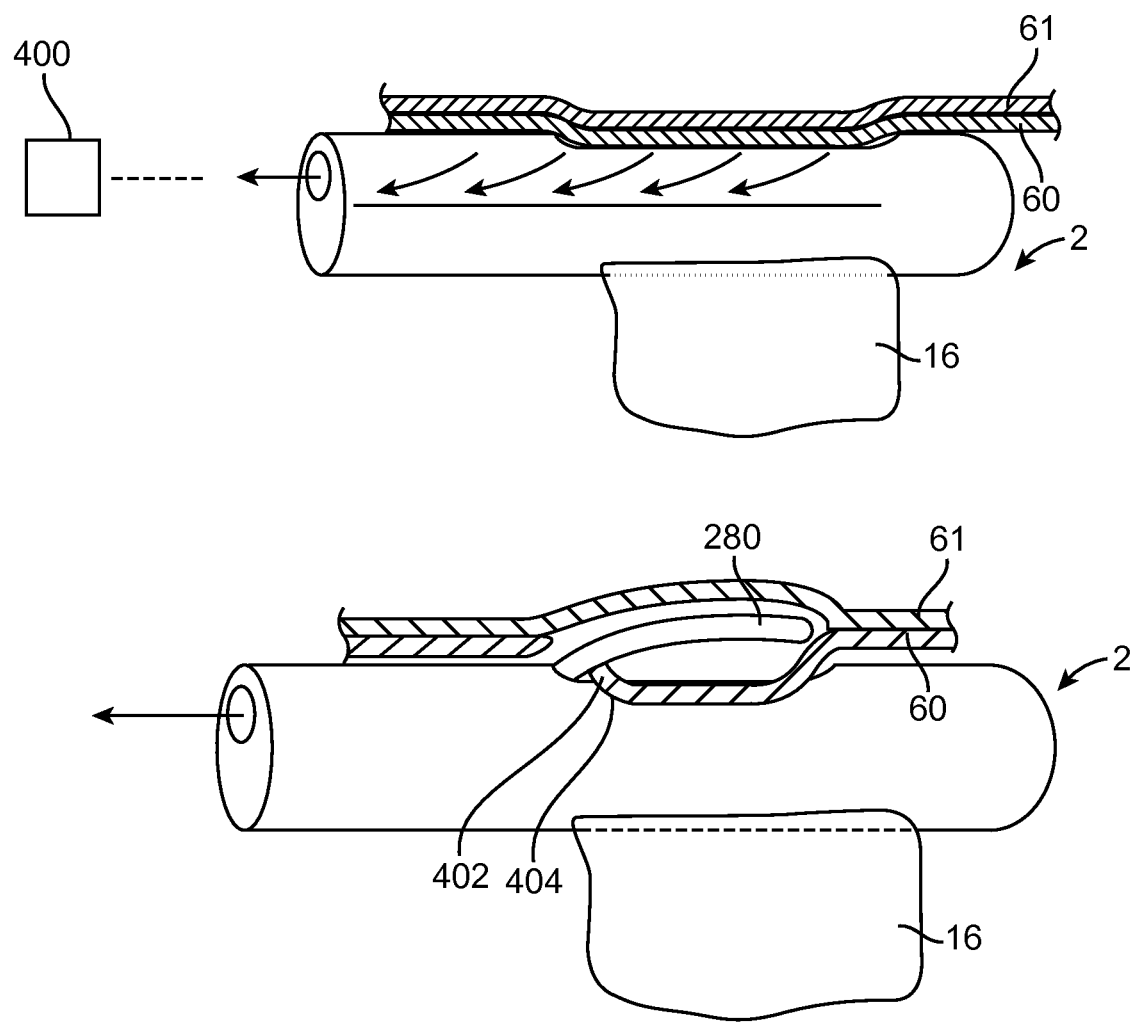
FIG. 39 illustrates a conduit mechanism with suction capability in accordance with some embodiments.

FIG. 39 depicts another embodiment in which the main lumen 6 of the conduit mechanism 2 is attached to a suction source 400. In this way, suction is imparted on the vessel wall through the sideways facing exit port 7. In this embodiment, an access opening 402 at the inner surface of the vessel wall was previously created by another device, and the suction is imparted on the top most lip 404 of the newly separated inner tissue layer 60. As depicted, a dissector probe 280 is then advanced out of the same sideways facing exit port 7 and into the inter layer plane through the access opening 402. The dissector probe 280 is then advanced further to perform a blunt dissection within the inter layer plane with the assistance of suction on the developing inner tissue layer flap, which helps by stabilizing the vessel wall relative to the device. In other embodiments, suction is used in the same manner, but the dissector probe 280 is advanced through the narrow lumen 24 of the sub-intimal access mechanism's 18 tissue engagement mechanism 23. In further embodiments, suction is used in the same manner, but no previously created access opening 402 is needed. In such cases, the probe may have a sharp distal tip for creating the access opening 402.

FIG. 40 depicts an embodiment in which a securement mechanism 410 is utilized in place of suction to maintain tension on the inner tissue layer flap 418 during blunt dissection by controlling the top most lip of the flap 418. In the embodiment depicted, a stitch 412 is placed through the top of the lip 418 just as it is first separated from the rest of the vessel wall. This suture 412 can be tensioned throughout the rest of the dissection or as needed to provide counter-tension during the dissection. In this embodiment, the stitch 412 may later be utilized as the securement mechanism 48, which attaches the flap 418 to another bodily structure (e.g., another wall portion) in the vessel lumen.

FIG. 41 depicts another embodiment in which a lip grabbing mechanism 420 is introduced to the vessel lumen. The mechanism 420 includes two cylindrical rollers 422, 424 separated by a small gap large enough to accommodate the thickness of the inner tissue layer flap 418. As depicted, the rollers 422, 424 are configured to both roll in opposite directions, toward each other, so that as they contact the vessel wall, they act to pull the inner tissue layer flap 418 between them. The backwards rotation of the distal roller 424 may be facilitated by a servomotor or other form of rotary motor. This can be utilized to provide the necessary tension for dissection. Some surface roughness is given to the rollers 422, 424 to aid in grabbing the tissue. As depicted, a jaw like mechanism 430 is utilized to grab the flap 418 once it is fed between the rollers 422, 424. In other embodiments, the rollers 422, 424 roll passively along the vessel wall in the same direction, until the flap 418 is fed between them.

Figure 42:
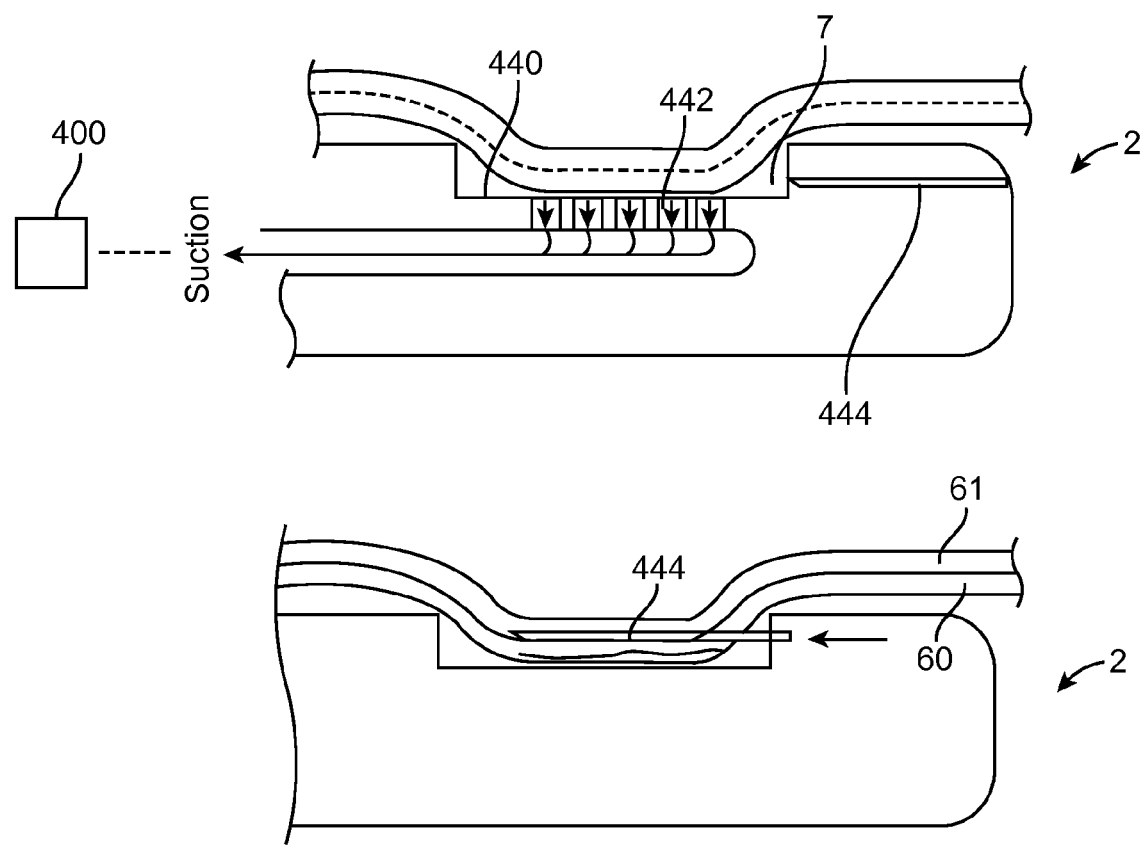
FIG. 42 illustrates a conduit mechanism that includes suction capability in accordance with some embodiments.

FIG. 42 depicts an embodiment in which the main lumen 6 of the conduit mechanism 2 is attached to a suction source 400. High powered suction imparted on the vessel wall through the sideways facing exit port 7 acts to pull the vessel wall a certain distance into the port 7. As depicted, a platform 440 exists within the conduit mechanism 2 to restrict the depth to which the vessel wall enters into the recess. Suction is maintained through ventilation holes 442 in the platform 440. In other embodiments, suction is maintained through a lack of sidewalls in the recess. Once the lumen wall is fully engaged with the platform 440, a sharp dissection probe 444 is forced downward, parallel or nearly parallel to the lumen wall, penetrating only to a specific depth within the wall based on the location of the moving probe 444 relative to the platform 440. In other embodiments, a blunt dissector probe may be used to separate the tissue layers 60, 61, after a sub-intimal access mechanism 18 has been utilized to provide an access opening at the inner wall of the vessel. In the embodiment depicted, the sideways facing exit port 7 has the shape of a long oval. In other embodiments, the port 7 may have the shape of a long rectangle. In other embodiments, sideways facing exit port 7 may have other geometries, such as a triangular or semi-circular shape, which will help to shape the inner tissue layer flap being created to a specific geometry.

Figure 43:
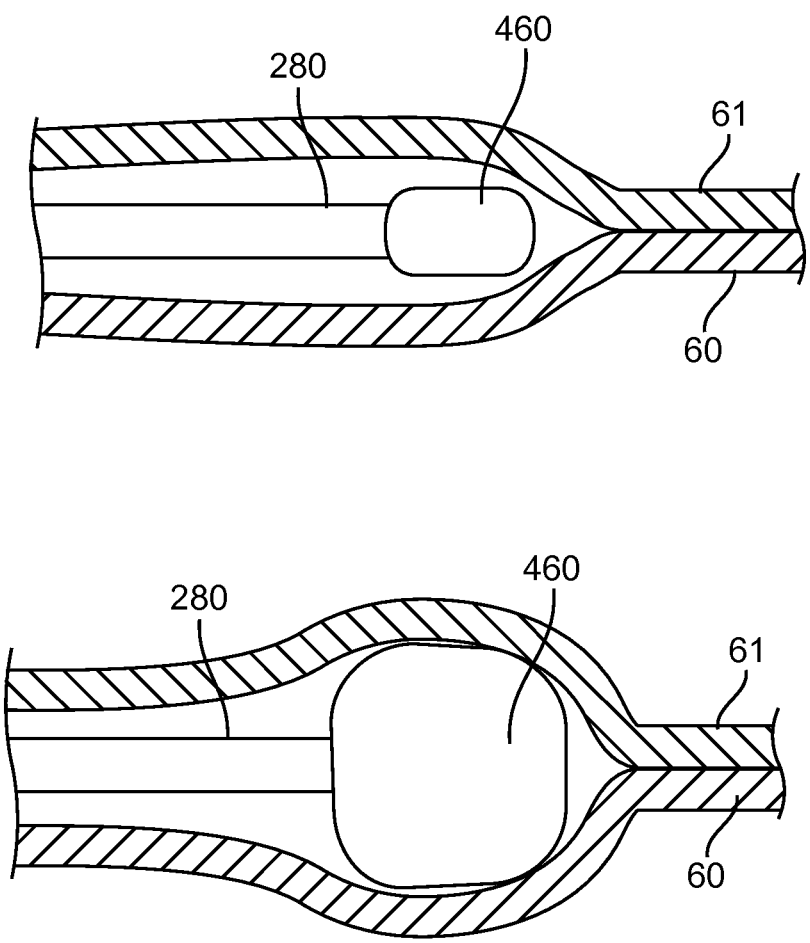
FIG. 43 illustrates a dissection probe with an actuatable portion in accordance with some embodiments.

FIG. 43 depicts another embodiment in which the distal end of the dissection probe 280 carries a very small inflatable balloon 460. The balloon 460 is inflated intermittently between probe advancements to peal the inner tissue layer 60 away from the outer tissue layer 61. In other embodiments, the balloon 460 is inflated during advancement of the probe 280.

FIG. 44 depicts another embodiment in which the distal end of the dissection probe 280 includes an actuating portion 470, which is rotatably coupled to the distal end of the probe 280 by a hinge 472. During use, the portion 470 may be rotated inward toward the center of the vessel lumen to separate the tissue layers 60, 61. In other embodiments, the distal end of the probe 280 may have jaws that open and close upon actuation, wherein the opening of the jaws is performed to separate the tissue layers 60, 61. The actuation of the inflatable balloon 460, actuating portion 470, or jaw may be performed manually by the user, or may be performed automatically based on advancement of the probe 280.

FIG. 45 depicts another embodiment in which the dissection probe 280 has the guide member 100 next to it, wherein the guide member 100 has a leading surface 480, which glides along the lumen wall ahead of the probe 280, to protect the tissue from taking a sharp angle with the dissection probe 280. In the embodiment depicted, the dissection probe 280 is curved and angled to protrude more than the leading surface 480, such that it may engage the inner tissue layer 60. The guide member 100 is made of a separate component than the dissection probe 280. In the depicted embodiment, the dissection probe 280 may exit through a port 482 in the guide member 100. In this depiction, the dissection probe 280 can be removed from the guide member 100 if needed (e.g., so that another device, such as a dilation balloon may be delivered through the port 482 for separating tissue). In other embodiments, the dissection probe 280 may contain the guide member 100 in a parascoping manner, both of which can be inserted or removed as desired. In further embodiments, the dissection probe 280 is a deformed portion of a cylindrical or near cylindrical tube, such that the portion of the tube or partial tube that is distal to the probe 280 forms the guide member 100.

In any of the embodiments that involve the dissection probe 280 described herein, the dissection probe 280 may be configured to advance with accelerated or high velocity motion to reduce the visco-elastic response of the tissue. The advancement of the tissue layer separation mechanism 280 may be accomplished with a spring force. In other similar embodiments, the advancement mechanism for advancing the tissue layer separation mechanism 280 may include a piston driven by a compressed gas or electrical motor, by a manual force, or other mechanism for creating the accelerated motion. FIG. 46 depicts an embodiment in which the dissection probe 280 is configured to oscillate (e.g., using an oscillator) laterally during advancement, either along a straight path or along a curved path that closely resembles the curvature of the inner vessel wall. In further embodiments, the dissection probe 280 is configured to intermittently bend or move slightly inward toward the center of the vessel lumen, either while advancing of the probe 280 or between intermittent advancement periods. This motion will act to pull the inner tissue layer 60 away from the outer tissue layer 61 in a non-traumatic manner. In other embodiments, the dissection probe 280 may be configured to rotate as it is advanced. In some such embodiments, the probe 280 may have a larger width than its thickness, so that upon rotation, the probe acts to peal the inner tissue layer 60 away from the outer tissue layer 61. In other embodiments, the dissection probe 280 may have a radially symmetric shape, and acts to burrow through the inter layer plane between the layers 60, 61 with rotational advancement. In further embodiments, the probe 280 may be configured to have a combination of some or all of these described motions. In any of the embodiments described herein that involves motion of the probe 280, the amplitude of the motions should be small and of relatively high frequency (especially for lateral vibrations). Lateral vibrations should preferably have an amplitude between 0.1 mm and 3 mm. Motions in which an object is pealing the inner tissue layer 60 perpendicularly away from the outer tissue layer 61 should have amplitudes between 0.5 mm and 5 mm.

FIG. 47 depicts another embodiment, in which a specific advancement motion is created automatically during advancement by the interference of strategically placed protrusions 500 on the dissection probe 280 and within the main lumen 6 of the conduit mechanism 2. As these protrusions 500, 502 pass over each other, they force the dissection probe 280 along a specific vibratory path. The vibratory path includes a component that is in the lateral direction perpendicular to the wall of the vessel. This facilitates in separating the tissue layers 60, 61 from each other.

Figure 48:
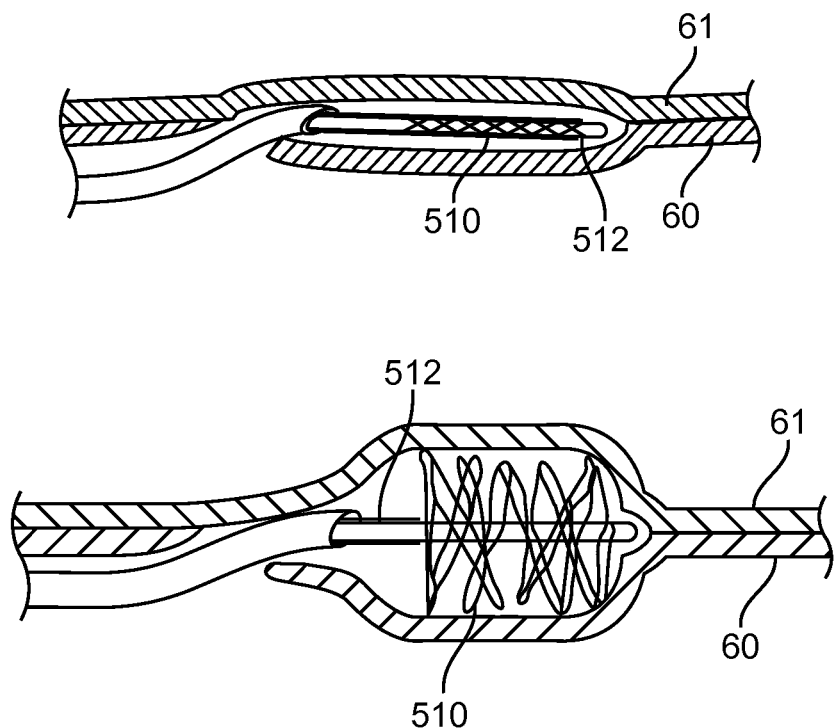
FIG. 48 illustrates a cage that may be used to create a pocket at a vessel wall in accordance with some embodiments.

The sub-intimal pocket creation mechanism 32 is not limited to the embodiments described previously, and may have different configurations in other embodiments. FIG. 48 depicts one such embodiment, in which the pocket creation balloon 38 of the sub-intimal pocket creation mechanism 32 is replaced by an expanding shape memory cage (e.g., Nitinol) 510 which is held closed prior to actuation by a constraining sheath 512. The sub-intimal pocket creation mechanism 32 is advanced through the main lumen 22 of the sub-intimal access mechanism 18, into the narrow lumen 24 of the tissue engagement mechanism 23, and out of the forward facing exit port 25. It is then advanced into the inter-layer plane (created by the mechanism 23) located between the inner layer 60 and the outer layer 61 of the lumen wall. It is advanced far enough such that the entire cage 510 is within the inter-layer plane. The constraining sheath 512 is then removed so that the expanding shape memory cage 510 expands to a specific geometry to create the appropriate sub-intimal pocket at the vessel wall.

Figure 49A:
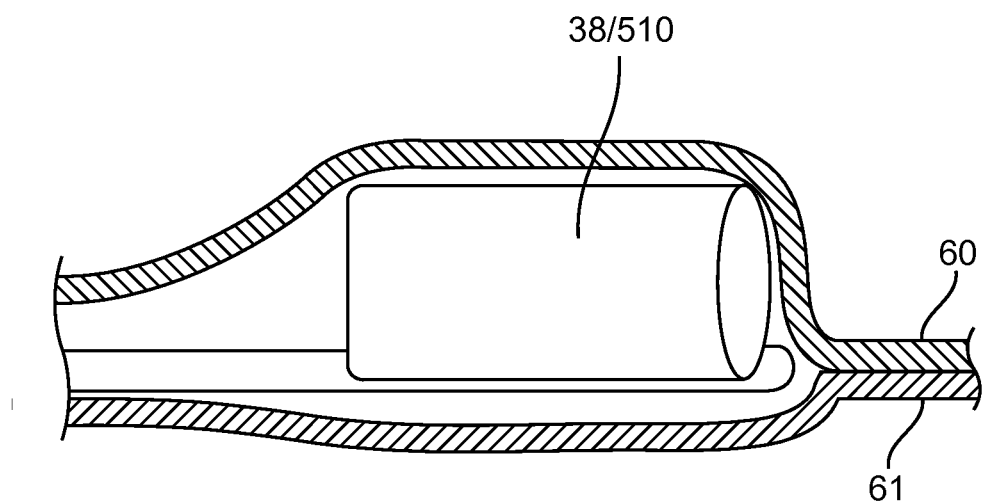
FIGS. 49a-49f illustrate different geometries for an expandable component of a sub-intimal pocket creation mechanism in accordance with some embodiments.
Figure 49B:
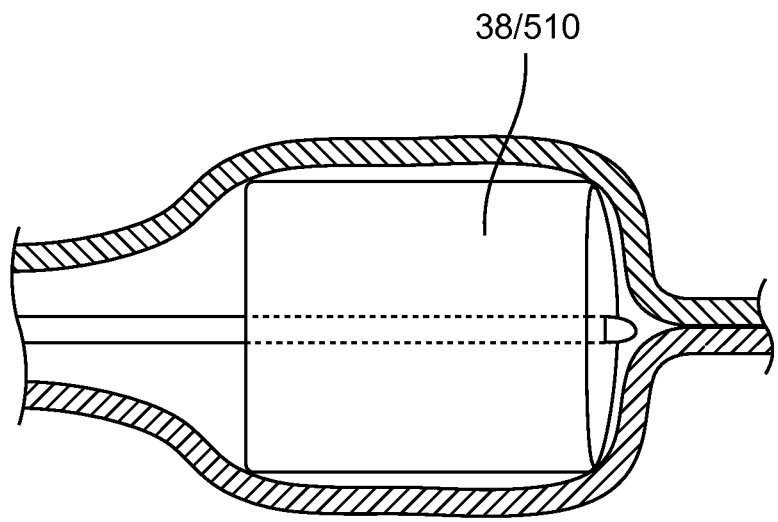
Figure 49C:
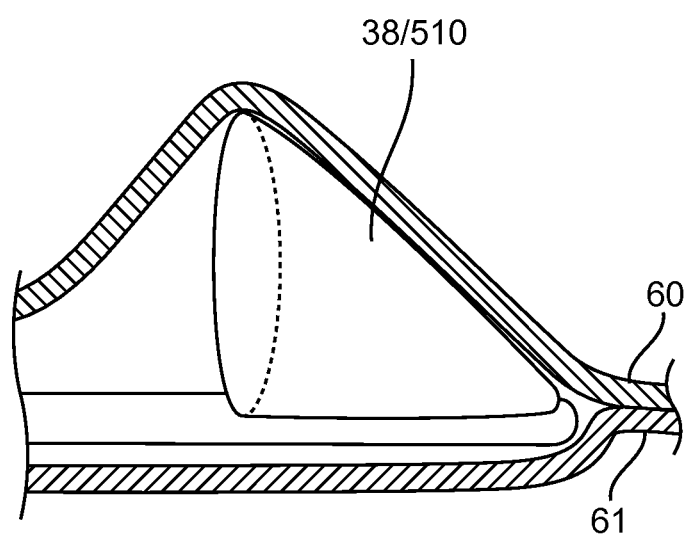
Figure 49D:
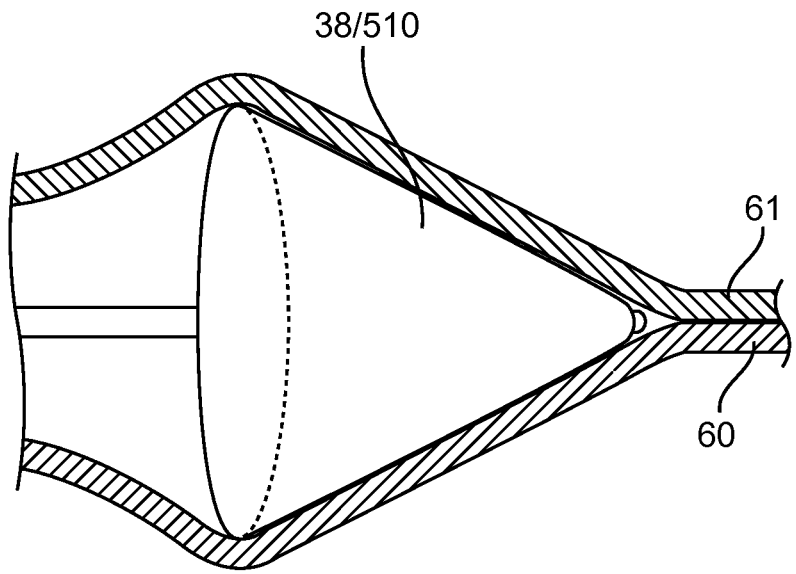
Figure 49E:
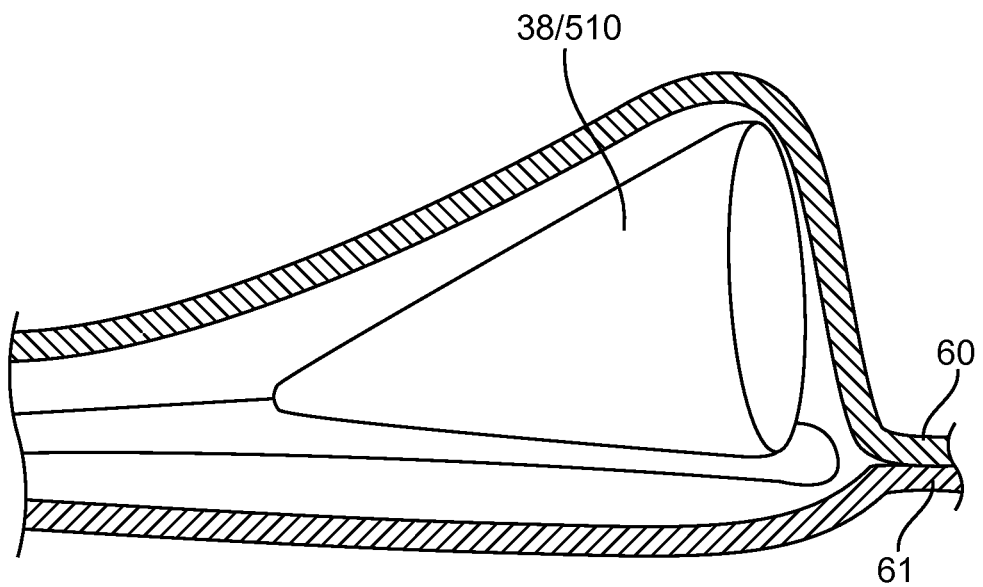
Figure 49F:
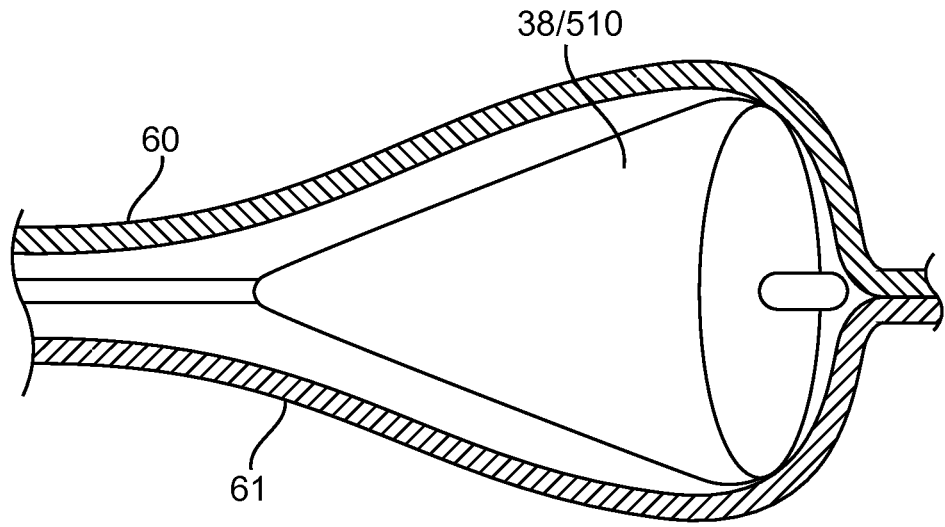

FIGS. 49a-49f depict different geometries for the expanding component (balloon or shape memory cage) of the sub-intimal pocket creation mechanism 32 in different embodiments. FIG. 49a depicts a geometry in which the expanding component 38/510 expands sideways from one side of the outer surface of the sub-intimal pocket creation mechanism 32, and is uniformly cylindrical. FIG. 49b depicts another embodiment in which the expanding component 38/510 expands symmetrically about a longitudinal axis of the sub-intimal pocket creation mechanism 32, and is uniformly cylindrical. FIG. 49c depicts a geometry in which the expanding component 38/510 expands sideways from one side of the sub-intimal pocket creation mechanism 32, and has a near triangular cross section, with the largest diameter being very proximal to the distal end of the mechanism 32. FIG. 49d depicts another embodiment in which the expanding component 38/510 expands symmetrically about the longitudinal axis of the sub-intimal pocket creation mechanism 32, and is of near triangular cross-section, with the largest diameter being proximal to the distal end of the mechanism 32. FIG. 49e depicts a geometry in which the expanding component 38/510 expands sideways from one side of the sub-intimal pocket creation mechanism 32, and has a near triangular cross section, with the largest diameter being very near distal end of the mechanism 32. FIG. 49f depicts a geometry in which the expanding component 38/510 expands symmetrically about the longitudinal axis of the sub-intimal pocket creation mechanism 32, and has a near triangular cross section, with the largest diameter being very near distal end of the mechanism 32.

Figure 50:
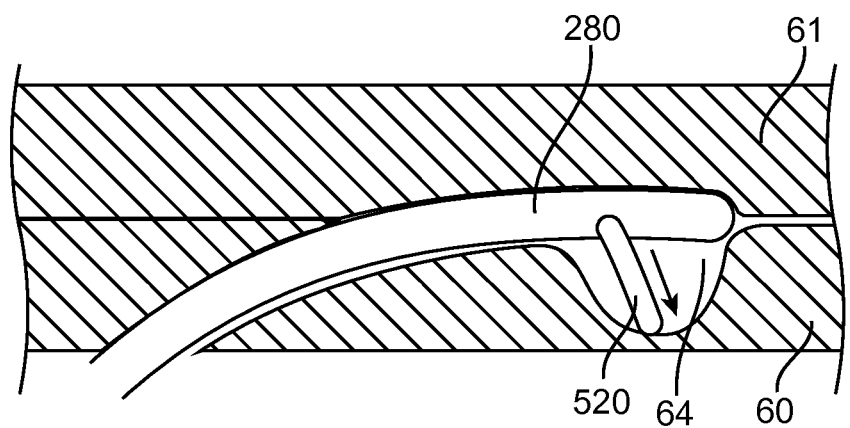
FIG. 50 illustrates another dissection probe having an actuatable portion in accordance with other embodiments.

FIG. 50 depicts another embodiment that utilizes a piston like member 520 which is inserted into the inter-layer dissection plane through the dissection probe 280, and is actuated to move laterally. It is then actuated to move toward the opposite side of the vessel lumen to peal apart the tissue layers 60, 61, to create the full dissection pocket 64. In other embodiments, a lever arm may be used as the sub-intimal pocket creation mechanism 32. The lever arm is inserted into the inter-layer dissection plane created by the tissue layer separation mechanism 28. It has the ability to move laterally within the plane when actuated from the proximal end. It can also be actuated to move toward the opposite side of the vessel lumen to peal apart the tissue layers 60, 61, to create the full dissection pocket 64.

In another embodiment, a temperature dependant expandable cage is used to separate the layers 60, 61. In such an embodiment, the device is inserted into the inter-layer dissection plane at a temperature distinguishably warmer or cooler than body temperature. Upon insertion, the cooling or heating of this element by the body, acts to transform the shape of the object into an expanded form, acting to complete the dissection pocket 64. In yet another embodiment, further blunt dissection is done in and around the previously created inter-layer plane to create the full dissection. In yet another embodiment, hinged jaws are used within the pocket to open up to create the full dissection. In some such embodiments of methods and devices for supplementing a previously narrow dissection pocket with continued dissection, the device described to carry out this function (i.e. balloon, NiTi cage, piston, actuating tip, jaws, fluid, etc) may be housed within, passed through, or passed over the sub-intimal access mechanism 18. In other embodiments, this device may be housed in a separate device, and is fed directly through the main lumen 6 of the conduit mechanism 2. In other embodiments, this device may be fed directly into the inter-layer plane without using the conduit mechanism 2.

Figure 51:
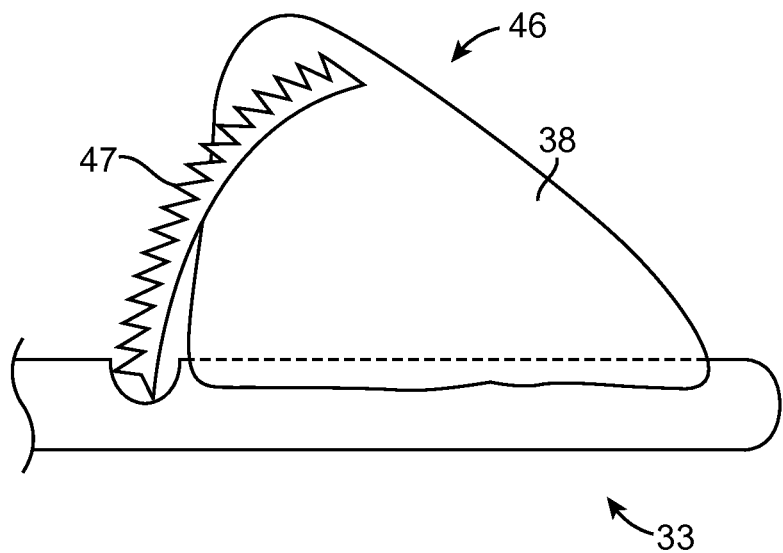
FIG. 51 illustrates a cutting mechanism in accordance with some embodiments.

The intimal separation mechanism 46 is not limited to the configurations described previously. FIG. 51 depicts another embodiment of the intimal separation mechanism 46, in which the backwards-facing cutting mechanism 47 is comprised of a backward facing serrated blade instead of a wire, which protrudes from the shaft of the pocket creation mechanism 33. This embodiment would be used in the same way as the embodiment described previously, in that it will be deployed with the expansion of the pocket creation balloon 38, and used to separate the inner tissue layer 60 upon retraction of the expanded balloon 38 through the narrow inlet (e.g., the one created by the sharp tip 27 of the tissue engagement mechanism 23) at inner surface of the vessel wall when the pocket creation mechanism 33 is removed. As similarly discussed, the cutting mechanism 47 cuts away from the narrow inlet as the balloon 38 is removed from the created pocket, thereby increasing the size of the inlet to provide a flap end with a desired width. In other embodiments, the cutting mechanism 47 may include a tapered blade. In further embodiments, the cutting mechanism 47 may include two overlapping, scissor like blades.

Figure 52:
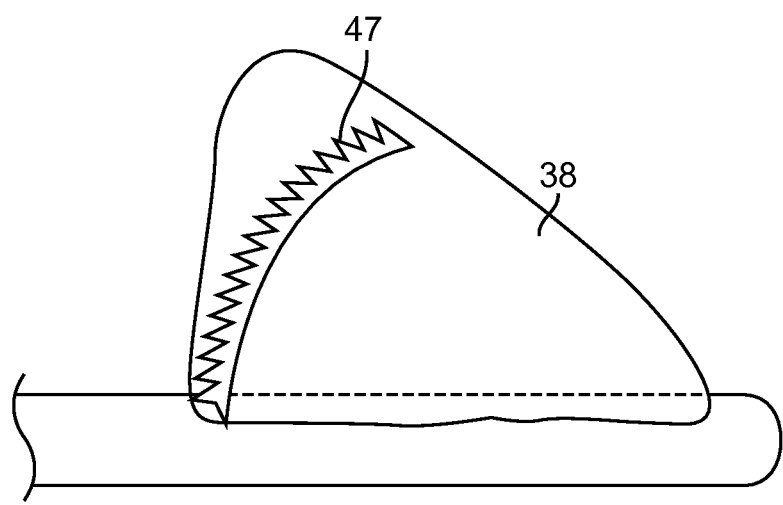
FIG. 52 illustrates another cutting mechanism in accordance with other embodiments.

FIG. 52 depicts another embodiment in which the backwards facing cutting mechanism 47 is attached to the expanding pocket creation balloon 38 itself as opposed to the shaft of the pocket creation mechanism 33. In other embodiments in which the expanding NiTi or shape memory cage is utilized as the tissue layer separation mechanism 28, and the backwards-facing cutting mechanism 47 is attached to the back-side (proximal end) of the cage to accomplish the intimal separation. In further embodiments, the expanding cage itself has a sharp backside, which acts to cut the inner tissue layer 60 along an intended geometric path.

FIG. 53 illustrates another embodiment in which the intimal separation mechanism 46 is embodied within the sub-intimal access mechanism 18. In this embodiment, the tissue engagement mechanism 23 of the mechanism 18 has sharp surfaces 550 on both sides, so that movement (e.g., rotation) of the sub-intimal access mechanism 18 will cause the sharp surfaces 550 to cut the inner layer tissue 60 with which the tissue engagement mechanism 23 is already in contact. As shown in the figure, the inner surface of the vessel wall has an opening 552 that was created by the sharp distal tip 27 of the mechanism 23 (or by another device). Movement of the mechanism 23 will cause the sharp edges 550 to cut away from the opening 552 to thereby increase the size of the opening 552. In some embodiments, the user may rotate the sub-intimal access mechanism 18 or move it laterally side to side while the pocket-creation balloon 38 is inflated within the sub-intimal pocket 64.

Figure 54C:
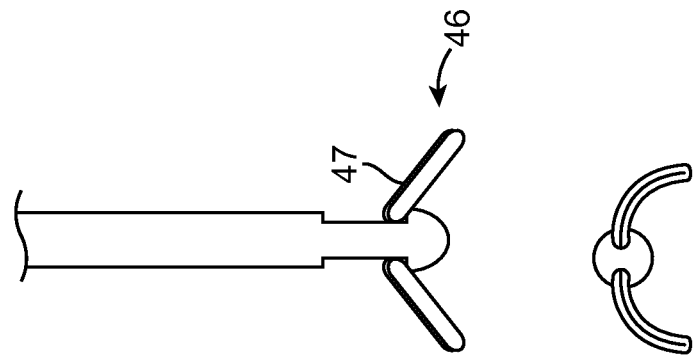
FIGS. 54a-54c illustrate different geometries for an intimal separation mechanism in accordance with different embodiments.
Figure 54B:
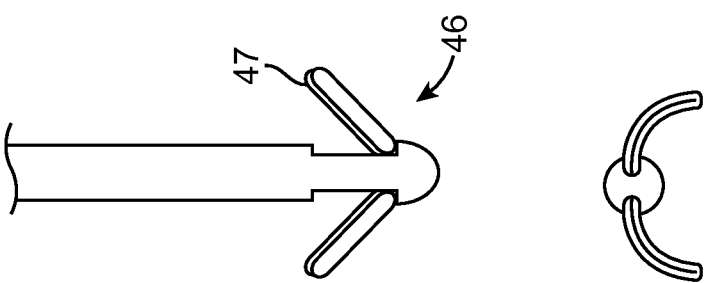
Figure 54A:
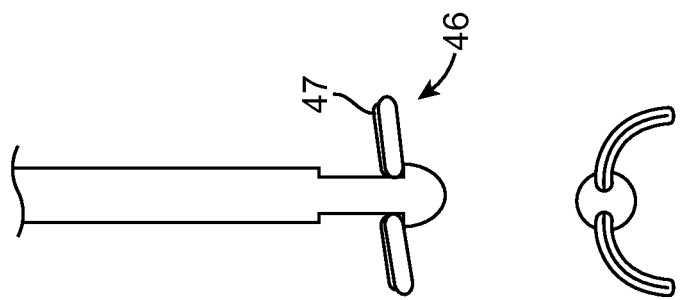

FIGS. 54*a*-54*c* depict how different embodiments of the intimal separation mechanism 46 can produce a different path of intimal separation, which dictates the geometry of the newly created intimal leaflet. FIG. 54*a* depicts an embodiment of a backwards-facing cutting mechanism 47 that creates a horizontal line of intimal separation (perpendicular to the lumen wall). FIG. 54*b* illustrates a backwards-facing cutting mechanism 47 that creates a line of intimal separation that is angled such that the center of the separation is at the highest point on the vessel wall, and the two endpoints of the separation (cut) occur lower than the center of separation, and are near the same height as each other. FIG. 54*c* depicts an embodiment of a backwards-facing cutting mechanism 47 that creates a line of intimal separation that is angled such that the center of the separation is at the lowest point on the vessel wall, and the two endpoints of the separation occur higher than the lowest point, and are near the same height as each other. All of these alternate device embodiments are used in a similar way as that described previously with reference to the intimal separation mechanism 46 of FIGS. 5*a* and 5*b*, which involves removal of the actuated intimal separation mechanism 46 from the newly created sub-intimal pocket. In some embodiments, the circumferential length of such a separation line is between 90° and 330°. In more preferable embodiments, the circumferential length of such a separation line is between 160° and 240°. In still more preferable embodiments, the circumferential length of such a separation line is between 190° and 220°. In the case of bicuspid valves or other multi-cuspid valve geometries, the circumferential length may be reduced accordingly by near proportional values (i.e. bicuspid length is about half the monocuspid length).

In any of the embodiments described herein, a cutting mechanism (e.g., a blade) may be used to cut the inner tissue layer 60 prior to dissection of the inner tissue layer 60 from the outer tissue layer 61. In some such embodiments, the blade action is utilized prior to dissection of the intima from other layers of the lumen to make a full intimal separation to the desired width of the valve. In some such embodiments, the blade action is utilized prior to dissection of the intima from other layers of the lumen to create a narrow incision, and then used again following dissection to increase the size of the incision to create the full width for the flap.

In any of the embodiments described herein, after the pocket creation mechanism 32 has been used to create the pocket, the pocket creation mechanism 32 (inflated balloon or expanded cage) may be forcefully removed through the narrow inlet 65 of the newly created intimal pocket 64, thereby tearing tissue to increase the size of the inlet 65. The increased size of the inlet 65 provides the flap with a desired width. In such cases, the cutting mechanism 47 may not be needed.

Figure 55A:
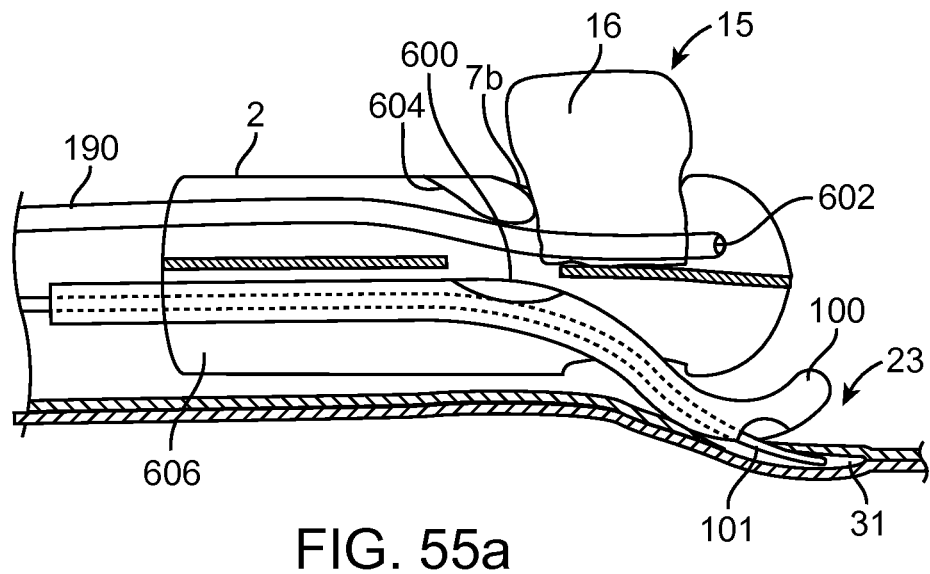
FIGS. 55a-55c illustrate another autologous valve creation system, and a method of using such system in accordance with other embodiments.
Figure 55B:
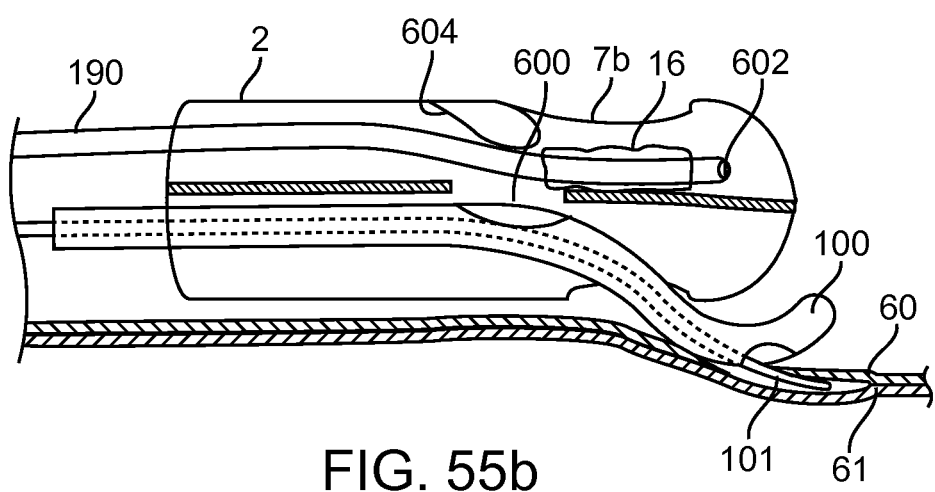
Figure 55C:
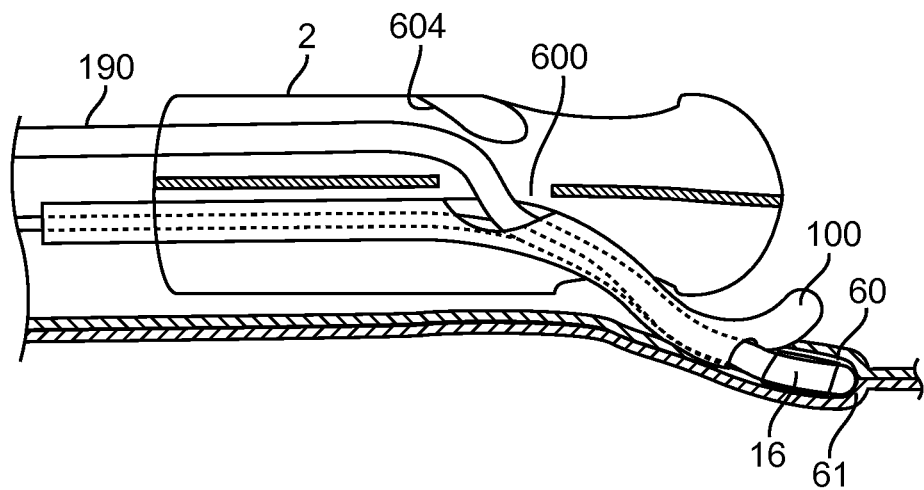

FIGS. 55*a*-55*c* depict another valve creation system in accordance with other embodiments. FIG. 55*a* depicts the system in its first stage of actuation. As shown in the figure, the conduit mechanism 2, has within it a connection portal 600 between the two main lumens. The wall-tensioning mechanism 15 includes a balloon 16 supported on an independent guide 190. In the illustrated embodiments, the tissue engagement mechanism 23 includes a needle 101 that protrudes a small amount from the surface of a larger guide probe 100, which acts as a leading edge (as previously described). In the illustrated embodiments, the balloon guide 190 has a track 602 on the side of its surface, sized appropriately to be able to connect to, and slide over the shaft of the tissue engagement needle 101. FIG. 55*a* depicts the wall-tensioning balloon 16 when it is inflated out of a side port 7*b* at the conduit mechanism 2 during tissue engagement by the needle 101, and during tissue layer separation. FIG. 55*b* depicts the balloon 16 after deflation. The balloon guide 190 is then retracted a small amount, and then re-advanced. FIG. 55*c* depicts the balloon 16 and balloon guide 190 after it has been advanced through the connection portal 600 with assistance from a directioning mechanism 604, which is present to force the balloon 16 to cross over to the tool lumen 606. Upon crossing into the tool lumen, the off-center balloon guide track 602 engages the shaft of the tissue engagement mechanism 101 and is advanced along the shaft until it extends past the distal end of the tissue engagement mechanism 23 and into the inter-layer space 31 that has been created between the vessel layers 60, 61 (as shown). The wall-tensioning balloon 16 is then inflated to create a pocket in the vessel wall. Thus, the same wall-tensioning balloon 16 may function as the pocket creation balloon 38, and has the appropriate geometry to create a sub-intimal pocket 64 (not depicted). In some embodiments, the independent balloon guide 190 may optionally have on it a backwards facing cutting mechanism 47 (not depicted) as well as a securement mechanism 48 (like that shown in FIG. 6) built in, to complete the intimal separation and the valve securement (for securing the valve against a vessel wall, or for securing two valves together).

Figure 56A:
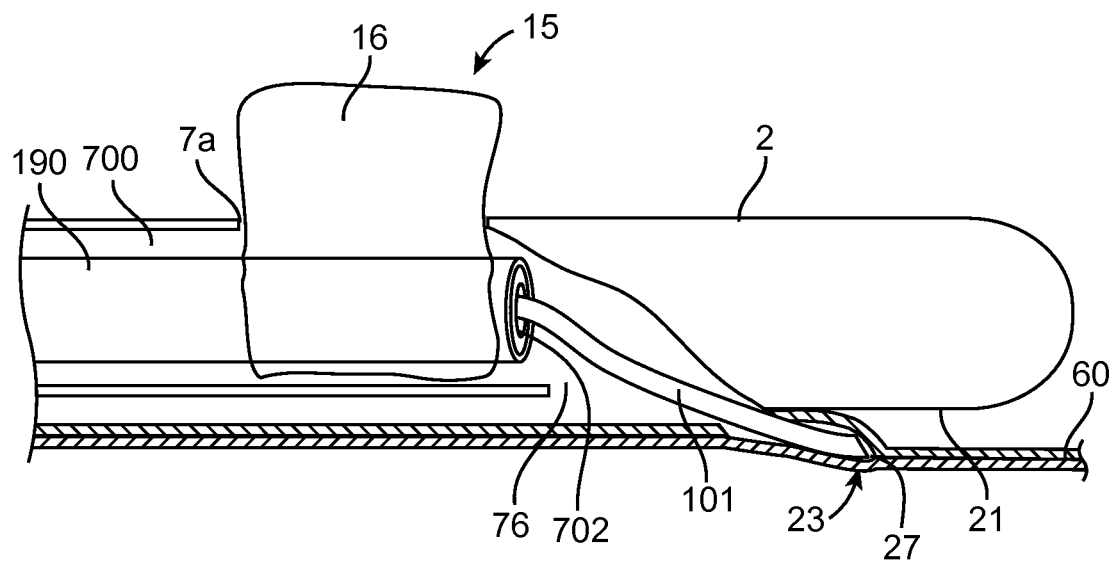
Figure 56B:
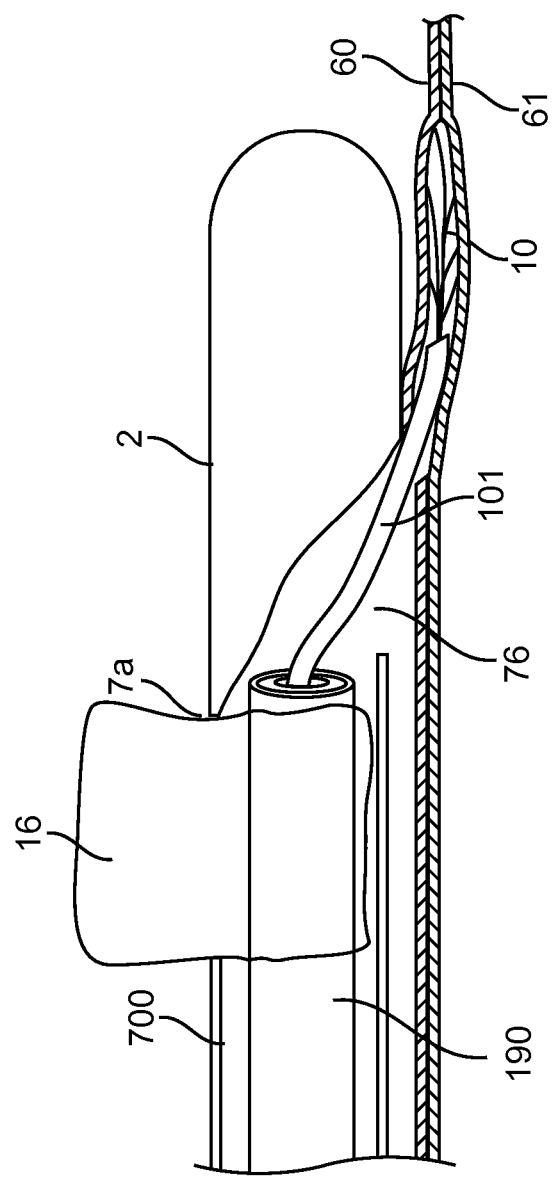
Figure 56C:
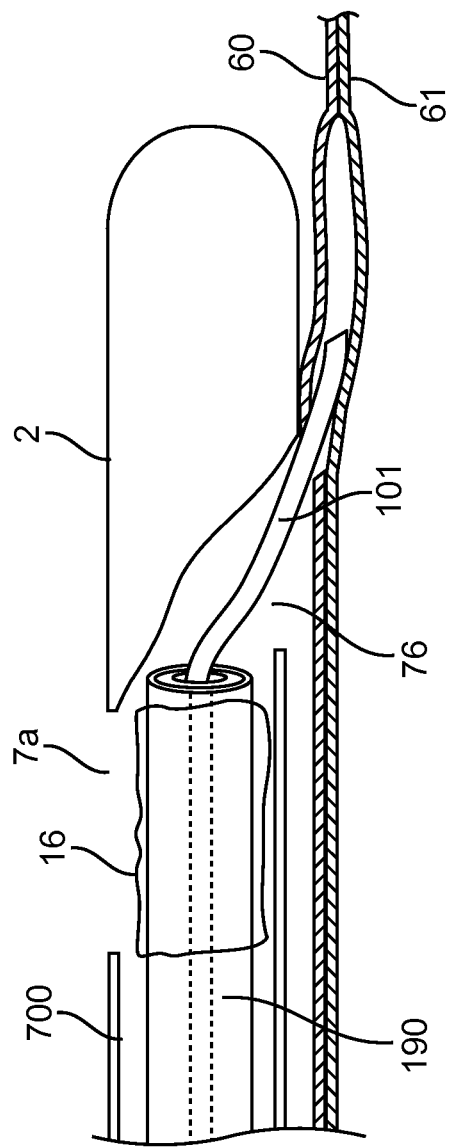
Figure 56D:
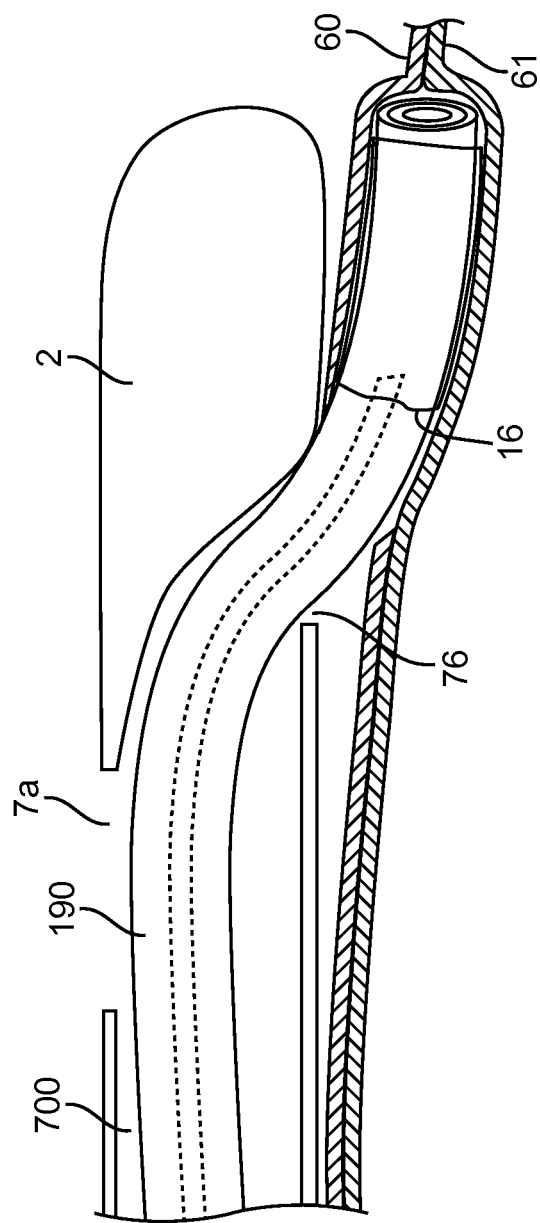
Figure 56E:
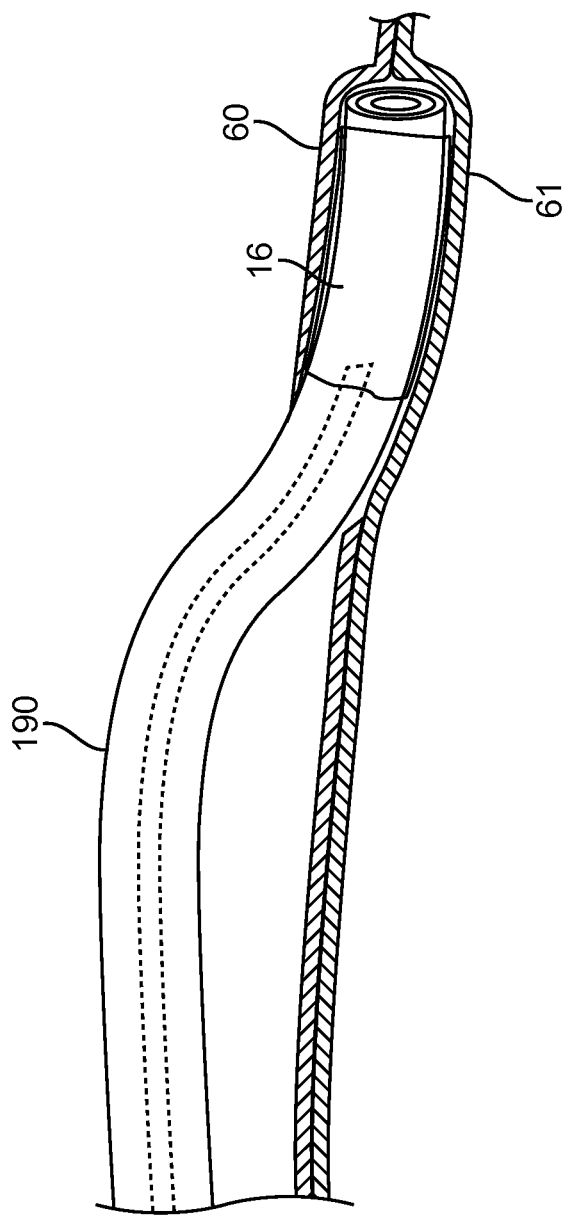

FIGS. 56*a*-56*f* depict another valve creation system in accordance with other embodiments. In the illustrated embodiments, the conduit mechanism 2 only has one lumen 700 and has two sideways facing exit ports 7*a* and 7*b* on opposite sides of the conduit mechanism 2. The wall-tensioning mechanism 15 includes a balloon 16 on an independent guide 190 (as previously described). This independent guide 190 has within it an inflation lumen for the balloon 16, and a tool lumen 702 through the middle. The tissue engagement mechanism 23 includes a needle 101 with a beveled tip 27 that is sized appropriately to fit through the lumen 702 of the independent balloon guide 190. FIG. 56*a* depicts the wall-tensioning balloon 16 after it has been inflated through one sideways facing exit port 7a, while the tissue engagement mechanism 101 is advanced through the lumen 702 of the independent balloon guide 190 and extends a small controlled amount out of the other sideways facing exit port 7b. The tissue engagement mechanism 23 can thus be engaged into the inner tissue layer 60 with the surface of the conduit mechanism 2 acting as the guide member 100. FIG. 56b depicts the needle 101 of the tissue engagement mechanism 23 delivering fluid 10 to dissect tissue in the vessel wall (i.e. hydrodissection), creating an inter layer plane 31. FIG. 56c depicts the wall-tensioning balloon 16 after it is deflated. FIG. 56d depicts the wall-tensioning balloon 16 when it is advanced along the tissue engagement mechanism needle shaft 101, advanced out of the sideways facing exit port 7b, and into the inter layer plane 31. FIG. 56e depicts the system after the conduit mechanism 2 has been removed, leaving the wall-tensioning balloon 16 in the inter-layer plane 31. FIG. 56f depicts the wall-tensioning balloon 16 after it is inflated again to create the pocket. In some embodiments, the independent balloon guide 190 may optionally have on it a backwards facing cutting mechanism 47 (not depicted) as well as a securement mechanism 48 (like that shown in FIG. 6) built in, to complete the intimal separation and the valve securement (for securing the valve against a vessel wall, or for securing two valves together).

It should be noted that any of the features described with reference to a figure or embodiment(s) may be combined with any other embodiments described herein. Also, in any of the embodiments described herein, one or more of the aspects may be omitted. For example, in other embodiments, the valve securement mechanism 48 is not needed, and the valve creation method does not include the act of securing the flap to a vessel wall portion. In addition, in any of the embodiments describe herein the valve creation system may include all or some of the following components: Conduit mechanism 2, Angling Mechanism 11, Wall-tensioning mechanism 15, Sub-intimal access mechanism 18, Tissue layer separation mechanism 28, Sub-intimal pocket creation mechanism 32, Intimal separation mechanism 46, and Valve securement mechanism 48.

It should also be noted that components described as parts of a device/mechanism may be considered as separate devices themselves. In addition, in embodiments in which separate devices are described, the separate devices may be considered as components of a system/mechanism.

Also, in other embodiments, the embodiments of the devices and methods described herein may be used twice—once to create a first flap on one side of the vessel, and again to create a second flap on the opposite side of the vessel. In some embodiments, the two flaps may optionally be secured by the securement mechanism 48, as similarly described herein.

Furthermore, although the various embodiments of devices and methods have been described with reference to blood vessels, in other embodiments, the devices and methods described herein may be used to create tissue flap in any bodily lumen in which valve creation is desired. Also, embodiments of the devices and methods described herein are not limited to being used to treat venous reflux. In other embodiments, embodiments of the devices and methods described herein may be used to treat reflux (or other medical conditions) in other luminal structures inside a patient.

Although particular embodiments have been shown and described, it will be understood that they are not intended to limit the claimed inventions, and it will be obvious to those skilled in the art that various changes and modifications may be made without departing from the spirit and scope of the claimed inventions. The claimed inventions are intended to cover alternatives, modifications, and equivalents.

What is claimed:

1. A method of manipulating tissue at a vessel, comprising:
   inserting a device percutaneously into a lumen of a vessel;
   advancing the device inside the lumen of the vessel until the device reaches a location in the vessel; and
   using the device to secure an artificially created flap created from a first portion of a wall of the vessel away from the first portion of the wall;
   wherein the flap is located on a first side of the vessel and is secured to a second side of the vessel such that the flap cannot contact the first side, wherein the second side is opposite from the first side.

2. The method of claim 1, wherein the device comprises a stitching material, and the act of using the device to secure the flap comprises using the stitching material to secure the flap away from the first portion of the wall.

3. The method of claim 1, wherein the device comprises a pin, and the act of using the device to secure the flap comprises using the pin to secure the flap away from the first portion of the wall.

4. The method of claim 1, wherein the device comprises tissue glue, and the act of using the device to secure the flap comprises using the tissue glue to secure the flap away from the first portion of the wall.

5. The method of claim 1, further comprising moving the flap from the first side of the vessel towards the second side of the vessel.

6. The method of claim 5, wherein the flap has an end that is separated from the vessel, the end of the flap located at a first position along the vessel; and wherein the flap is moved to reach the second side of the vessel, the end of the flap is located at a second position along the vessel that is offset from the first position.

7. The method of claim 1, further comprising:
   inserting a cutting device percutaneously into the lumen of the vessel; and
   using the cutting device in a process to create the flap from the first portion of the vessel.

8. The method of claim 7, wherein the act of using the cutting device comprises placing the cutting device inside the wall of the vessel.

9. The method of claim 8, wherein the cutting device comprises a blade.

10. The method of claim 8, wherein the cutting device comprises a tube for delivering fluid.

11. The method of claim 1, wherein the flap is secured to a second flap.

12. The method of claim 1, wherein the device has an elongated configuration, and carries a securing mechanism, and wherein the device is sized for insertion into the lumen of the vessel; and
   wherein the act of using the device to secure the flap comprises using the securing mechanism to secure the flap.

* * * * *